US007863241B2

(12) United States Patent
Cochrane

(10) Patent No.: US 7,863,241 B2
(45) Date of Patent: Jan. 4, 2011

(54) COMPOSITIONS FOR TREATMENT AND PREVENTION OF PULMONARY CONDITIONS

(75) Inventor: Charles G. Cochrane, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 118 days.

(21) Appl. No.: 10/971,461

(22) Filed: Oct. 22, 2004

(65) Prior Publication Data
US 2005/0070477 A1  Mar. 31, 2005

Related U.S. Application Data

(63) Continuation of application No. PCT/US03/12731, filed on Apr. 25, 2003.

(60) Provisional application No. 60/375,968, filed on Apr. 25, 2002.

(51) Int. Cl.
A61K 38/00 (2006.01)

(52) U.S. Cl. .............................. 514/12; 514/2; 514/13; 514/579; 530/300; 530/350

(58) Field of Classification Search .................. None
See application file for complete search history.

(56) References Cited

U.S. PATENT DOCUMENTS

| 4,916,117 | A | * | 4/1990 | Lezdey et al. ................ 514/8 |
| 4,938,949 | A | | 7/1990 | Borch et al. |
| 5,164,369 | A | | 11/1992 | Cochrane et al. |
| 5,260,273 | A | | 11/1993 | Cochrane et al. |
| 5,301,644 | A | | 4/1994 | Olmr |
| 5,407,914 | A | * | 4/1995 | Cochrane et al. ............. 514/12 |
| 5,707,634 | A | | 1/1998 | Schmitt |
| 5,734,014 | A | * | 3/1998 | Ishima et al. ................ 530/324 |
| 5,770,559 | A | | 6/1998 | Manning et al. |
| 5,780,440 | A | | 7/1998 | Lezdey et al. |
| 5,833,891 | A | | 11/1998 | Subramaniam et al. |
| 5,874,029 | A | | 2/1999 | Subramaniam et al. |
| 5,883,084 | A | | 3/1999 | Peterson et al. |
| 5,976,574 | A | | 11/1999 | Gordon |
| 5,981,474 | A | | 11/1999 | Manning et al. |
| 5,985,284 | A | | 11/1999 | Lowell |
| 5,993,805 | A | | 11/1999 | Sutton et al. |
| 6,001,336 | A | | 12/1999 | Gordon et al. |
| 6,013,619 | A | | 1/2000 | Cochrane et al. |
| 6,051,257 | A | | 4/2000 | Kodas et al. |
| 6,063,138 | A | | 5/2000 | Hanna et al. |
| 6,174,496 | B1 | | 1/2001 | Stein |
| 6,223,455 | B1 | | 5/2001 | Chickering, III et al. |
| 6,284,282 | B1 | | 9/2001 | Maa et al. |
| 7,053,176 | B1 | | 5/2006 | Hafner et al. |

FOREIGN PATENT DOCUMENTS

EP 402068 * 6/1990
WO WO 91/00871 1/1991
WO WO-03/090682 A2 11/2003

OTHER PUBLICATIONS

Han et al. (Zhonghua Bing Li Xue Za Zhi, Feb. 2000, vol. 29, No. 1, pp. 43-45.*
Wells, Biochemistry, vol. 29, pp. 8509-8517, 1990.*
Veldhuizen et al. (Biochemistry J., 1993, vol. 295, pp. 141-147).*
"International Search Report for corresponding PCT Application No. PCT/US03/12731", (Jul. 13, 2004), 3 pgs.
"IUPAC-IUB Commission on Biochemical Nomenclature—A One-Letter Notation for Amino Acid Sequences—Tenative Rules", *The Journal of Biological Chemistry*, 243(13), (1968), 3557-3559.
Bode, W., et al., "Natural Protein Proteinase Inhibitors and Their Interaction With Proteinases", *European Journal of Biochemistry*, 204(2), (1992), 433-451.
Cochrane, C. G., et al., "The Efficacy and Safety of $KL_4$-Surfactant in Preterm Infants With Respiratory Distress Syndrome", *American Journal of Respiratory and Critical Care Medicine*, 153(1), (1996), 404-410.
Cochrane, C. G., "Vascular Leak in Acute Lung Injury", *American Journal of Respiratory and Critical Care Medicine*, 163, 139 (Abstract Only), paper presented at the 2001 Meeting of the American Thoracic Society, (http://www.abstracts2view.com/atsall/view.php?nu=ATS1P1 1113),(2001), 1 pg.
Cowan, K. N., et al., "Complete Reversal of Fatal Pulmonary Hypertension in Rats by a Serine Elastase Inhibitor", *Nature Medicine*, 6, (Jun. 2000), 698-702.
Davis, R., et al., "Aprotinin—A Review of its Pharmacology and Therapeutic Efficacy in Reducing Blood Loss Associated With Cardiac Surgery", *Drugs*, 49(6), (1995), 954-983.
De Sanctis, G T., "Exogenous Surfactant Enhances Mucociliary Clearance in the Anaesthetized Dog", *European Respiratory Journal*, 7(9), (Sep. 1994), 1616-21.
Delaria, K. A., "Characterization of Placental Bikunin, a Novel Serine Protease Inhibitor", *The Journal of Biological Chemistry*, 272(18), (1997),12209-12214.
Dennis, M. S., et al. "Potent and Selective Kunitz Domain Inhibitors of Plasma Kallikrein Designed by Phage Display", *The Journal of Biological Chemistry*, 270(43), (1995), 25411-25417.
Dietrich, W., et al. "Reduction of Homologous Blood Requirement in Cardiac Surgery by Intraoperative Aprotinin Application—Clinical Experience in 152 Cardiac Surgical Patients", *The Thoracic and Cardiovascular Surgeon*, 37, (1989), 92-98.
Enhorning, G., et al., "Increased Airway Resistance Due to Surfactant Dysfunction can be Alleviated With Aerosol Surfactant.", *Canadian Journal of Physiology and Pharmacology*, 74(6), (1996), 687-691.

(Continued)

Primary Examiner—Hope A Robinson
(74) Attorney, Agent, or Firm—Hugh Wang; Thomas Fitting; Robin A. Chadwick

(57) ABSTRACT

The invention provides compositions and methods for treating pulmonary conditions and for reducing the negative effects of pulmonary inflammation. Such compositions and methods employ protease inhibitors and a lung surfactant mixture. The compositions and methods can also include lipase inhibitors (e.g. a phospholipase inhibitors) and antioxidants.

8 Claims, 14 Drawing Sheets

OTHER PUBLICATIONS

Enhorning, G., et al., "Pulmonary Surfactant Maintains Patency of Conducting Airways in the Rat", *American Journal of Respiratory and Critical Care Medicine*, 151(2), (1995), 554-556.

Fortes-Dias, C. L., et al., "Phospholipase $A_2$ Inhibitor From the Plasma of the South American Rattlesnake (*Crotalus durissus terrificus*)", *The Journal of Biological Chemistry*, 269(22), (1994), 15646-15651.

Friede, M., et al., "Lyophilized Liposomes as Shelf Items for the Preparation of Immunogenic Liposome—Peptide Conjugates", *Analytical Biochemistry*, 211, (1993), 117-122.

Glasser, S. W., et al., "Two SP-C Genes Encoding Human Pulmonary Surfactant Proteolipid", *The Journal of Biological Chemistry*, 263(21), (1988), 10326-10331.

Hite, R D., et al., "Hydrolysis of Surfactant-Associated Phosphatidylcholine by Mammalian Secretory Phospholipases $A_2$", *American Journal of Physiology*, 275(4 Pt 1), (Oct. 1998), L740-7.

Hite, R. D., "Surfactant Deficiency in Adults", *Clinical Pulmonary Medicine*, 9(1), (2002),39-45.

Hite, R D., et al., "The Spectrum of Surfactant Dysfunction in an Endobronchial Challenge Model of Asthma", *American Journal of Respiratory and Cirtical Care Medicine*, 159, (1999),A333.

Ilowite, J. S., et al., "Quantitative Deposition of Aerosolized Gentamicin in Cystic Firbrosis", *American Review of Respiratory Disease*, 136(6), (1987),1445-1449.

Jarjour, N N., et al., "Antigen-Induced Airway Inflammation in Atopic Subjects Generates Dysfunction of Pulmonary Surfactant", *American Journal of Respiratory and Critical Care Medicine*, 160(1), (Jul. 1999), 336-41.

Jobe, A. H., "Surfactant Treatment: Experimental Basis for Clinical Use", *American Review of Respiratory Disease*, 136(4), (1987),1032-1033.

Kharasch, V. S., et al., "Pulmonary Surfactant as a Vehicle for Intratracheal Delivery of Technetium Sulfur Colloid and Pentamidine in Hamster Lungs", *American Review of Respiratory Disease*, 144(4), (1991),909-913.

King, R. J., et al., "Surface Active Materials from Dog Lung. II. Composition and Physiological Correlations", *American Journal of Physiology*, 223(3), (1972), 715-726.

Kurashima, K , "A Pilot Study of Surfactant Inhalation in the Treatment of Asthmatic Attack", *Japan Journal of Allergology*, 40(2), (Feb. 1991), 160-3.

Kurashima, K , et al., "Surface Activity of Sputum From Acute Asthmatic Patients", *American Journal of Respiratory and Critical Care Medicine*, 155(4), (Apr. 1997), 1254-1259.

Laube, B. L., et al., "Homogeneity of Bronchopulmonary Distribution of $^{99m}Tc$ Aerosol in Normal Subjects and in Cystic Fibrosis Patients", *Chest*, 95(4), (1989),822-830.

Lee, C. T., et al., "Elastolytic Activity in Pulmonary Lavage Fluid From Patients With Adult Respiratory-Distress Syndrome", *The New England Journal of Medicine*, 304(4), (1981),192-196.

Liu, M , et al., "Dysfunction of Guinea-Pig Pulmonary Surfactant and Type II Pneumocytes After Repetitive Challenge With Aerosolized Ovalbumin", *Clinical and Experimental Allergy*, 27(7), (Jul. 1997),802-7.

Maa, Y.-F., et al., "Effect of Spray Dying and Subsequent Processing Conditions on Residual Moisture Content and Physical/Biochemical Stability of Protein Inhalation Powders", *Pharmaceutical Research*, 15(5), (1998), 768-775.

Maa, Y.-F., et al., "The Effect of Operating and Formulation Variables on the Morphology of Spray-Dried Protein Particles", *Pharmaceutical Development and Technology*, 2(3), (1997),213-223.

Mayer, L. D., "Influence of Vesicle Size, Lipid Composition, and Drug-to-Lipid Ratio on the Biological Activity of Liposomal Doxorubicin in Mice", *Cancer Research*, 49(21), (1989), 5922-5930.

Mayer, L. D., et al., "Uptake of Adriamycin Into Large Unilamellar Vesicles in Response to a pH Gradient", *Biochmica et Biophysica Acta (BBA)—Biomembranes*, 857(1), (1986),123-126.

Notter, R. H., et al., "Lung Surfactants for Replacement Therapy: Biochemical, Biophysical, and Clinical Aspects", *Clinics in Perinatology.*, 14(3), (1987), 433-479.

Olson, F. , et al., "Preparation of Liposomes of Defined Size Distribution by Extrusion Through Polycardonate Membranes", *Biochimica et Biophysica Acta (BBA)—Biomembranes*, 557(1), (1979), 9-23.

Petersen, L. C., et al., "Inhibitory Properties of a Novel Human Kunitz-Type Protease Inhibitor Homologous to Tissue Factor Pathway Inhibitor", *Biochemistry*, 35, (1996), 266-272.

Puchelle, E., et al., "Rheological and Transport Properties of Airway Secretations in Cystic Fibrosis-Relationships With the Degree of Infection and Severity of the Disease", *European Journal of Clinical Investigation*, 15(6), (1985),389-394.

Revak, S. D., et al., "Reconstitution of Surfactant Activity Using Purified Human Apoprotein and Phospholipids Measured in vitro and in vivo", *American Review of Respiratory Disease*, 134(6), (1986),1258-1265.

Robertson, B. , "Surfactant Substitution: Experimental Models and Clinical Applications", *Lung*, 158, (1980),57-68.

Sarbolouki, M. N., et al., "Storage Stability of Stabilized MLV and REV Liposomes Containing Sodium Methotrexate (Aqueous & Lyophilized)", *PDA Journal of Pharmaceutical Science and Technology*, 52(1), (1998), 23-27.

Sprecher, C. A., "Molecular Cloning, Expression, and Partial Characterization of a Second Human Tissue-Factor-Pathway Inhibitor", *Proc. Natl. Acad. Sci. USA*, 91(8), (1994) ,3353-3357.

Szoka, F., JR., et al., "Comparative Properties and Methods of Preparation of Lipid Vesicles (Liposomes).", *Annual Review of Biophysics and Bioengineering*, 9, (1980), 467-508.

Tainter, M. L., et al., "Alevaire as a Mucolytic Agent", *The New England Journal of Medicine*, 253(18), (1955),764-767.

Tanaka, K. , et al., "Effect of Thielocin A1β on Bee Venom Phospholipase $A_2$-Induced Edema in Mouse Paw", *European Journal of Pharmacology*, 279(2-3), (1995),143-148.

Vincent, J. S., et al., "Raman Spectroscopic Studies of Model Human Pulmonary Surfactant Systems: Phospholipid Interactions with Peptide Paradigms for the Surfactant Protein SP-B", *Biochemistry*, 30, (1991), 8395-8401.

Wachtfogel, Y T., et al., "Aprotinin Inhibits the Contact, Neutrophil, and Platelet Activation Systems During Simulated Extracorporeal Perfusion", *The Journal of Thoracic and Cardiovascular Surgery*, 106(1), (1993), 1-10.

Wallner, B. P., et al., "Cloning and Expression of Human Lipocortin, a Phospholipase $A_2$ Inhibitor With Potential Anti-Inflammatory Activity", *Nature*, 320(6057), (1986), 77-81.

Westaby, S. , "Aprotinin in Perspective", *The Annals of Thoracic Surgery*, 55(4), (1993), 1033-1041.

Glassman, H. N., "Hemolytic Activity of Some Nonionic Surface-Active Agents", *Science*, 111(2895), (Jun. 23, 1950), 688-689.

Revak, S. D., et al., "Efficacy of Synthetic Peptide-Containing Surfactant in the Treatment of Respiratory Distress Syndrome in Preterm Infant Rhesus Monkeys", *Pediatric Research*, 39(4), (1996), 715-724.

\* cited by examiner

SEQUENCE LISTING

```
<160> NUMBER OF SEQ ID NOS: 30

<210> SEQ ID NO 1
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 1
```

```
Lys Leu Leu Leu Leu Lys Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 2

Lys Leu Leu Leu Leu Leu Leu Leu Leu Lys Leu Leu Leu Leu Leu
1               5                   10                  15

Leu Leu Lys Leu Leu
            20

<210> SEQ ID NO 3
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 3

Lys Lys Leu Leu Leu Leu Leu Leu Leu Lys Lys Leu Leu Leu Leu
1               5                   10                  15

Leu Leu Lys Lys Leu
            20

<210> SEQ ID NO 4
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 4

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 5
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 5

Arg Leu Leu Leu Leu Arg Leu Leu Leu Leu Arg Leu Leu Leu Leu Arg
1               5                   10                  15

Leu Leu Leu Leu Arg
            20

<210> SEQ ID NO 6
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 6
```

```
Arg Leu Leu Leu Leu Leu Leu Leu Arg Leu Leu Leu Leu Leu
1               5                   10                  15

Leu Leu Arg Leu Leu
            20
```

<210> SEQ ID NO 7
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 7

```
Arg Arg Leu Leu Leu Leu Leu Leu Leu Arg Arg Leu Leu Leu Leu
1               5                   10                  15

Leu Leu Arg Arg Leu
            20
```

<210> SEQ ID NO 8
<211> LENGTH: 19
<212> TYPE: PRT
<213> ORGANISM: Artificial Sequence
<220> FEATURE:
<223> OTHER INFORMATION: A synthetic surfactant protein

<400> SEQUENCE: 8

```
Arg Leu Leu Leu Leu Cys Leu Leu Arg Leu Leu Leu Leu Cys Leu
1               5                   10                  15

Leu Leu Arg
```

<210> SEQ ID NO 9
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 9

```
Arg Leu Leu Leu Leu Cys Leu Leu Leu Arg Leu Leu Leu Leu Cys Leu
1               5                   10                  15

Leu Leu Arg Leu Leu
            20
```

<210> SEQ ID NO 10
<211> LENGTH: 28
<212> TYPE: PRT
<213> ORGANISM: Artificial Sequence
<220> FEATURE:
<223> OTHER INFORMATION: A synthetic surfactant protein

<400> SEQUENCE: 10

```
Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg
            20                  25
```

<210> SEQ ID NO 11

<400> SEQUENCE: 11

000

<210> SEQ ID NO 12

<400> SEQUENCE: 12

000

<210> SEQ ID NO 13
<211> LENGTH: 21
<212> TYPE: PRT
<213> ORGANISM: Artificial Sequence
<220> FEATURE:
<223> OTHER INFORMATION: A synthetic surfactant protein

<400> SEQUENCE: 13

His Leu Leu Leu Leu His Leu Leu Leu His Leu Leu Leu Leu His
1               5                   10                  15

Leu Leu Leu Leu His
            20

<210> SEQ ID NO 14
<211> LENGTH: 379
<212> TYPE: PRT
<213> ORGANISM: Homo sapiens

<400> SEQUENCE: 14

Met Glu Gln Leu Ser Ser Ala Asn Thr Arg Phe Ala Leu Asp Leu Phe
1               5                   10                  15

Leu Ala Leu Ser Glu Asn Asn Pro Ala Gly Asn Ile Phe Ile Ser Pro
            20                  25                  30

Phe Ser Ile Ser Ser Ala Met Ala Met Val Phe Leu Gly Thr Arg Gly
        35                  40                  45

Asn Thr Ala Ala Gln Leu Ser Lys Thr Phe His Phe Asn Thr Val Glu
    50                  55                  60

Glu Val His Ser Arg Phe Gln Ser Leu Asn Ala Asp Ile Asn Lys Arg
65                  70                  75                  80

Gly Ala Ser Tyr Ile Leu Lys Leu Ala Asn Arg Leu Tyr Gly Glu Lys
                85                  90                  95

Thr Tyr Asn Phe Leu Pro Glu Phe Leu Val Ser Thr Gln Lys Thr Tyr
            100                 105                 110

Gly Ala Asp Leu Ala Ser Val Asp Phe Gln His Ala Ser Glu Asp Ala
        115                 120                 125

Arg Lys Thr Ile Asn Gln Trp Val Lys Gly Gln Thr Glu Gly Lys Ile
    130                 135                 140

Pro Glu Leu Leu Ala Ser Gly Met Val Asp Asn Met Thr Lys Leu Val
145                 150                 155                 160

Leu Val Asn Ala Ile Tyr Phe Lys Gly Asn Trp Lys Asp Lys Phe Met
                165                 170                 175

Lys Glu Ala Thr Thr Asn Ala Pro Phe Arg Leu Asn Lys Lys Asp Arg
            180                 185                 190

Lys Thr Val Lys Met Met Tyr Gln Lys Lys Phe Ala Tyr Gly Tyr
        195                 200                 205

Ile Glu Asp Leu Lys Cys Arg Val Leu Glu Leu Pro Tyr Gln Gly Glu
    210                 215                 220

Glu Leu Ser Met Val Ile Leu Leu Pro Asp Asp Ile Glu Asp Glu Ser
225                 230                 235                 240

Thr Gly Leu Lys Lys Ile Glu Glu Gln Leu Thr Leu Glu Lys Leu His
                245                 250                 255

Glu Trp Thr Lys Pro Gly Asn Leu Asp Phe Ile Glu Val Asn Val Ser
            260                 265                 270

```
Leu Pro Arg Phe Lys Leu Glu Glu Ser Tyr Thr Leu Asn Ser Asp Leu
            275                 280                 285

Ala Arg Leu Gly Val Gln Asp Leu Phe Asn Ser Ser Lys Ala Asp Leu
            290                 295                 300

Ser Gly Met Ser Gly Ala Arg Asp Ile Phe Ile Ser Lys Ile Val His
305                 310                 315                 320

Lys Ser Phe Val Glu Val Asn Glu Glu Gly Thr Glu Ala Ala Ala Ala
                    325                 330                 335

Thr Ala Gly Ile Ala Thr Phe Cys Met Leu Met Pro Glu Glu Asn Phe
                340                 345                 350

Thr Ala Asp His Pro Phe Leu Phe Phe Ile Arg His Asn Ser Ser Gly
            355                 360                 365

Ser Ile Leu Phe Leu Gly Arg Phe Ser Ser Pro
            370                 375

<210> SEQ ID NO 15
<211> LENGTH: 418
<212> TYPE: PRT
<213> ORGANISM: Homo sapiens

<400> SEQUENCE: 15

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
```

```
                    260                 265                 270
Thr Ala Ile Phe Phe Leu Pro Asp Glu Gly Lys Leu Gln His Leu Glu
                275                 280                 285
Asn Glu Leu Thr His Asp Ile Ile Thr Lys Phe Leu Glu Asn Glu Asp
            290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
        370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 16
<211> LENGTH: 252
<212> TYPE: PRT
<213> ORGANISM: Homo sapiens

<400> SEQUENCE: 16

Met Ala Gln Leu Cys Gly Leu Arg Arg Ser Arg Ala Phe Leu Ala Leu
1               5                   10                  15
Leu Gly Ser Leu Leu Leu Ser Gly Val Leu Ala Ala Asp Arg Glu Arg
            20                  25                  30
Ser Ile His Asp Phe Cys Leu Val Ser Lys Val Val Gly Arg Cys Arg
        35                  40                  45
Ala Ser Met Pro Arg Trp Trp Tyr Asn Val Thr Asp Gly Ser Cys Gln
    50                  55                  60
Leu Phe Val Tyr Gly Gly Cys Asp Gly Asn Ser Asn Asn Tyr Leu Thr
65                  70                  75                  80
Lys Glu Glu Cys Leu Lys Lys Cys Ala Thr Val Thr Glu Asn Ala Thr
                85                  90                  95
Gly Asp Leu Ala Thr Ser Arg Asn Ala Ala Asp Ser Ser Val Pro Ser
            100                 105                 110
Ala Pro Arg Arg Gln Asp Ser Glu Asp His Ser Ser Asp Met Phe Asn
        115                 120                 125
Tyr Glu Glu Tyr Cys Thr Ala Asn Ala Val Thr Gly Pro Cys Arg Ala
    130                 135                 140
Ser Phe Pro Arg Trp Tyr Phe Asp Val Glu Arg Asn Ser Cys Asn Asn
145                 150                 155                 160
Phe Ile Tyr Gly Gly Cys Arg Gly Asn Lys Asn Ser Tyr Arg Ser Glu
                165                 170                 175
Glu Ala Cys Met Leu Arg Cys Phe Arg Gln Gln Glu Asn Pro Pro Leu
            180                 185                 190
Pro Leu Gly Ser Lys Val Val Val Leu Ala Gly Leu Phe Val Met Val
        195                 200                 205
Leu Ile Leu Phe Leu Gly Ala Ser Met Val Tyr Leu Ile Arg Val Ala
```

-continued

```
                210                 215                 220
Arg Arg Asn Gln Glu Arg Ala Leu Arg Thr Val Trp Ser Ser Gly Asp
225                 230                 235                 240

Asp Lys Glu Gln Leu Val Lys Asn Thr Tyr Val Leu
                245                 250

<210> SEQ ID NO 17
<211> LENGTH: 57
<212> TYPE: PRT
<213> ORGANISM: Homo sapiens

<400> SEQUENCE: 17

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
                20                  25                  30

Leu Lys Asp Thr Asp Cys Pro Gly Ile Lys Lys Cys Cys Glu Gly Ser
                35                  40                  45

Cys Gly Met Ala Cys Phe Val Pro Gln
                50                  55

<210> SEQ ID NO 18
<211> LENGTH: 117
<212> TYPE: PRT
<213> ORGANISM: Homo sapiens

<400> SEQUENCE: 18

Met Arg Ala Ser Ser Phe Leu Ile Val Val Phe Leu Ile Ala Gly
1               5                   10                  15

Thr Leu Val Leu Glu Ala Ala Val Thr Gly Val Pro Val Lys Gly Gln
                20                  25                  30

Asp Thr Val Lys Gly Arg Val Pro Phe Asn Gly Gln Asp Pro Val Lys
                35                  40                  45

Gly Gln Val Ser Val Lys Gly Gln Asp Lys Val Lys Ala Gln Glu Pro
        50                  55                  60

Val Lys Gly Pro Val Ser Thr Lys Pro Gly Ser Cys Pro Ile Ile Leu
65                  70                  75                  80

Ile Arg Cys Ala Met Leu Asn Pro Pro Asn Arg Cys Leu Lys Asp Thr
                85                  90                  95

Asp Cys Pro Gly Ile Lys Lys Cys Cys Glu Gly Ser Cys Gly Met Ala
                100                 105                 110

Cys Phe Val Pro Gln
        115

<210> SEQ ID NO 19
<211> LENGTH: 134
<212> TYPE: PRT
<213> ORGANISM: Bos taurus

<400> SEQUENCE: 19

Gln Glu Pro Val Lys Gly Gln Asp Pro Val Lys Gly Gln Asp Pro Val
1               5                   10                  15

Lys Gly Gln Asp Pro Val Lys Gly Gln Asp Pro Val Lys Asp Gln Asn
                20                  25                  30

Pro Val Arg Gly Gln Glu Pro Val Lys Gly Gln Asp Pro Val Lys Gly
                35                  40                  45

Gln Asp Pro Val Lys Gly Gln Asp Pro Val Lys Gly Gln Glu Pro Val
        50                  55                  60
```

Lys Gly Gln Asp Pro Val Lys Gly Gln Asp Pro Val Lys Arg Gln Gly
65                  70                  75                  80

Arg Ile Gly Gly Pro Leu Leu Thr Lys Pro Gly Ser Cys Pro Arg Val
                85                  90                  95

Leu Ile Arg Cys Ala Met Met Asn Pro Pro Asn Arg Cys Leu Arg Asp
            100                 105                 110

Ala Gln Cys Pro Gly Val Lys Lys Cys Cys Glu Gly Ser Cys Gly Lys
        115                 120                 125

Thr Cys Met Asp Pro Gln
    130

<210> SEQ ID NO 20
<211> LENGTH: 207
<212> TYPE: PRT
<213> ORGANISM: Homo sapiens

<400> SEQUENCE: 20

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 21
<211> LENGTH: 220
<212> TYPE: PRT
<213> ORGANISM: Homo sapiens

<400> SEQUENCE: 21

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

```
Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
            210                 215                 220

<210> SEQ ID NO 22
<211> LENGTH: 211
<212> TYPE: PRT
<213> ORGANISM: Homo sapiens

<400> SEQUENCE: 22

Met Thr Pro Trp Leu Gly Leu Ile Val Leu Leu Gly Ser Trp Ser Leu
  1               5                  10                  15

Gly Asp Trp Gly Ala Glu Ala Cys Thr Cys Ser Pro Ser His Pro Gln
                 20                  25                  30

Asp Ala Phe Cys Asn Ser Asp Ile Val Ile Arg Ala Lys Val Val Gly
             35                  40                  45

Lys Lys Leu Val Lys Glu Gly Pro Phe Gly Thr Leu Val Tyr Thr Ile
 50                  55                  60

Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
                 85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
            115                 120                 125

Leu Ser Gln Arg Lys Gly Leu Asn Tyr Arg Tyr His Leu Gly Cys Asn
130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
                180                 185                 190

Ser Trp Tyr Arg Gly Trp Ala Pro Pro Asp Lys Ser Ile Ile Asn Ala
```

-continued

```
                195                 200                 205
Thr Asp Pro
    210

<210> SEQ ID NO 23
<211> LENGTH: 132
<212> TYPE: PRT
<213> ORGANISM: Homo sapiens

<400> SEQUENCE: 23

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130

<210> SEQ ID NO 24
<211> LENGTH: 5
<212> TYPE: PRT
<213> ORGANISM: Artificial Sequence
<220> FEATURE:
<223> OTHER INFORMATION: A synthetic peptide used as an elastase
      substrate
<220> FEATURE:
<221> NAME/KEY: SITE
<222> LOCATION: 1
<223> OTHER INFORMATION: Xaa = MeO-Suc
<220> FEATURE:
<221> NAME/KEY: SITE
<222> LOCATION: 5
<223> OTHER INFORMATION: Xaa = Val-pNA

<400> SEQUENCE: 24

Xaa Ala Ala Pro Xaa
1               5

<210> SEQ ID NO 25
<211> LENGTH: 248
<212> TYPE: PRT
<213> ORGANISM: Homo sapiens

<400> SEQUENCE: 25

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
            20                  25                  30

Pro Gly Thr Pro Gly Ser His Gly Leu Pro Gly Arg His Gly Arg Asp
        35                  40                  45
```

-continued

```
Gly Leu Lys Gly Asp Leu Gly Pro Gly Pro Met Gly Pro Gly
 50                  55                  60

Glu Met Pro Cys Pro Pro Gly Asn Asp Gly Leu Pro Gly Ala Pro Gly
 65                  70                  75                  80

Ile Pro Gly Glu Cys Gly Glu Lys Gly Glu Pro Gly Glu Arg Gly Pro
                 85                  90                  95

Pro Gly Leu Arg Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 26
<211> LENGTH: 248
<212> TYPE: PRT
<213> ORGANISM: Homo sapiens

<400> SEQUENCE: 26

Met Trp Leu Cys Pro Leu Ala Leu Asn Leu Ile Leu Met Ala Ala Ser
 1               5                  10                  15

Gly Ala Ala Cys Glu Val Lys Asp Val Cys Val Gly Ser Pro Gly Ile
                 20                  25                  30

Pro Gly Thr Pro Gly Ser His Gly Leu Pro Gly Arg Asp Gly Arg Asp
            35                  40                  45

Gly Val Lys Gly Asp Pro Gly Pro Pro Gly Pro Met Gly Pro Pro Gly
 50                  55                  60

Glu Thr Pro Cys Pro Pro Gly Asn Asn Gly Leu Pro Gly Ala Pro Gly
 65                  70                  75                  80

Val Pro Gly Glu Arg Gly Glu Lys Gly Glu Ala Gly Glu Arg Gly Pro
                 85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175
```

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
            195                 200                 205

Thr Asn Trp Tyr Arg Gly Glu Pro Ala Gly Arg Gly Lys Glu Gln Cys
        210                 215                 220

Val Glu Met Tyr Thr Asp Gly Gln Trp Asn Asp Arg Asn Cys Leu Tyr
225                 230                 235                 240

Ser Arg Leu Thr Ile Cys Asp Phe
                245

<210> SEQ ID NO 27
<211> LENGTH: 381
<212> TYPE: PRT
<213> ORGANISM: Homo sapiens

<400> SEQUENCE: 27

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
                20                  25                  30

Ala Gln Gly Pro Glu Phe Trp Cys Gln Ser Leu Glu Gln Ala Leu Gln
            35                  40                  45

Cys Arg Ala Leu Gly His Cys Leu Gln Glu Val Trp Gly His Val Gly
        50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Ile Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Arg Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
        275                 280                 285

Thr Gly Glu Trp Leu Pro Arg Asp Ser Glu Cys His Leu Cys Met Ser

```
                290                 295                 300
Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
                340                 345                 350

Gly Trp Asp Ala His Thr Thr Cys Gln Ala Leu Gly Val Cys Gly Thr
                355                 360                 365

Met Ser Ser Pro Leu Gln Cys Ile His Ser Pro Asp Leu
370                 375                 380

<210> SEQ ID NO 28
<211> LENGTH: 197
<212> TYPE: PRT
<213> ORGANISM: Homo sapiens

<400> SEQUENCE: 28

Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
                20                  25                  30

Leu Lys Arg Leu Leu Ile Val Val Val Val Val Leu Ile Val Val
            35                  40                  45

Val Ile Val Gly Ala Leu Leu Met Gly Leu His Met Ser Gln Lys His
    50                  55                  60

Thr Glu Met Val Leu Glu Met Ser Ile Gly Ala Pro Glu Ala Gln Gln
65                  70                  75                  80

Arg Leu Ala Leu Ser Glu His Leu Val Thr Thr Ala Thr Phe Ser Ile
                85                  90                  95

Gly Ser Thr Gly Leu Val Val Tyr Asp Tyr Gln Gln Leu Leu Ile Ala
                100                 105                 110

Tyr Lys Pro Ala Pro Gly Thr Cys Cys Tyr Ile Met Lys Ile Ala Pro
            115                 120                 125

Glu Ser Ile Pro Ser Leu Glu Ala Leu Asn Arg Lys Val His Asn Phe
130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
            180                 185                 190

Pro Leu Tyr Tyr Ile
        195

<210> SEQ ID NO 29
<211> LENGTH: 374
<212> TYPE: PRT
<213> ORGANISM: Homo sapiens

<400> SEQUENCE: 29

Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
```

```
                    35                  40                  45
Arg Asp Gly Arg Asp Gly Arg Glu Gly Pro Arg Gly Glu Lys Gly Asp
 50                  55                  60

Pro Gly Leu Pro Gly Pro Met Gly Leu Ser Gly Leu Gln Gly Pro Thr
 65                  70                  75                  80

Gly Pro Val Gly Pro Lys Gly Glu Asn Gly Ser Ala Gly Glu Pro Gly
                 85                  90                  95

Pro Lys Gly Glu Arg Gly Leu Ser Gly Pro Pro Gly Leu Pro Gly Ile
                100                 105                 110

Pro Gly Pro Ala Gly Lys Glu Gly Pro Ser Gly Lys Gln Gly Asn Ile
                115                 120                 125

Gly Pro Gln Gly Lys Pro Gly Pro Lys Gly Glu Ala Gly Pro Lys Gly
                130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
                180                 185                 190

Ala Pro Gly Ser Arg Gly Pro Pro Gly Leu Lys Gly Asp Arg Gly Val
                195                 200                 205

Pro Gly Asp Arg Gly Ile Lys Gly Glu Ser Gly Leu Pro Asp Ser Ala
                210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

Arg Ser Val Gly Asp Lys Ile Phe Arg Thr Ala Asp Ser Glu Lys Pro
                260                 265                 270

Phe Glu Asp Ala Gln Glu Met Cys Lys Gln Ala Gly Gly Gln Leu Ala
                275                 280                 285

Ser Pro Arg Ser Ala Thr Glu Asn Ala Ala Ile Gln Gln Leu Ile Thr
                290                 295                 300

Ala His Asn Lys Ala Ala Phe Leu Ser Met Thr Asp Val Gly Thr Glu
305                 310                 315                 320

Gly Lys Phe Thr Tyr Pro Thr Gly Glu Pro Leu Val Tyr Ser Asn Trp
                325                 330                 335

Ala Pro Gly Glu Pro Asn Asn Asn Gly Gly Ala Glu Asn Cys Val Glu
                340                 345                 350

Ile Phe Thr Asn Gly Gln Trp Asn Asp Lys Ala Cys Gly Glu Gln Arg
                355                 360                 365

Leu Val Ile Cys Glu Phe
    370

<210> SEQ ID NO 30
<211> LENGTH: 9
<212> TYPE: PRT
<213> ORGANISM: Artificial Sequence
<220> FEATURE:
<223> OTHER INFORMATION: A synthetic WMAP-10 peptide.
<220> FEATURE:
<221> NAME/KEY: SITE
<222> LOCATION: 1
<223> OTHER INFORMATION: Xaa = succinyl-Leu
<220> FEATURE:
<221> NAME/KEY: SITE
<222> LOCATION: 9
```

```
<223> OTHER INFORMATION: Xaa = Lys-amide

<400> SEQUENCE: 30

Xaa Leu Glu Lys Leu Leu Gln Trp Xaa
 1               5
```

COMPOSITIONS FOR TREATMENT AND PREVENTION OF PULMONARY CONDITIONS

RELATED APPLICATIONS

This application is a continuation under 35 U.S.C. §111(a) of International Application No. PCT/US03/12731 filed Apr. 25, 2003 and published in English as WO 03/090682 A2 on Nov. 6, 2003, which claims the benefit of U.S. Provisional Application Ser. No. 60/375,968 filed Apr. 25, 2002, which applications and publication are incorporated herein by reference and made a part hereof.

FIELD OF THE INVENTION

The invention relates to pharmaceutical compositions for preventing destruction of pulmonary tissues before or during inflammation of the lungs, and to methods of forming and using such compositions.

BACKGROUND OF THE INVENTION

Endogenous degradation enzymes such as lipases and proteolytic enzymes serve to breakdown invading organisms, antigen-antibody complexes and certain lipids and proteins that are no longer necessary or useful to the organism. In a normally functioning organism, such enzymes are produced in a limited quantity and are regulated in part through the synthesis of inhibitors.

A disturbance of the balance between enzymes and their inhibitors can lead to enzyme-mediated tissue destruction. Such destruction can occur in a variety of conditions, including inflammation, emphysema, asthma, chronic obstructive pulmonary disease (COPD), arthritis, glomerulonephritis, periodontitis, muscular dystrophy, tumor invasion and various other pathological conditions. In certain situations, e.g., severe pathological processes such as sepsis or acute leukemia, the amount of free proteolytic enzymes present increases due to the release of enzyme from secretory cells. In organisms where such aberrant conditions are present, serious damage to the organism can occur unless measures are taken to control the action of degradation enzymes.

The lungs in a human comprise 6% of the mammalian body volume and are composed of numerous small gas sacs, the alveoli. The primary purpose of the lungs is to facilitate gas interchange with the systemic circulation. The alveoli are therefore perfused by an extensive blood capillary network that brings mixed venous blood for gas exchange with fresh alveolar gas, across the pulmonary epithelial and endothelial barrier. The alveolar membrane has a total surface area of more than 100 $m^2$ and a thickness of less than 1 µm. Diseases or conditions that cause destruction of alveolar membrane barriers can lead to fluid leakage into alveoli, resulting in loss of lung function.

For example, Acute Respiratory Distress Syndrome (ARDS) is a descriptive expression that is applied to a large number of acute, diffuse infiltrative pulmonary lesions of differing etiology that are associated with severe gas exchange disorders (in particular arterial hypoxemia). ARDS is often associated with a "leaky" capillary response. The expression "Acute Respiratory Distress Syndrome" is used because of the numerous clinical and pathological features common with Infant Respiratory Distress Syndrome (IRDS). While IRDS is associated with lung surfactant deficiency, ARDS is associated with lung surfactant malfunction. With a mortality of 50-60% (survey in Schuster Chest 1995, 107: 1721-26), the prognosis of an ARDS patient is unfavorable.

To prevent or treat lung diseases, drugs may be directly delivered to the diseased tissue by bronchoalveolar lavage procedures, by liquid bolus administration through the trachea or by aerosol drug solution (e.g. by using a nebulizer) and subsequent inhalation of the aerosol droplets containing the drug. However, even where one directs the drug solution to the lungs, there are substantial uncertainties about how efficacious the drug or its administration will be. For example, the drug may be present in high concentrations in some areas while other areas receive little or no drug, the half-life of the drug in the lungs may be relatively short due to breakdown or absorption into the vascular system. There is also the problem of the effect of aerosolization on the drug. The drug may be degraded by the nebulizing action of the nebulizer or inactivated by oxidation. There is also the uncertainty concerning the ability to maintain an effective dosage for an extended period, without detrimental effect to the lungs or other organs of the host. Nor is it predictable whether a protein formulated for delivery in a dry powder form will retain its biological activity.

Pharmaceutical compositions containing some low molecular weight drugs have been delivered by pulmonary administration, most notably beta-androgenic antagonists to treat asthma Other low molecular weight non-proteinaceous compounds, including corticosteroids and cromolyn sodium, have been administered systemically via pulmonary absorption. Not all low molecular weight drugs, however, can be efficaciously administered through the lung. For example, pulmonary administration of aminoglycoside antibiotics, anti-viral drugs and anti-cancer drugs for systemic action has met with mixed success. In some cases, the drug was found to be irritating and bronchoconstrictive. Thus, even with low molecular weight substances, it is not at all predictable that the pulmonary delivery of such compounds will be an effective means of administration. See generally Peptide and Protein Drug Delivery, ed. V. Lee, Marcel Dekker, N.Y., 1990, pp. 1-11. Various factors intrinsic to the drug itself, the pharmaceutical composition, the delivery device, and particularly the lung, or a combination of these factors, can influence the success of pulmonary administration.

Hence, improvement is needed in the presently available compositions and methods for treating pulmonary conditions.

SUMMARY OF THE INVENTION

The invention generally relates to compositions and methods for treating pulmonary conditions. The compositions include at least one lung surfactant polypeptide and at least one inhibitor of a mediator of tissue destruction that is active during inflammation. Mediators of tissue destruction that are active during inflammation include any compound, enzyme, or other factor that is generated by the mammalian body as part of the inflammatory response and that can injure or destroy mammalian tissues. Examples of such mediators of tissue destruction include proteases, lipases, oxidants and the like. The inhibitor of such a mediator can, for example, be a protease inhibitor, an anti-oxidant, a lipase inhibitor or a phospholipase inhibitor.

In one aspect, the invention includes a composition that comprises a lung surfactant polypeptide with at least one protease inhibitor. Lipase inhibitors, phospholipase inhibitors and/or anti-oxidants can also be included in the composition. This composition can be administered directly to the lungs via bronchoalveolar lavage, bolus liquid drip, inhalation and the like.

In another aspect, the invention includes an aerosolized composition for delivering the active agents to a patient via inhalation. The composition can comprise aerosol particles comprising at least one surfactant polypeptide with at least one protease inhibitor. Lipase inhibitors, phospholipase inhibitors and/or anti-oxidants can also be included in the composition.

The protease inhibitors, lipase inhibitors, phospholipase inhibitors and anti-oxidants employed in the compositions and methods of the invention can be any such inhibitors or any anti-oxidants available to one of skill in the art.

In some embodiments, the protease inhibitor is a Kunitz inhibitor or a serine protease inhibitor. For example, the protease inhibitor may inhibit trypsin, chymotrypsin, elastase, kallikrein, plasmin, coagulation factor XIa, coagulation factor IXa, collagenase, cathepsin G, human leukocyte elastase or human secretory leukocyte protease. The protease inhibitor can, for example, be a human leukocyte elastase inhibitor, an alpha 1-proteinase inhibitor, a human secretory leukocyte protease inhibitor, collagenase inhibitor, cathepsin G inhibitor, alpha1-antitrypsin, alpha-1-antichymotrypsin, C-reactive protein, elafin or a combination thereof. In some embodiments, the protease inhibitor comprises a polypeptide comprising SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

In some embodiments, the lipase inhibitor is a phospholipase $A_2$ inhibitor. The lipase inhibitor can also, for example, be p-bromophenacyl bromide, thielocin A1 beta, lipocortin, annexin I or Crotalus phospholipase A2 inhibitor.

The anti-oxidant can, for example, be catalase, glutathione, N-acetylcysteine, procysteine, or alpha-tocopherol. Exemplary anti-oxidants also include EUK134.

As described above, compositions for pulmonary administration contain a lung surfactant polypeptide. The lung-surfactant polypeptide can have about 10 to about 60 amino acid residues with an amino acid sequence of alternating hydrophobic and hydrophilic amino acid residue regions represented by the formula $(Z_a U_b)_c Z_d$, where Z is a hydrophilic amino acid residue, U is a hydrophobic amino acid residue, "a" is an integer of about 1 to about 5, "b" is an integer of about 3 to about 20, "c" is an integer of about 1 to about 10, and "d" is an integer of about 0 to about 3. The inhibitor(s) and/or anti-oxidants can make up 1 to 80, typically 2-50 dry weight percent of the formulation.

In exemplary lung-surfactant polypeptides, Z is histidine, lysine, arginine, aspartic acid, glutamic acid, 5-hydroxylysine, 4-hydroxyproline, and/or 3-hydroxyproline, and U is valine, isoleucine, leucine, cysteine, tyrosine, phenylalanine, and/or an α-aminoaliphatic carboxylic acid, such as α-aminobutanoic acid, α-aminopentanoic acid, α-amino-2-methylpropanoic acid, or α-aminohexanoic acid.

One class of surfactant proteins have the sequence:

| | |
|---|---|
| KLLLLKLLLLKLLLLKLLLLK, | (SEQ ID NO: 1) |
| KLLLLLLLLKLLLLLLLLKLL, | (SEQ ID NO: 2) |
| KKLLLLLLLKKLLLLLLLKKL, | (SEQ ID NO: 3) |
| DLLLLDLLLLDLLLLDLLLLD, | (SEQ ID NO: 4) |
| RLLLLRLLLLRLLLLRLLLLR, | (SEQ ID NO: 5) |

-continued

| | |
|---|---|
| RLLLLLLLLRLLLLLLLLRLL, | (SEQ ID NO: 6) |
| RRLLLLLLLRRLLLLLLLRRL, | (SEQ ID NO: 7) |
| RLLLLCLLLRLLLLCLLLR, | (SEQ ID NO: 8) |
| RLLLLCLLLRLLLLCLLLRLL, or | (SEQ ID NO: 9) |
| RLLLLCLLLRLLLLCLLLRLLLLCLLLR. | (SEQ ID NO: 10) |

The compositions for pulmonary administration can contain a surfactant mixture of (i) 50-95 dry weight percent phospholipid, (ii) 2-25 dry weight percent of a spreading agent effective to promote incorporation and distribution of the phospholipid within the surface lining layer of the lung, and (iii) 0.1 to 10 dry weight percent of lung-surfactant polypeptide.

In specific exemplary embodiments, the phospholipid of the surfactant mixture includes dipalmitoyl phosphatidylcholine (DPPC) and palmitoyl, oleoyl phosphatidylglycerol (POPG) in a mole ratio of between 4:1 and 2:1. An exemplary spreading agent is a fatty acid or fatty alcohol having a fatty acyl chain length of at least 10 carbon atoms, such as palmitic acid or cetyl alcohol.

Where the aerosol particles are formed from a liquid suspension, the surfactant formulation may be suspended in aqueous aerosol droplets. Where the particles are in the form of a dry powder, the particles are dehydrated, or substantially dehydrated The aerosol particles can have a mass median aerodynamic diameter in the 1-5 μm size range.

The invention also provides a method for treating pulmonary inflammation in a mammal comprising administering to the mammal a therapeutically effective amount of a composition comprising a protease inhibitor, a lipase inhibitor and an anti-oxidant. While one of skill in the art may choose to administer the composition directly to pulmonary ties (e.g. by bronchoalveolar lavage, liquid bolus drip or intratracheal administration), the composition can also be administered by other routes, for example, via parenteral, oral or intravenous routes of administration. When pulmonary administration is employed, at least one lung surfactant polypeptide is included in the composition.

The pulmonary inflammation treated by the present methods can be associated, for example, with pulmonary hypertension, neonatal pulmonary hypertension, neonatal bronchopulmonary dysplasia, chronic obstructive pulmonary disease, acute bronchitis, chronic bronchitis, emphysema, bronchiolitis, bronchiectasis, radiation pneumonitis, hypersensitivity, pneumonitis, acute inflammatory asthma, acute smoke inhalation, thermal lung injury, allergic asthma, iatrogenic asthma, cystic fibrosis, alveolar proteinosis, alpha-1-protease deficiency, pulmonary inflammatory disorders, pneumonia, acute respiratory distress syndrome, acute lung injury, idiopathic respiratory distress syndrome, or idiopathic pulmonary fibrosis.

In another aspect the invention includes a method of administering an active agent such as a protease inhibitor, a lipase inhibitor or an anti-oxidant to a patient. Administration can be by bronchoalveolar lavage, bolus liquid administration or inhalation The method includes incorporating the agent into a surfactant mixture composed of (i) 50-95 dry weight percent phospholipid, (ii) 2-25 dry weight percent of a spreading agent effective to promote incorporation and distribution of the phospholipid within the surface-lining layer of the lung, and (iii) 0.1 to 10 dry weight percent of lung-surfactant polypeptide. The latter component contains between 10-60 amino acid residues and has an amino acid sequence of alternating hydrophobic and hydrophilic amino acid residue regions represented by the formula $(Z_aU_b)_cZ_d$, where Z is a hydrophilic amino acid residue, U is a hydrophobic amino acid residue, "a" has an average value of 1-5, "b" has an average value of 3-20, "c" is 1-10, and "d" is 0 to 3. The resulting formulation contains 1-80, or 2-50 dry weight percent of the active agent.

The formulation can be converted to a particle composition whose particles have a mass median aerodynamic diameter in the 1-5 μm. The particles are administered in the form of an aerosol composition to the respiratory tract of the patient, in a therapeutically effective amount.

In some embodiments, the formulation is an aqueous formulation for administration by bronchoalveolar lavage to the lungs or by direct bolus administration, for example, through a tracheal tube. In another embodiment, the formulation is prepared by dissolving or suspending the active agents and other components of the formulation in a solvent, which may be an aqueous, organic, or mixed solvent. The formulation can be converted to a particle composition for aerosol administration by spray drying the mixture under conditions effective to produce dry particles having the desired 1-5 μm MMAD size range. In other embodiments, the formulation can be converted to a particle composition for aerosol administration by lyophilizing the liquid composition to dryness, and comminuting the dried mixture to form dry particles of the desired size range.

Liquid (e.g. aqueous) compositions can be administered directly to the lung by bronchoalveolar lavage or bolus administration. Liquid or dry particles can be administered by inhalation in aerosol form. The formulation may also be in an aqueous suspension form, e.g., liposome suspension, which is aerosolized to form liquid droplets having suspended formulation particles suspended therein.

These and other objects and features of the invention will become more fully apparent when the following detailed description of the invention is read in conjunction with the accompanying drawings.

DETAILED DESCRIPTION OF THE INVENTION

Figure 1:
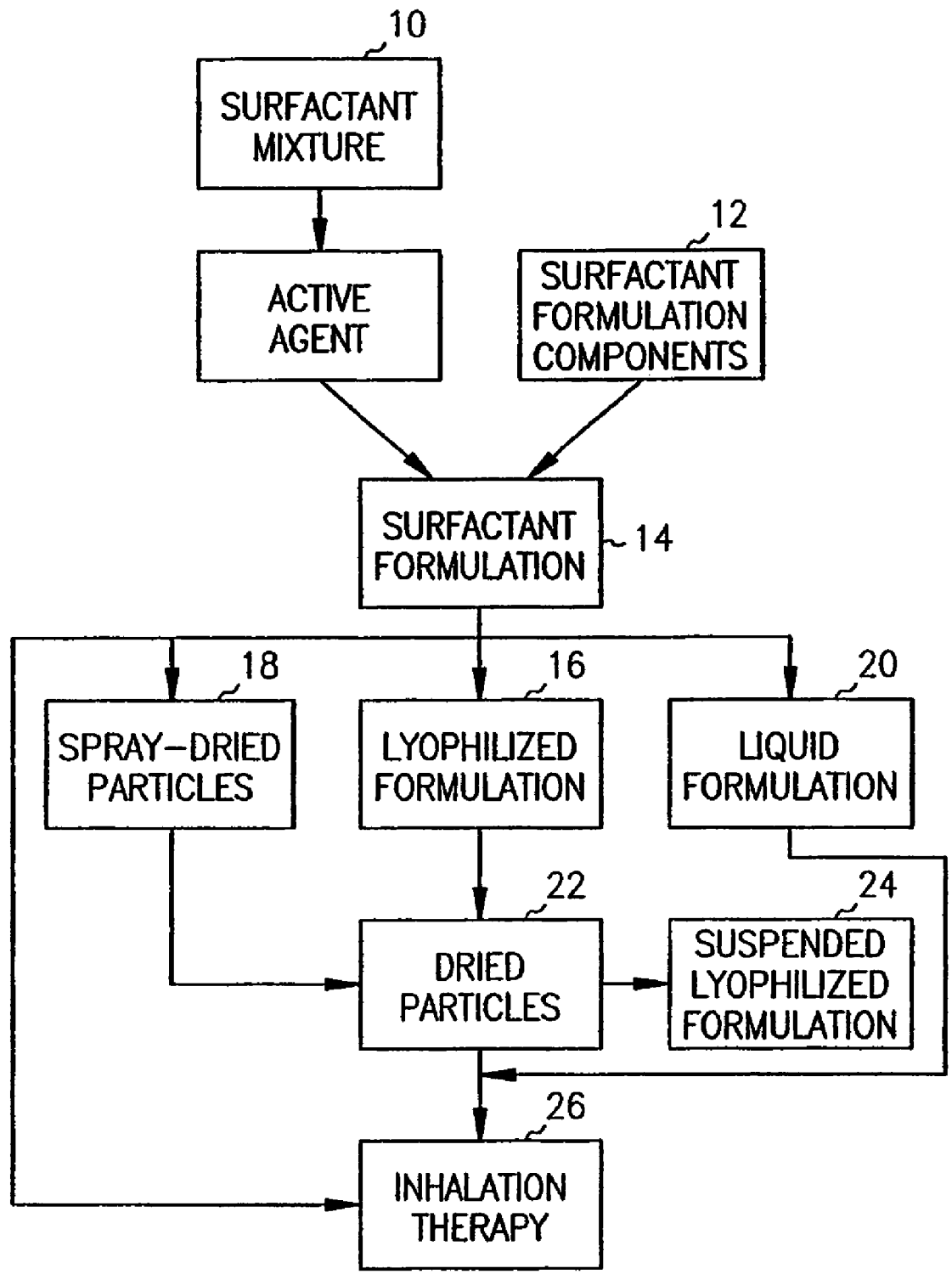
FIG. 1 is a flow diagram illustrating the relationship between various processing steps employed in practicing certain aspects of the invention.

The invention relates to compositions comprising a combination of lung surfactant polypeptide(s) and various inhibitors of the types of tissue destruction processes that occur during inflammation. Other ingredients can be included to facilitate delivery and dispersion of the composition within the lung, for example, phospholipids and spreading agents.

Definitions

The terms below have the following meanings, unless indicated otherwise.

"Amino acid" refers to refers to amino acid residues making up a protein. Amino acids are commonly in the natural L-form; however, D-amino acids, substituted amino acids (e.g., amino acids with modified side chain groups) amino acid metabolites and catabolites, amino acids with "retro" backbones, and amino acid mimics or analogs are also contemplated for use in—and are thus encompassed by—the present invention. In keeping with standard polypeptide nomenclature, *J. Biol. Chem.*, 243:3557-59, 1969, abbreviations for the more common amino acid residues are as shown in the following Table of Correspondence:

| Table of Correspondence | | |
|---|---|---|
| Symbol | | |
| 1-Letter | 3-Letter | Amino Acid |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |
| x | Xaa | Unknown/other |

It should be noted that, unless otherwise indicated, the amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822 (b)(4), and incorporated herein by reference. The phrase "amino acid residue" is also broadly defined to include D-amino acids, substituted amino acids (e.g., amino acids with modified side chain groups), modified amino acids (e.g., amino acid metabolites, catabolites, and amino acids with "designed" side chains), and amino acid mimics or analogs.

Furthermore, it should be noted that a dash at the beginning or end of an amino acid residue sequence generally indicates a bond to a radical such as H and OH (hydrogen and hydroxyl) at the amino- and carboxy-termini, respectively, or a further sequence of one or more amino acid residues. In addition, it should be noted that a virgule (/) at the right hand end of a residue sequence indicates that the sequence is continued on the next line.

"Pharmaceutically acceptable" is a term that refers to molecular entities and compositions that do not produce an allergic or similar untoward reaction when administered to a human.

A "protein" or "polypeptide" or "peptide" is a biopolymer composed of amino acid or amino acid analog subunits, typically some or all of the 20 common L-amino acids found in biological proteins, linked by peptide intersubunit linkages, or other intersubunit linkages that are consistent with enzyme-substrate or receptor binding ligand interactions. The protein has a primary structure represented by its subunit sequence, and may have secondary helical or pleat structures, as well as overall three-dimensional structure. Although "protein" commonly refers to a relatively large polypeptide, e.g., containing 30 or more amino acids, and "peptide" to or "polypeptide" to smaller polypeptides, the terms are also used interchangeably herein. That is, the term "protein" may refer to a larger polypeptide, e.g., greater than 30 amino acids, but does not necessarily exclude a smaller polypeptide, and the term "polypeptide" may refer to a smaller peptide, e.g., fewer than 30 amino acids, but may also include larger proteins.

"Surfactant activity" refers to the ability of any substance, such as an organic molecule, protein or polypeptide—when combined with lipids, either alone or in combination with other organic molecules, to lower surface tension at an air/water interface. The measurement can be made with a Wilhelmy Balance or pulsating bubble surfactometer by an in vitro assay. See, for example that of King et al, *Am. J. Physiol.* 223:715-726 (1972), or the assay illustrated herein, which utilizes a measurement of surface tension at an air-water interface when a protein or polypeptide is admixed with a phospholipid. In addition, in vivo measurements of increases in compliance or airflow at a given pressure of air entering the lung can be readily made, such as in the assay of Robertson, *Lung,* 158:57-68 (1980). In this assay, the sample to be assessed is administered through an endotracheal tube to fetal rabbits or lambs delivered prematurely by Caesarian section. (These "preemies" lack their own pulmonary surfactant, and are supported on a ventilator). Measurements of lung compliance, blood gases and ventilator pressure provide indices of activity. In vitro assays of surfactant activity, which is assessed as the ability to lower the surface tension of a pulsating bubble, and in vivo assays utilizing fetal rabbits, as reported herein, are described in detail by Revak et al, *Am. Rev. Respir. Dis.,* 134:1258-1265 (1986).

"Surfactant molecule" refers to organic molecules having surfactant activities and when admixed with pharmaceutically acceptable lipids form a surfactant that has greater surfactant activity than the lipids alone as evidenced by the lower ΔP values.

"Natural pulmonary surfactant" refers to a pulmonary surfactant (PS) that lines the alveolar epithelium of mature mammalian lungs. Natural or native PS has been described as a "lipoprotein complex" because it contains both phospholipids and apoproteins that interact to reduce surface tension at the lung air-liquid interface. Natural surfactant contains several lipid species of which dipalmitoyl phosphatidylcholine (DPPC) is the major component. At least four proteins are typically present in natural pulmonary surfactants, SP-A, SP-B, SP-C and SP-D. Of these four, SP-B and SP-C are distinct, low molecular weight, relatively hydrophobic proteins that have been shown to enhance the surface-active properties of surfactant phospholipid mixtures, presumably by facilitating transfer of lipids from the bulk phase lamellar organization to the air-water interface and also by stabilizing the lipid monolayer during expiration. The structure of SP-B is unusual in that charged amino acids (predominantly basic) are located at fairly regular intervals within stretches of otherwise hydrophobic residues. For the domain consisting of residues 59-80 of the native SP-B sequence, these charged groups have been shown to be necessary for biological activity. In addition, natural and synthetic peptides, which are modeled on this hydrophobic-hydrophilic domain when combined with DPPC and PG, exhibit good surfactant activity.

Natural surfactant protein is stored in lung epithelial cells in the form of lamellar bodies and, following export, it undergoes a structural transition to form tubular myelin before giving rise to a monolayer at the air-water interface. It has been proposed that surfactant proteins SP-A, SP-B and SP-C may facilitate these structural transitions and stabilize the lipid monolayer during expansion and contraction of the alveolus; however, a complete understanding of lipid-protein interactions at the molecular level is presently lacking.

"Pulmonary administration" refers to any mode of administration that delivers a pharmaceutically active substance to any surface of the lung. The modes of delivery can include, but are not limited to, those suitable for endotracheal administration, i.e., generally as a liquid suspension instigate, as a dry powder "dust" or insufflate, or as an aerosol. Pulmonary administration can be utilized for both local and systemic delivery of pharmaceutically active substances.

"Transport across a pulmonary surface" refers to any mode of passage that penetrates or permeates the exposed surface of the lungs. This includes passage through any lung surfaces, including alveolar surfaces (where gaseous exchange occurs), bronchiolar surfaces and passage between any of these surfaces. Passage can be either directly to the pulmonary tissues for local action or via the pulmonary tissues into the circulatory system for systemic action.

"Phospholipids" refers to amphipathic lipids that are composed of a nonpolar hydrophobic tail, a glycerol or sphingosine moiety, and a polar head. The nonpolar hydrophobic tail is usually a saturated or unsaturated fatty acid group. The polar head has a phosphate group that is often attached to a nitrogen containing base.

"Spreading agent" means a compound that promotes incorporation and distribution of phospholipid(s) within the surface lining layer of the lungs, that is, promotes the spreading of phospholipids at the air/liquid interface at the surface lining layer of the lungs.

"Active agent" refers to a therapeutic or diagnostic compound that is administered to achieve a desired therapeutic or diagnostic result or purpose. Pharmaceutically active agent refers to an agent that is a biologically-active synthetic or natural substance that is useful for treating a medical or veterinary disorder or trauma, preventing a medical or veterinary disorder, or regulating the physiology of a human being or animal. The range of active compounds is considered below.

"Aerodynamic diameter" is defined as the diameter of an equivalent spherical particle of unit density that has the same settling velocity as the characterized particle. That is, regardless of the shape or size of particle, the particle is imagined to be transformed into a sphere of unit density. The diameter of that sphere is the aerodynamic diameter. Thus, particles having aerodynamic diameters in the 1-5 micron size have the same aerodynamic properties as spherical particles of unit density having diameters in the 1-5 micron size range. The aerodynamic properties of particles can be measured experimentally using conventional techniques such as cascade impaction, elutriators or sedimentation cells. Often the measuring technique used is one that most closely resembles the situation in which the aerosol is being employed.

"Mass median aerodynamic diameter" of a collection of particles refers to the median aerodynamic diameter (MMAD) of the mass of the particles. That is, half of the mass of the particles is at or below the MMAD, and half above. The heterodispersity of aerosol particles can be defined by a geometric standard deviation (GSD). If all of the particles are the same size and shape, the GSD is 1. A GSD of 3.5 indicates a highly heterodisperse collection of particles. Preferably aerosol particles of the present invention are formed under conditions that give a GSD of between 1 and 2.5, preferably 1-2.

"Model surfactant mixture" or "Surfaxin®" refers to a surfactant mixture prepared in accordance with the present invention, using the surfactant-mixture components set out in Examples 1 and 2.

Active Agents The surfactant carrier of the present invention can be used to administer a range of active agents for treating pulmonary or conditions. Such conditions include pulmonary hypertension, neonatal pulmonary hypertension, neonatal bronchopulmonary dysplasia, chronic obstructive pulmonary disease (COPD), acute and chronic bronchitis, emphysema, bronchiolitis, bronchiectasis, radiation pneumonitis, hypersensitivity, pneumonitis, acute inflammatory asthma, acute smoke inhalation, thermal lung injury, allergic asthma, iatrogenic asthma, cystic fibrosis, and alveolar proteinosis, alpha-1-protease deficiency, pulmonary inflammatory disorders, pneumonia, acute respiratory distress syndrome, acute lung injury, idiopathic respiratory distress syndrome, and idiopathic pulmonary fibrosis. The active agent can act directly on lung tissue, or on pathogenic organisms within pulmonary tissues.

Therapeutic agents used to treat pulmonary inflammatory diseases include protease inhibitors, anti-oxidants, phospholipase inhibitors, lipase inhibitors and combinations thereof. These agents may be in the form of proteins, peptides, nucleic acids, polysaccharides, carbohydrates, lipids, glycoproteins, and organic and inorganic compounds.

According to the invention, proteases can exacerbate pulmonary tissue injury during inflammation. Such protease activity can be detected in pulmonary tissues or in lavage fluids obtained from patients or animal models of pulmonary inflammation. Heightened levels of basement membrane proteins can be detected in lavage fluids from patients suffering from Acute Respiratory Distress Syndrome and in animal models suffering pulmonary injury. The types of proteases that are active in inflamed pulmonary tissues can be identified by procedures available in the art, including detection of specific protease activities, detection of antigenic proteases using protease-specific antibodies, detection of the products of protease activity and the like.

The activity of proteases can be regulated and controlled by inhibitors. Protease inhibitors can regulate the proteolytic activity of target proteases by occupying the active site of the proteases and thereby preventing occupation by normal substrates. Although protease inhibitors fall into several unrelated structure classes, in many embodiments the inhibitors can possess an exposed loop (variously termed an "inhibitor loop," a "reactive core," a "reactive site," or a "binding loop"), which is stabilized by intermolecular interactions between residues flanking the loop and the protein core (Bode and Huber, Eur. J. Biochem. 204:433 (1992)). Interaction between inhibitor and enzyme can produce a stable complex, which disassociates very slowly, releasing either uncleaved inhibitor, or a modified inhibitor that is cleaved at the scissile bond of the binding loop.

The invention contemplates use of any available protease inhibitor in the compositions and methods of the invention One family of protease inhibitors, the Kunitz inhibitors, includes inhibitors of trypsin, chymotrypsin, elastase, kallikrein, plasmin, coagulation factors XIa and IXa, and cathepsin G. Those of skill in the art recognize serine proteases as another family of proteases. Serine proteases include such enzymes as elastase (e.g. human leukocyte elastase), cathepsin G, plasmin, C-1 esterase, C-3 convertase, urokinase, plasminogen activator, acrosin, chymotrypsin, trypsin, thrombin, factor Xa and kallikreins. Another family of inhibitors includes inhibitors of metalloproteinases such as any of metalloproteinases 1-13.

Protease inhibitors that can be used in the compositions and methods of the invention therefore include, for example, the Kunitz inhibitors, matrix metalloproteinase inhibitors and serine protease inhibitors.

Protease inhibitors comprising one or more Kunitz domains include tissue factor pathway inhibitor (TFPI), tissue factor pathway inhibitor 2 (TFPI-2), amyloid β-protein precursor (AβPP), aprotinin, and placental bikunin TFPL an extrinsic pathway inhibitor and a natural anticoagulant, contains three tandemly linked Kunitz inhibitor domains. The aminoterminal Kunitz domain inhibits factor VIIa, plasmin, and cathepsin G; the second domain inhibits factor Xa, trypsin, and chymotrypsin; and the third domain has no known activity (Petersen et al., Eur. J. Biochem. 125:310 (1996)). TFPI-2 has been shown to be an inhibitor of the amidolytic and proteolytic activities of human factor VIIa-tissue factor complex, factor XIa, plasma kallikrein, and plasmin (Sprecher et al., Proc. Nat'l Acad. Sci. USA 91:3353 (1994); Petersen et al., Biochem. 35:266 (1996)).

Aprotinin (bovine pancreatic trypsin inhibitor) is a broad spectrum Kunitz-type serine proteinase inhibitor that has been shown to prevent activation of the clotting cascade. Davis and Whittington, Drugs 49:954 (1995); Dietrich et al., Thorac. Cardiovasc. Surg. 37:92 (1989); Westaby, Ann. Thorac. Surg. 55:1033 (1993); Wachtfogel et al., J. Thorac. Cardiovasc. Surg. 106:1 (1993)). Aprotinin can inhibit plasma kallikrein or plasmin (Dennis et al., J. Biol. Chem. 270:25411 (1995)). Placental bikunin is a serine proteinase inhibitor containing two Kunitz domains (Delaria et al., J. Biol. Chem. 272:12209 (1997)). Individual Kunitz domains of bikunin have been expressed and shown to be potent inhibitors of trypsin, chymotrypsin, plasmin, factor XIa, and tissue and plasma kalikrein (Delaria et al., J. Biol. Chem. 272:12209 (1997)).

Specific examples of elastase inhibitors that can be used in the invention include, for example, human leukocyte elastase inhibitor, elafin and alpha 1-proteinase inhibitor. Other suitable protease inhibitors include human secretory leukocyte protease inhibitor, alpha1-antitrypsin, alpha-1-antichymotrypsin, C-reactive protein and combinations thereof.

Nucleic acid and amino acid sequences for these protease inhibitors can be found in the art, for example, in the NCBI database. See website at ncbi.nlm.nih.gov. For example, one amino acid sequence for human leukocyte elastase inhibitor can be found in the NCBI database as accession number P30740 (gi: 266344). See website at ncbi.nlm.nih.gov. This sequence is provided below as follows (SEQ ID NO:14).

```
  1 MEQLSSANTR FALDLFLALS ENNPAGNIFI SPFSISSAMA

41 MVFLGTRGNT AAQLSKTFHF NTVEEVHSRF QSLNADINKR

81 GASYILKLAN RLYGEKTYNF LPEFLVSTQK TYGADLASVD

121 FQHASEDARK TINQWVKGQT EGKIPELLAS GMVDNMTKLV

161 LVNAIYFKGN WKDKFMKEAT TNAPFRLNKK DRKTVKMMYQ

201 KKKFAYGYIE DLKCRVLELP YQGEELSMVI LLPDDIEDES

241 TGLKKIEEQL TLEKLHEWTK PENLDFIEVN VSLPRFKLEE

281 SYTLNSDLAR LGVQDLFNSS KADLSGMSGA RDIFISKIVH

321 KSFVEVNEEG TEAAAATAGI ATFCMLMPEE NFTADHPFLF

361 FIRHNSSGSI LFLGRFSSP
```

An amino acid sequence for human alpha-1-antitrypsin can be found in the NCBI database as accession number P01009 (gi: 1703025). See website at ncbi.nlm.nih.gov. This sequence is provided below as follows (SEQ ID NO:15).

```
  1 MPSSVSWGIL LLAGLCCLVP VSLAEDPQGD AAQKTDTSHH

41 DQDHPTFNKI TPNLAEFAFS LYRQLAHQSN STNIFFSPVS

81 IATAFAMLSL GTKADTHDEI LEGLNFNLTE IPEAQIHEGF

121 QELLRTLNQP DSQLQLTTGN GLFLSEGLKL VDKFLEDVKK

161 LYHSEAFTVN FGDTEEAKKQ INDYVEKGTQ GKIVDLVKEL

201 DRDTVFALVN YIFFKGKWER PFEVKDTEEE DFHYDQVTTV

241 KVPMMKRLGM FNIQHCKKLS SWVLLMKYLG NATAIFFLPD

281 EGKLQHLENE LTHDIITKFL ENEDRRSASL HLPKLSITGT

321 YDLKSVLGQL GITKVFSNGA DLSGVTEEAP LKLSKAVHKA

361 VLTIDEKGTE AAGAMFLEAI PMSIPPEVKF NKPFVFLMIE

401 QNTKSPLFMG KVVNPTQK
```

An amino acid sequence for human bikunin can be found in the NCBI database as accession number NP 066925 (gi: 10863909). See website at ncbi.nlm.nih.gov. This sequence is provided below as follows (SEQ ID NO:16).

```
  1 MAQLCGLRRS RAFLALLGSL LLSGVLAADR ERSIHDFCLV

41 SKVVGRCRAS MPRWWYNVTD GSCQLFVYGG CDGNSNNYLT

81 KEECLKKCAT VTENATGDLA TSRNAADSSV PSAPRRQDSE

121 DHSSDMFNYE EYCTANAVTG PCRASFPRWY FDVERNSCNN

161 FIYGGCRGNK NSYRSEEACM LRCFRQQENP PLPLGSKVVV

201 LAGLFVMVLI LFLGASMVYL IRVARRNQER ALRTVWSSGD

241 DKEQLVKNTY VL
```

An amino acid sequence for a human elafin can be found in the NCBI database as accession number 1FLEI (gi: 1942680). See website at ncbi.nlm.nih.gov. This sequence is provided below as follows (SEQ ID NO:17).

```
  1 AQEPVKGPVS TKPGSCPIIL IRCAMLNPPN RCLKDTDCPG

41 IKKCCEGSCG MACFVPQ
```

Many amino acid sequences related to such a human elafin can also be found in the NCBI database. For example, human protease inhibitor 3 (skin derived) is related to elafin and has accession number NP 002629 (gi: 4505787). See website at ncbi.nlm.nih.gov. This sequence for human protease inhibitor 3 is provided below as follows (SEQ ID NO:18).

```
  1 MRASSFLIVV VFLIAGTLVL EAAVTGVPVK GQDTVKGRVP

41 FNGQDPVKGQ VSVKGQDKVK AQEPVKGPVS TKPGSCPIIL

81 IRCAMLNPPN RCLKDTDCPG IKKCCEGSCG MACFVPQ
```

Another example of an inhibitor with a sequence similar to human elafin is bovine bTrappin-2, with accession number CAA11184 (gi: 2764786). See website at ncbi.nlm.nih.gov. This sequence for bovine bTrappin-2 is provided below (SEQ ID NO:19).

```
  1 QEPVKGQDPV KGQDPVKGQD PVKGQDPVKD QNPVRGQEPV

41 KGQDPVKGQD PVKGQDPVKG QEPVKGQDPV KGQDPVKRQG

81 RIGGPLLTKP GSCPRVLIRC AMMNPPNRCL RDAQCPGVKK

121 CCEGSCGKTC MDPQ
```

The invention also contemplates use of inhibitors of metalloproteinases in the compositions and methods. Many human metalloproteinases exist. The invention contemplates use of any inhibitor of a human metalloproteinase. For example, inhibitors such as tissue inhibitors of metalloproteinases (TIMPs) can be utilized in the invention. A sequence for a human TIMP-1 can be found in the NCBI database as accession number P01033 (gi: 135850). See website at ncbi.nlm.nih.gov. This sequence for human TIMP-1 is provided below (SEQ ID NO:20).

```
  1 MAPFEPLASG ILLLLWLIAP SRACTCVPPH PQTAFCNSDL

41 VIRAKFVGTP EVNQTTLYQR YEIKMTKMYK GFQALGDAAD

81 IRFVYTPAME SVCGYFHRSH NRSEEFLIAG KLQDGLLHIT

121 TCSFVAPWNS LSLAQRRGFT KTYTVGCEEC TVFPCLSIPC

161 KLQSGTHCLW TDQLLQGSEK GFQSRHLACL PREPGLCTWQ

201 SLRSQIA
```

A sequence for a human TIMP-2 can be found in the NCBI database as accession number NP 003246 (gi:4507511). See website at ncbi.nlm.nih.gov. This sequence for human TIMP-2 is provided below (SEQ ID NO:21).

```
  1 MGAAARTLRL ALGLLLLATL LRPADACSCS PVHPQQAFCN

41 ADVVIRAKAV SEKEVDSGND IYGNPIKRIQ YEIKQIKMFK

81 GPEKDIEFIY TAPSSAVCGV SLDVGGKKEY LIAGKAEGDG

121 KMHITLCDFI VPWDTLSTTQ KKSLNHRYQM GCECKITRCP

161 MIPCYISSPD ECLWMDWVTE KNINGHQAKF FACIKRSDGS

201 CAWYRGAAPP KQEFLDIEDP
```

A sequence for a human TIMP 3 can be found in the NCBI database at accession number NP 000353 (gi: 4507513). See website at ncbi.nlm.nih.gov. This sequence for human TIMP 3 is provided below (SEQ ID NO:22).

```
  1 MTPWLGLIVL LGSWSLGDWG AEACTCSPSH PQDAFCNSDI

41 VIRAKVVGKK LVKEGPFGTL VYTIKQMKMY RGFTKMPHVQ

81 YIHTEASESL CGLKLEVNKY QYLLTGRVYD GKMYTGLCNF

121 VERWDQLTLS QRKGLNYRYH LGCNCKIKSC YYLPCFVTSK

161 NECLWTDMLS NFGYPGYQSK HYACIRQKGG YCSWYRGWAP

201 PDKSIINATD P
```

Sequences for other human TIMPs are also publicly available. See website at ncbi.nlm.nih.gov. An amino acid sequence for a human secretory leukocyte protease inhibitor can also be found in the NCBI database as accession number NP003055 (gi: 4507065). See website at ncbi.nlm.nih.gov. This sequence is provided below as follows (SEQ ID NO:23).

```
  1 MKSSGLFPFL VLLALGTLAP WAVEGSGKSF KAGVCPPKKS
 41 AQCLRYKKPE CQSDWQCPGK KRCCPDTCGI KCLDPVDTPN
 81 PTRRKPGKCP VTYGQCLMLN PPNFCEMDGQ CKRDLKCCMG
121 MCGKSCVSPV KA
```

Hence, the invention provides a variety of protease inhibitors that can be utilized in the compositions and methods of the invention.

Phospholipase enzymes catalyze the removal of fatty acid residues from phosphoglycerides. Specifically, phospholipase A2 (PLA2) cleaves the ester bond at the 2 position of the glycerol moiety of membrane phospholipids giving rise to equimolar amounts of arachidonic acid and lysophospholipids. Although PLA2 preferentially cleaves arachidonic acid from phospholipids, arachidonic acid is generated secondarily from intermediates of the S1, phospholipase C- and phospholipase D-activated pathways. PLA2 inhibitors include chemical molecules such as p-bromophenacyl bromide. Other PLA2 inhibitors include biological molecules such as thielocin A1 beta, produced by a fungus (Tanaka et al. (1995) Eur J Pharmacol 279:143-8), or lipocortin or annexin I (NCBI accession number gi:71756; Wallner et al., Cloning and expression of human lipocortin, a phospholipase A2 inhibitor with potential anti-inflammatory activity, Nature 320 (6057), 77-81 (1986)), or Crotalus phospholipase A2 inhibitor (CNF) (NCBI accession number gi: 501050; Fortes-Dias C L et al. 1994; J Biol Chem 269:15646-51). Nonspecific PLA2 inhibitors such as glucocorticoids can also be used. Phospholipase $A_2$ inhibitors suitable for use in the invention also include LY11-727 (Eli Lilly).

Fortes-Dias C L et al. (1994; J Biol Chem 269:15646-51) have isolated and characterized a PLA2 inhibitor from the plasma of a South American rattlesnake, *Crotalus durissus terificus*. This 20-24 kDa protein, designated Crotalus neutralizing factor (CNF), appears to self-associate as a 6-8 oligomeric aggregate. The crotoxin molecule that CNF neutralizes is active only as a dimer and consists of an acidic molecule (CA) associated with one of two basic isoforms of PLA2 (CB1 and CB2). CNF actually displaces CA to form a stable association with one of the CB molecules. This displacement inactivates the neurotoxic, cardiotoxic, myotoxic, anticoagulent and platelet-activating activities of crotoxin.

The full length 840 bp cDNA of CNF was cloned from Crotalus liver tissue. The nucleotide sequence encodes a 19 residue signal peptide and a 181 residue mature protein with 16 cysteines, a pI of 5.45, and a possible glycosylation site at N157. Fortes-Dias states that the cDNA contains non-coding sequence and lacks a putative polyadenylation site. In inhibitory assays, the acidic CNF molecule also inhibits the activity of bee venom, and in 100-fold excess in plasma, porcine pancreatic PLA2.

In addition to protease inhibitors and lipase inhibitors, the compositions and methods or the invention can employ anti-oxidants. Inflammation can stimulate polymorphonuclear leukocytes and macrophages that produce large amounts of superoxide ($O_2.^-$) and hydrogen peroxide ($H_2O_2$) (Babior, B. M. et al. [1973] J Clin Invest 52:741-744; Halliwell, B. et al. [1999] Free radicals in Biology and Medicine. Oxford N.Y.: Clarendon Press, Oxford University Press). The detrimental effects of these radicals may be amplified in the presence of iron and the subsequent formation of other reactive intermediates, such as the hydroxyl radical (OH.).

NADPH oxidase, a membrane-associated electron transport chain protein, becomes activated during inflammation and directly reduces $O_2$ to $O_2.^-$. Superoxide can then be dismutated by superoxide dismutase to produce $H_2O_2$. Superoxide can reduce transition metals, including ferric iron ($Fe^{3+}$), to ferrous iron ($Fe^{2+}$). The reduced metal ion can then react with $H_2O_2$ to generate the highly oxidizing OH. radical species. The hydroxyl radical has been widely postulated to cause significant damage to several biomolecules in vivo.

Biomolecules that can be damaged by such oxidizing species include DNA, proteins and membrane lipids. DNA that becomes oxidized can become fragmented. Oxidized proteins and membrane lipids can have diminished or altered functions and may become targeted for destruction. The presence of oxidized products and the effects of oxidation on pulmonary tissues can be detected by examination of lavage fluids or by collection of lung tissues. For example, lung tissues from control and LPS-injured model animals can be collected and tested for such oxidized products. As described herein, model animals (e.g. rabbits) can be given bacterial lipopolysaccharide (LPS) intratracheally to provoke and simulate pulmonary inflammation.

Lavage fluids and lung tissues from such LPS-treated model animals that have been collected can be analyzed in a variety of ways. For example, DNA damage can be assessed by labeling the ends of DNA molecules in tissue samples or DNA isolates. Fragmented DNA is then observed by detecting whether significant label is present in cellular nuclei of tissue sections and whether labeled, low molecular weight bands are detected after electrophoretic separation of labeled DNA isolated from lung tissues. The presence of such low molecular DNA bands indicates that the DNA has become fragmented. The size of the bands is assessed by comparison to DNA markers of known molecular weight.

Other biological marker(s) of oxidation can be monitored including, for example, free iron, total antioxidant status, 8-isoprostane (8-Iso-PGF$_2\alpha$), superoxide dismutase (SOD), glutathione peroxidase (GPX), glutathione levels, lactate dehydrogenase (LDH), C-reactive protein, lipid hydroperoxidase (LOOH), myeloperoxidase, interleukin-6 (IL-6), creatine kinase (CK), dityrosine, and 8-hydroxyguanine, or combinations thereof. Unsaturated phospholipids in pulmonary membranes can undergo peroxidative changes upon exposure to $H_2O_2$ as determined by the appearance of lysophospholipids, fatty acid scission fragments of acyl side chains in reverse-phase BPLC, by the development of thiobarbituric acid (TBA)-binding material and by the generation of conjugated dienes. Hence, the presence of lysophospholipids, thiobarbituric acid-binding materials, conjugated dienes and the like, in lavage fluids can be used as an indicator of oxidized lipids.

To reduce the effects of oxidation upon pulmonary tissues, anti-oxidants can be incorporated into the compositions and methods of the invention. Suitable anti-oxidants include catalase, glutathione, N-acetylcysteine, procysteine, rosemary leaf extract, alpha-tocopherol, 2,4-diaminopyrrolo-[2,3-d] pyrimidine, ascorbic acid and carotenoid compounds such as leutein, zeaxanthin, cryptoxanthin, violaxanthin, carotene diol, hydroxycarotene, hydroxylycopene, alloxanthin and dehydrocryptoxanthin, including derivatives thereof. For example, ester derivatives of ascorbic acid and of carotenoid compounds such as lutein, zeaxanthin, cryptoxanthin, violaxanthin, carotene diol, hydroxycarotene, hydroxylycopene, alloxanthin and dehydrocryptoxanthin can be used in the invention.

The protease inhibitors, lipase inhibitors and anti-oxidants can be administered by any available route, including parenteral, pulmonary, intravenous, intradermal, subcutaneous, oral, inhalation, transdermal (topical), transmucosal, subdermal, subcutaneous, tmmsdermal, or rectal routes. In some embodiments, the active agents of the invention are administered by pulmonary delivery, however, intravenous delivery coupled with pulmonary delivery of the active agents can augment the beneficial effects of the present compositions.

Other compounds can be included in the compositions of the invention, including those compatible with or suitable for treating pulmonary conditions. Agents that can be co-administered include anti-allergenic agents, anti-inflammatory agents, anti-microbials including anti-bacterials, anti-fungals, and anti-virals, antibiotics, immunomodulators, hematopoietics, xanthines, sympathomimetic amines, mucolytics, corticosteroids, anti-histamines, and vitamins. Other examples include bronchodilators, such as albuterol, xopenex, terbutaline, salmeterol, formoterol, and pharmacologically acceptable salts thereof, anticholinergics, such as ipratropium bromide, the so-called "mast cell stabilizers", such as cromolyn sodium and nedocromil corticosteroids, such as flunisolide, fluticasone, beclomethasone, budesonide, triamcinolone, and salts thereof, interferons such as INF-alpha, beta and gamma, mucolytics, such as N-acetylcysteine and guaifenesin, leukotriene antagonists, such as zafirlukast and montelukast, phosphodiesterase IV inhibitors, antibiotics, such as amikacin, gentamycin, colistin, protegrins, defensins and tobramycin, antiviral agents, such as ribavirin, RSV monoclonal antibody, VP 14637, antitubercular agents, such as isoniazid, rifampin, and ethambutol, and antifungal agents, such as amphoterecin B.

Lung Surfactant Polypeptides

The surfactant polypeptides are polypeptides that include amino acid residue sequences having alternating charged and uncharged amino acid residue regions. Polypeptides including amino acid residue sequences having alternating hydrophobic and hydrophilic amino acid residue regions are also preferred according to the present invention. Particularly preferred surfactant polypeptides within these groupings are further characterized as having at least about 4, more preferably at least about 8, and even more preferably at least about 10, amino acid residues, and are generally not more than about 60 amino acid residues in length, although longer and even full-length native lung surfactant proteins are also contemplated.

Preferably, surfactant polypeptides of the present invention are constituted by alternating groupings of charged amino acid residues and uncharged amino acid residues as represented by the formula $[(\text{Charged})_a (\text{Uncharged})_b]_c (\text{Charged})_d$, wherein "a" has an average value of about 1 to about 5; "b" has an average value of about 3 to about 20; "c" is 1 to 10; and "d" is 0 to 3. Organic surfactant molecules not comprised solely of amino acid residues alone preferably have a similar structure constituted by alternating groupings of charged and uncharged (or hydrophilic/hydrophobic) constituent molecules.

As known to one of skill in the art, amino acids can be placed into different classes depending primarily upon the chemical and physical properties of the amino acid side chain. For example, some amino acids are generally considered to be charged, hydrophilic or polar amino acids and others are considered to be uncharged, hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include alanine, leucine, isoleucine, methionine, phenylalaine, tryptophan, tyrosine and valine. In some embodiments, cysteine is a nonpolar amino acid. Examples of non-genetically encoded nonpolar amino acids include t-BuA, Cha, norleucine, and/or an aminoaliphatic carboxylic acid, such as α-aminobutanoic acid, α-aminopentanoic acid, α-amino-2-methylpropanoic acid, or α-aminohexanoic acid.

"Aromatic Amino Acid" refers to a nonpolar amino acid having a side chain containing at least one ring having a conjugated r-electron system (aromatic group). The aromatic group may be further substituted with substituent, groups such as alkyl alkenyl, alkynyl, hydroxyl, sulfonyl, nitro and amino groups, as well as others. Examples of genetically encoded aromatic amino acids include phenylalamine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar, uncharged amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, glutamine, lysine and serine. In some embodiments, cysteine is a polar amino acid. Examples of non-genetically encoded polar amino acids include citrulline, homocysteine, N-acetyl lysine and methionine sufoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Ionizable Amino Acid" or "Charged Amino Acid" refers to an amino acid that can be charged at a physiological pH. Such ionizable or charges amino acids include acidic and basic amino acids, for example, D-aspartic acid, D-glutamic acid, D-histidine, D-arginine, D-lysine, D-hydroxylysine, D-ornithine, D-3-hydroxyproline, L-aspartic acid, L-glutamic acid, L-histidine, L-arginine, L-lysine, L-hydroxylysine, L-ornithine or L-3-hydroxyproline.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

The classifications of the above-described genetically encoded and non-encoded amino are for illustrative purposes only and do not purport to be an exhaustive list of amino acid residues that may comprise the lung surfactant polypeptides described herein. Other amino acid residues that are useful for making the lung surfactant polypeptides described herein can be found, e.g., in Fasman, 1989, CRC Practical Handbook of Biochemistry and Molecular Biology, CRC Press, Inc., and the references cited therein. Another source of amino acid residues is provided by the website of RSP Amino Acids Analogues, Inc. (www.amino-acids.com). Amino acids not specifically mentioned herein can be conveniently classified into the above-described categories on the basis of known behavior and/or their characteristic chemical and/or physical properties as compared with amino acids specifically identified.

In some embodiments, surfactant polypeptides include a sequence having alternating groupings of amino acid residues as represented by the formula $(Z_aU_b)_cZ_d$, wherein Z is a charged amino acid and U is an uncharged amino acid; "a" has an average value of about 1 to about 5; "b" has an average value of about. 3 to about 20, "c" is 1 to 10; and "d" is 0 to 3.

In some embodiments, Z is histidine, lysine, arginine, aspartic acid, glutamic acid, 5-hydroxylysine, 4-hydroxyproline, and/or 3-hydroxyproline, and U is valine, isoleucine, leucine, cysteine, tyrosine, phenylalanine, and/or an α-aminoaliphatic carboxylic acid, such as α-aminobutanoic acid, α-aminopentanoic acid, c-amino-2-methylpropanoic acid, or α-aminohexanoic acid.

In another embodiment, preferred polypeptides of the present invention have alternating groupings or amino acids residue regions as represented by the formula $(B_aU_b)_cB_d$, wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline; "a" has an average value of about 1 to about 5; "b" has an average value of about 3 to about 20; "c" is 1 to 10; and "d" is 0 to 3.

In still another embodiment, surfactant polypeptides of the present invention include a sequence having alternating groupings of amino acid residues as represented by the formula $(B_aJ_b)_cB_d$, wherein B is an amino acid residue independently selected from the group) consisting of histidine, 5-hydroxylysine, 4-hydroxyproline, and 3-hydroxyproline; and J is an α-aminoaliphatic carboxylic acid; "a" has an average value of about 1 to about 5; "b" has an average value of about 3 to about 20; "c" is 1 to 10; and "d" is 0 to 3.

In various embodiments including "J" in the relevant formula, J is an α-aminoaliphatic carboxylic acid having four to six carbons, inclusive. In other preferred variations, J is an α-aminoaliphatic carboxylic acid having six or more carbons, inclusive. In yet other variations, J is preferably selected from the group consisting of α-aminobutanoic acid, α-aminopentanoic acid, α-amino-2-methylpropanoic acid, and α-aminohexanoic acid.

Another embodiment contains surfactant polypeptides including a sequence having alternating groupings of amino acid residues as represented by the formula $(Z_aU_b)_cZ_d$, wherein Z is an amino acid residue independently selected from the group consisting of R, D, E, and K; and U is an amino acid residue independently selected from the group consisting of V, I, L, C, Y and F; from the group consisting of V, I, L, C and F; or from the group consisting of L and C; "a" has an average value of about 1 to about 5; "b" has an average value of about 3 to about 20; "c" is 1 to 10; and "d" is 0 to 3.

In the foregoing formulae, Z and U, Z and J, D and U, and B and J are amino acid residues that, at each occurrence, are independently selected. In addition, in each of the aforementioned formulae, "a" generally has an average value of about 1 to about 5; "b" generally has an average value of about 3 to about 20; "c" is 1 to 10; and "d" is 0 to 3.

In one variation of the foregoing embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (δ-hydroxylysine), 4-hydroxyproline, and 3-hydroxyproline.

In various disclosed embodiments, U and J are, preferably, uncharged amino acid residues. In another preferred embodiment, U and J are hydrophobic amino acid residues. In one embodiment, U is preferably selected from the group consisting of V, L , C, Y, and F. In another preferred embodiment, U is selected from the group consisting of V, I, L, C, and F. In yet another preferred embodiment, U is selected from the group consisting of L and C. In various preferred embodiments, U is L.

Similarly, in various embodiments, B is an amino acid preferably selected from the group consisting of H, 5-hydroxylysine, 4-hydroxyproline, and 3-hydroxyproline. Alternatively, B may be selected from the group consisting of collagen-derived amino acids, which includes 5-hydroxylysine, 4-hydroxyproline, and 3-hydroxyproline.

In another embodiment of the present invention, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In preferred embodiments of the present invention, items "a", "b", "c" and "d" are numbers that indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4-8. In one preferred embodiment, "b" is about 4.

In various embodiments, "c" is 1 to 10, preferably 2 to 10, more preferably in the range of 3-8 or 4-8, and even more preferably 3 to 6. In one preferred embodiment, "c" is about. 4.

In various embodiments, "d" is 0 to 3 or 1 to 3. In one preferred embodiment, "d" is 0 to 2 or 1 to 2; in another preferred embodiment, "d" is 1.

By stating that an amino acid residue—e.g., a residue represented by Z or U—is independently selected, it is meant that at each occurrence, a residue from the specified group is selected. That is, when "a" is 2, f or example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence (e.g., $Z_aU_b$) can vary somewhat within the peptide sequence, the average values of "a" and "b" would be about 1 to about 5 and about 3 to about 20, respectively.

For example, using the formula $(Z_aU_b)_cZ_d$ for the peptide designated "KL8" in Table 1 below, the formula can be rewritten as $K_1L_8K_1L_8K_1L_2$, wherein the average value of "b" is six [ie., (8+8+2)/3=6], "c" is three and "d" is zero. Exemplary preferred polypeptides of the above formula are shown in Table 1 below:

TABLE 1

| Designation[1] | SEQ ID NO | Amino Acid Residue Sequence |
|---|---|---|
| KL4 | 1 | KLLLLKLLLLKLLLLKLLLLK |
| KL8 | 2 | KLLLLLLLLLLLLLLLLLKLL |
| KL7 | 3 | KKLLLLLLLKKLLLLLLLKKL |
| DL4 | 4 | DLLLLDLLLLDLLLLDLLLLD |
| RL4 | 5 | RLLLLRLLLLRLLLLRLLLLR |
| RL8 | 6 | RLLLLLLLLRLLLLLLLLRLL |
| RL7 | 7 | RRLLLLLLLRRLLLLLLLRRL |
| RCL1 | 8 | RLLLLCLLLRLLLLCLLLR |
| RCL2 | 9 | RLLLLCLLLRLLLLCLLLRLL |
| RCL3 | 10 | RLLLLCLLLRLLLLCLLLRLLLLCLLLR |
| HL4 | 13 | HLLLLHLLLLHLLLLHLLLLH |

[1]The designation is an abbreviation for the indicated amino acid residue sequence.

Also suitable are composite polypeptides of about 4 to 60 amino acid residues having a configuration that maximizes their interaction with the alveoli. A composite polypeptide consists essentially of an amino terminal sequence and a carboxy terminal sequence. The amino terminal sequence has an amino acid sequence of a hydrophobic region polypeptide or a hydrophobic peptide of this invention, preferably hydrophobic polypeptide, as defined in the above formula The carboxy terminal sequence has the amino acid residue sequence of a subject carboxy terminal peptide.

Proteins and polypeptides derived from or having characteristics similar to those of natural Surfactant Protein (SP) are useful in the present methods. As noted, SP isolated from any mammalian species may be utilized, although bovine, porcine and human surfactants are particularly preferred.

Natural surfactant proteins include SP-A, SP-B, SP-C or SP-D, or fragments thereof, alone or in combination with lipids. A preferred fragment is the aminoterminal residues 1-25 of SP-B.

Many amino acid sequences related to such natural surfactant proteins can be found in the NCBI database. For example, a sequence of human pulmonary surfactant associated protein A1 can be found in the NCBI database as accession number NP 005402 (gi: 13346504). See website at ncbi.nlm.nih.gov. This sequence for human SP-A1 is provided below as follows (SEQ ID NO:25).

```
  1 MWLCPLALNL ILMAASGAVC EVKDVCVGSP GIPGTPGSHG
 41 LPGRHGRDGL KGDLGPPGPM GPPGEMPCPP GNDGLPGAPG
 81 IPGECGEKGE PGERGPPGLR AHLDEELQAT LHDFRHQILQ
121 TRGALSLQGS IMTVGEKVFS SNGQSITFDA IQEACARAGG
161 RIAVPRNPEE NEAIASFVKK YNTYAYYGLT EGPSPGDFRY
201 SDGTPVNYTN WYRGEPAGRG KEQCVEMYTD GQWNDRNCLY
241 SRLTICEF
```

An amino acid sequence for human pulmonary surfactant associated protein A2 can be found in the NCBI database as accession number NP 008857 (gi: 13346506). See website at ncbi.nlm.nih.gov. This sequence for human SP-A2 is provided below as follows (SEQ ID NO:26).

```
  1 MWLCPLALNL ILMAASGAAC EVKDVCVGSP GIPGTPGSHG
 41 LPGRDGRDGV KGDPGPPGPM GPPGETPCPP GNNGLPGAPG
 81 VPGERGEKGE AGERGPPGLP AHLDEELQAT LHDFRHQILQ
121 TRGALSLQGS IMTVGEKVFS SNGQSITFDA IQEACARAGG
161 RIAVPRNPEE NEAIASFVKK YNTYAYVGLT EGPSPGDFRY
201 SDGTPVNYTN WYRGEPAGRG KEQCVEMYTD GQWNDRNCLY
241 SRLTICDF
```

An amino acid sequence for human pulmonary surfactant associated protein B can be found in the NCBI database as accession number NP 000533 (gi: 4506905). See website at ncbi.nhn.nih.gov. This sequence for human SP-B is provided below as follows (SEQ ID NO:27).

```
  1 MAESHLLQWL LLLLPTLCGP GTAAWTTSSL ACAQGPEFWC
 41 QSLEQALQCR ALGHCLQEVW GHVGADDLCQ ECEDIVHILN
 81 KMAKEAIFQD TMRKFLEQEC NVLPLKLLMP QCNQVLDDYF
121 PLVIDYFQNQ IDSNGICMHL GLCKSRQPEP EQEPGMSDPL
161 PKPLRDPLPD PLLDKLVLPV LPGALQARPG PHTQDLSEQQ
201 FPIPLPYCWL CRALIKRIQA MIPKGALRVA VAQVCRVVPL
241 VAGGICQCLA ERYSVILLDT LLGRMLPQLV CRLVLRCSMD
281 DSAGPRSPTG EWLPRDSECH LCMSVTTQAG NSSEQAIPQA
```

-continued

```
321 MLQACVGSWL DREKCKQFVE QHTPQLLTLV PRGWDAHTTC

361 QALGVCGTMS SPLQCIHSPD L
```

In addition, human SP18 (SP-B) surfactant protein may be utilized as described herein. See, e.g., U.S. Pat. Nos. 5,407, 914; 5,260,273; and 5,164,369, the disclosures of which are incorporated by reference herein.

An amino acid sequence for human pullnonary surfactant associated protein C can be found in the NCBI database as accession number P11686 (gi: 131425). See website at ncbi.nlm.nih.gov. This sequence for human SP-C is provided below as follows (SEQ ID NO:28).

```
  1 MDVGSKEVTM ESPPDYSAAP RGRFGIPCCP VHLKRLLIVV

41 VVVVLIVVVI VGALLMGLHM SQKHTEMVLE MSIGAPEAQQ

81 RLALSEHLVT TATFSIGSTG LVVYDYQQLL IAYKPAPGTC

121 CYIMKIAPES IPSLEALNRK VHNFQMECSL QAKPAVPTSK

161 LGQAEGRDAG SAPSGGDPAF LGMAVNTLCG EVPLYYI
```

An amino acid sequence for human pulmonary surfactant associated protein D can be found in the NCBI database as accession number P50404 (gi: 1709879). See website at ncbi.nlnih.gov. This sequence for human SP-D is provided below as follows (SEQ ID NO:29).

```
  1 MLPFLSMLVL LVQPLGNLGA EMKSLSQRSV PNTCTLVMCS

41 PTENGLPGRD GRDGREGPRG EKGDPGLPGP MGLSGLQGPT

81 GPVGPKGENG SAGEPGPKGE RGLSGPPGLP GIPGPAGKEG

121 PSGKQGNIGP QGKPGPKGEA GPKGEVGAPG MQGSTGAKGS

161 TGPKGERGAP GVQGAPGNAG AAGPAGPAGP QGAPGSRGPP

201 GLKGDRGVPG DRGIKGESGL PDSAALRQQM EALKGKLQRL

241 EVAFSHYQKA ALFPDGRSVG DKIFRTADSE KPFEDAQEMC

281 KQAGGQLASP RSATENAAIQ QLITAHNKAA FLSMTDVGTE

321 GKFTYPTGEP LVYSNWAPGE PNNNGGAENC VEIFTNGQWN

361 DKACGEQRLV ICEF
```

A related peptide is the WMAP-10 peptide Marion Merrell Dow Research Institute) having the sequence succinyl-Leu-Leu-Glu-Lys-Leu-Leu-Gln-Trp-Lys-amide (SEQ ID NO:30). Alternative peptides are polymers of lysine, arginine or histidine that induce a lowering of surface tension in admixtures of phospholipids as described herein.

In still another embodiment, a polypeptide of this invention has amino acid residue sequence that has a composite hydrophobicity of less than zero, preferably less than or equal to −1, more preferably less than or equal to −2. Determination of the composite hydrophobicity value for a peptide is known in the art, see, U.S. Pat. No. 6,013,619, the disclosure of which is incorporated herein by reference. These hydrophobic polypeptides perform the function of the hydrophobic region of SP18. Thus, in one preferred embodiment, the amino acid sequence mimics the pattern of charged and uncharged, or hydrophobic and hydrophilic, residues of SP18.

It should be understood, however, that polypeptides and other surfactant molecules of the present invention are not limited to molecules having sequences like that of native SP-B (SP18). On the contrary, some of the most preferred surfactant molecules of the present invention have little resemblance to SP18 with respect to a specific amino acid residue sequence, except that they have similar surfactant activity and alternating charged/uncharged (or hydrophobic/hydrophilic) residue sequences.

One disclosed embodiment of the present invention comprises a peptide-containing preparation, the 21-residue peptide being a mimic of human SP-B consisting of repeated units of four hydrophobic leucine (L) residues, bounded by basic polar lysine (K) residues. This exemplary peptide, which is abbreviated herein as "$KL_4$," has the following amino acid residue sequence:

```
KLLLLKLLLLKLLLLKLLLLK.        (SEQ ID NO 1)
```

In one preferred embodiment, $KL_4$ is combined with the phospholipids dipalmitoyl phosphatidylcholine and palmitoyl-oleoylphosphatidyl glycerol (3:1) and palmitic acid, the phospholipid-peptide aqueous dispersion has been named "$KL_4$-Surfactant," and it is generally referred to herein in that manner. The $KL_4$-surfactant is being marketed under the name Model surfactant mixture. The efficacy of $KL_4$-Surfactant in various experimental and clinical studies has been previously reported, see, e.g., Cochrane et al, *Science* 254: 566-568 (1991); Vincent et al., *Biochemistry*. 30:8395-8401 (1991); Cochrane et al., *Am J Resp & Crit Care Med*, 152: 404-410 (1996); and Revak et al., *Ped. Res.*, 39:715-724 (1996).

In various embodiments of the present invention, the polypeptide:phospholipid weight ratio is in the range of about 1:5 to about 1:10,000, preferably about 1:7 to about 1:5,000, more preferably about 1:10 to about 1:1,000, and most preferably about 1:15 to about 1:100. In a particular preferred embodiment, the polypeptide:phospholipid weight ratio is about 1:37.

Synthetic polypeptides suitable for preparing the carrier surfactant composition in accordance with the present invention can be synthesized from amino acids by techniques that are known to those skilled in the polypeptide art. An excellent summary of the many techniques available may be found in J. M. Steward and J. D. Young, SOLID PHASE PEPTIDE SYNTHESSS, W.H. Freeman Co., San Francisco, 1969, and J. Meienhofer, HORMONAL PROTEINS AND PEPTIDES, Vol. 2, p. 46, Academic Press (New York), 1983 for solid phase peptide synthesis, and E. Schroder and K. Kubke, THE PEPTIDES, Vol. 1, Academic Press (New York), 1965 for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, (e.g., lysine).

Example 1 illustrates a solid phase synthesis of the surfactant peptide. Briefly, a protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and any solid support) are removed sequentially or concurrently, to afford the final polypeptide. That polypeptide is then washed by dissolving in a lower aliphatic alcohol, and dried. The dried surfactant polypeptide can be further purified by known techniques, if desired.

The surfactant proteins and polypeptides of the present invention may also be produced by recombinant DNA technology. The procedure of deriving protein molecules from the plant or animal hosts are generally known in the art. See, Jobe et al., *Am. Rev. Resp. Dis.*, 136:1032 (1987); Glasser et al., *J. Biol. Chem.*, 263:10326, (1988). Generally, a gene sequence encoding the proteins or polypeptides under the control of a suitable promoter and/or signal peptide is inserted into a plasmid or vector for transfecting of a host cells. The expressed proteins/polypeptide may be isolated from the cell culture.

While it is appreciated that many useful polypeptides disclosed herein, e.g., the $KL_4$ polypeptide (SEQ ID NO:1), comprise naturally-occurring amino acids in the "L" form that are joined via peptide linkages, it should also be understood that molecules including amino acid side chain analogs, non-amide linkages (e.g., differing backbones) may also display a significant surfactant activity and may possess other advantages, as well. For example, if it is desirable to construct a molecule (e.g., for use in a surfactant composition) that is not readily degraded, one may wish to synthesize a polypeptide molecule comprising a series of D-amino acids. Molecules comprising a series of amino acids linked via a "retro" backbone, ie., a molecule that has internal amide bonds constructed in the reverse direction of carboxyl terminus to amino terminus, are also more difficult to degrade and may thus be useful in various applications, as described herein For example, the following illustrates an exemplary molecule with a "retro" bond in the backbone:

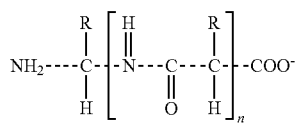

In another variation, one may wish to construct a molecule that adopts a more "rigid" conformation; one means of accomplishing this would be to add methyl or other groups to the α carbon atom of the amino acids.

As noted above, other groups besides a $CH_3$ group may be added to the a carbon atom, that is, surfactant molecules of the present invention are not limited to those incorporating a $CH_3$ at the α carbon alone. For example, any of the side chains and molecules described above may be substituted for the indicated $CH_3$ group at the α carbon component.

As used herein, the terms "analogs" and "derivatives" of polypeptides and amino acid residues are intended to encompass metabolites and catabolites of amino acids, as well as molecules that include linkages, backbones, side-chains or side-groups that differ from those ordinarily found in what are termed "naturally-occurring" L-form amino acids. (The terms "analog" and "derivative" may also conveniently be used interchangeably herein.) Thus, D-amino acids, molecules that mimic amino acids and amino acids with "designed" side chains (i.e., that can substitute for one or more amino acids in a molecule having surfactant activity) are also encompassed by the terms "analogs" and "derivatives" herein.

A wide assortment of useful surfactant molecules, including amino acids having one or more extended or substituted R or R' groups, is also contemplated by the present invention. Again, one of skill in the art should appreciate from the disclosures that one may make a variety of modifications to individual amino acids, to the linkages, and/or to the chain itself, which modifications win produce molecules falling within the scope of the present invention, as long as the resulting molecule possesses surfactant activity as described herein.

The composition can include other ingredients. For example, the surfactant mixture of the invention can includes (i) 50-95 dry weight percent phospholipid, (ii) 2-25 dry weight percent of a spreading agent effective to promote incorporation of the phospholipid into the surface lining layer of the lung, and (iii) 0.1 to 10 dry weight percent of lung-surfactant polypeptide. As indicated above, the components may be mixed in dry, solution, or particle-suspension form, and may be preformulated, prior to addition of the therapeutic agent, or may be formulated together with the agent.

Phospholipids useful in the compositions of the invention include native and/or synthetic phospholipids. Phospholipids that can be used include phosphatidylcholines, phospatidylglycerols, phosphatidylethanolamines, phosphatidylserines, phosphatidic acids, and phosphatidylethanolamines. Exemplary phospholipids phosphatidylcholines, such as dipalmitoyl phosphatidylcholine (DPPC), dilauryl phosphatidylcholine (DLPC)C12:0, dimyristoyl phosphatidylcholine (DMPC)C 14:0, distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2)), dipalmitoyl phosphatidylethanolanmine, dioleoylphosphatidylethanolamine (DOPE), dioleoyl phosphatidylglycerol (DOPG), palmitoyloleoyl phosphatidylglycerol (POPG), distearoylphosphatidylserine (DSPS) soybean lecithin, egg yolk lecithin, sphingomyelin, phosphatidylserines, phosphatidylglycerols, phosphatidyl inositols, diphosphatidyl glycerol, phosphatidylethanolamine, and phosphatidic acids.

In particular, 1,2-diacyl-sn-glycero-3-[phospho-rac-(1-glycerol)], 1,2-diacyl-sn-glycero-3-[phospho-L-serine], 1,2 diacyl-sn-glycero-3-phosphocholine, 1,2-diacyl-sn-glycero-3-phosphate, 1,2-diacyl-sn-glycero-3-phosphoethanolamine where the diacyl groups may be symmetrical, asymmetrical and contain either saturated or unsturated fatty acids of various types ranging from 3 to 28 carbons in chain length and with up to 6 unsaturated bonds.

One preferred phospholipid is DPPC. DPPC is the principal phospholipid in all mammalian species examined to date. DPPC is synthesized by epithelial cells of the airspaces (the type 2 pneumocyte of the alveoli and an as yet unidentified cell of the airways). DPPC is secreted into a cellular lining layer and spreads out to form a monomolecular film over the alveoli. The DPPC film at the air-ellular lining interface has certain unique properties that explain its normal function: (1) the film, which spreads to cover all surfaces, achieves extremely low surface tension upon compression, e.g., during exhalation, thereby reducing the net force that favors liquid movement into the airspace; (2) as airway or alveolar size falls, surface tension falls proportionately, thereby establishing a pressure equilibration among structures to prevent collapse; (3) because of its amphoteric structure, the film can form loose chemical associations with both hydrophobic and hydrophilic moieties and because of its high compressibility these associations can be broken upon film compression, thereby freeing the moiety from the interface; and (4) these loose chemical associations can be modified by the addition of other compounds found in the surfactant system (PG, for example) that can alter the charge distribution on the film, thereby altering the rate at which the moiety (as mentioned in (3) above) is released from the film.

In various embodiments of the invention, the lipid component is DPPC that comprises about 50 to about 90 weight percent of the surfactant carrier composition. In another embodiment of the invention, DPPC comprises about 50 to 75 weight percent of the surfactant composition with the remainder comprising unsaturated phosphatidylcholine, phosphatidylglycerol (PG), triacyglycerols, palmitic acid, spingomyelin or admixtures thereof in yet another embodiment of the invention, the lipid component is an admixture of DPPC and POPG in a weight ratio of about between 4:1 and 2:1. In one preferred embodiment, the lipid component is an admixture of DPPC and palmitoyl-oleoyl phosphatidylglycerol (POPG) in a weight ratio of about 3:1.

DPPC and the above-described lipids and phospholipids can be obtained commercially, or prepared according to published methods that are generally known in the arL The phospholipid component of the mixture includes one or more phospholpids, such as phosphatidylcholine (PC), phosphatidyl ethanolamine (PE), phosphatidylinositol (PI), phosphatidyl glycerol (PG), phosphatidylic acid (PA), phosphatidyl serine (PS), and sphingomyelin (SM). The fatty acyl chains in the phospholipids are preferably at least about 7 carbon atoms in length, typically 12-20 carbons in length, and may be entirely saturated or partially unsaturated.

The phospholipid(s) make up 50-95 dry weight percent of the surfactant mixture, and preferably between 80-90 percent by dry weight of the mixture.

It is known that phospholipids, such as DPPC, are absorbed relatively slowly to the aircell lining interface when administered alone and, once adsorbed, spread slowly.

The purposes of the spreading agent is to promote transition of surfactant-mixture lipids from particle form to monolayer form, leading to spreading on and distribution along and within the lung surface. Thus, for example, if the surfactant formulation is delivered to the lung in liposomal form, the spreading agent is effective in promoting transition of the liposomal phospholipids from liposomal bilayer to a planar monolayer form at the lung surface. Similarly, if the surfactant formulation is delivered to the lung as amorphous or crystalline lipid particles, the spreading agent is effective in promoting transition of the surfactant-mixture phospholipids to a planar monolayer form at the lung surface.

Exemplary spreading agents include but are not limited to non-phospholipid lipids that are compatible with lipid bilayer or lipid monolayer formation, but which alone are not able to support lipid-bilayer formation. Exemplary spreading agents include lysophospholipids; fatty acids, fatty esters, and fatty alcohols, and other single-long-chain fatty acyl compounds. Preferred spreading agents include fatty acids and fatty alcohols having alkyl chain lengths of at least about 12 carbon atoms, preferably between 15-20 carbon atoms in chain length. One preferred spreading agent is palmitic acid; another is cetyl alcohol. The spreading agent makes up between 2-25 dry weight percent of the surfactant mixture, preferably 10-15 dry weight percent of the mixture. One exemplary mixture, also containing DPPC:DOPG (3:1) at 84.5% dry weight, contains 12.75 dry weight percent palmitic acid.

The spreading agents used in the present invention may be purchased from commercial suppliers. For example, palmitic acid (PA) may be obtained from Avanti Polar Lipids, Inc. (Birmingham, Ala.). The spreading agents may also be prepared according to published methods that are generally known in the art.

In some embodiments, the composition can include Tyloxapol as a spreading agent, which can be purchased under several trade names from various companies such as Sterling-Winthrop, and Robm and Haas. Tyloxapol is a polymer of 4-(1,1,3,3-tetramethylbutyl)phenol) with formaldehyde and oxirane. Tyloxapol has been used in human pharmacologic formulations for over 30 years (Tainter M L et al. New England Journal of Medicine (1955) 253:764-767). Tyloxapol is relatively nontoxic and does not hemolyze red blood cells in a thousand times the concentrations at which other detergents are hemolytic (Glassman H N. Science (1950) 111:688-689).

Treatment Methods

Many conditions and diseases of the respiratory system cause lowering of pulmonary surfactant performance and inflammation. As used herein, the term "respiratory conditions and diseases(s)" encompass conditions and diseases involving the alveoli as well as air passages to the alveoli. Such conditions and diseases include pulmonary hypertension, neonatal pulmonary hypertension, neonatal bronchopulmonary dysplasia, chronic obstructive pulmonary disease (COPD), acute and chronic bronchitis, emphysema, bronchiolitis, bronchiectasis, radiation pneumonitis, hypersensitivity, pneumonitis, acute inflammatory asthma, acute smoke inhalation, thermal lung injury, allergic asthma, iatrogenic asthma, cystic fibrosis, alveolar proteinosis, alpha-1-protease deficiency, pulmonary inflammatory disorders, pneumonia, acute respiratory distress syndrome, acute lung injury, idiopathic respiratory distress syndrome, and idiopathic pulmonary fibrosis. The active agent can act directly on lung tissue, or on pathogenic organisms within pulmonary tissues.

It is generally recognized that a deficiency in lung surfactant is the cause of respiratory distress syndrome (RDS) in premature babies and infants. Although such deficiency is not the primary factor in the development of acute respiratory distress syndrome (ARDS), it may contribute significantly to the pathophysiology of this disorder. RDS is the leading cause of death and disability among premature infants. In addition, about 150,000 cases of ARDS are reported annually with 60-80% mortality. The mechanisms that trigger ARDS are only partly understood. However, in many cases that result from oxygen toxicity, the syndrome is brought on by large amounts of oxygen-derived free radicals and nucleophiles, such as peroxides, superoxides, hydroxyls, singlet oxygens, and others. Free radical induced damage to the pulmonary parenchyma results in inflammation and "lealy" capillary response. This response can progress to ARDS characterized by decreased pulmonary compliance, hypoxia and shunting.

Inflammation is a pervasive symptom that accompanies respiratory diseases and occurs in response to local trauma, bacterial infection, viral infection, allergic and immunogenic reactions, and the like. Inflammatory cells that are recruited to the inflammation site in the airways, particularly leukocytes, release mediators that can trigger or block the secretion of components of lung surfactant, and that are also able to disrupt epithelial cells lining the lung, causing release of cytoplasmic components. Included in this latter class of mediators are serine proteases, particularly leukocyte elastase, phospholipase $A_2$, and reactive oxygen species, such as superoxide and hydroxyl radicals. Infection of the airways in cystic fibrosis, for instance, is associated with abnormal transport properties of airway secretions that may be responsible for the severity of the disease (E. Puchell, et al., *Eur. J. Clin. Invest.*, 15:389-394, 1985).

The treatment methods of the invention employ a surfactant mixture with a protease inhibitor, a phospholipase inhibitor, or an antioxidant, or a mixture of two or more of these, as the active agent(s) in the formulation of the invention. The formulation can be a liquid formulation useful, for example, for bronchoalveolar lavage, oral intravascular, bolus or other administration. The formulation can also be aerosolized for administration to a patient. The amount of formulation administered is typically about 1-100 mg/dose, 5-20 mg/dose, e.g., 10 mg/dose, and the amount of active agent in the dose is a therapeutically effective amount, e.g., about 0.01 mg to 50 mg drug or about 0.01 mg to 5 mg drug. The actual drug dose can be determined by first calculating a desired agent concentration, when the formulation has spread in a monolayer in the lungs, and administering this dose in a suitable quantity of surfactant formulation. Adjustments to the dose, to optimize therapeutic effectiveness, and minimize side effects, can be determined according to known procedures that may involve animal models of pulmonary inflammation and/or clinical studies on human patients with pulmonary inflammatory conditions.

In one embodiment, the invention contemplates a method for treating pulmonary inflammation in a mammal comprising administering to the mammal a therapeutically effective amount of a composition comprising a protease inhibitor, a lipase inhibitor or an anti-oxidant.

In some embodiments, the method involves administration of a composition of the invention by pulmonary lavage. Procedures for performing pulmonary lavage are available in the art See, e.g., U.S. Pat. No. 6,013,619, which is incorporated herein by reference. For example, pulmonary lavage can be performed as follows:

a) applying gas positive end-expiratory pressure (PEEP) with a ventilator into a lung section of the mammal at a regulated pressure, preferably from about 4 to 20 cm water, b) instilling a lavage composition containing dilute surfactant in a pharmaceutically acceptable aqueous medium into one or more lobes or sections of the lung; and c) removing the resulting pulmonary fluid from the lung using short intervals of tracheo-bronchial suction, preferably using a negative pressure of about 20 to 100 mm mercury.

Typically, the PEEP is applied for a preselected time period prior to instilling step (b), preferably up to about 30 minutes, and in addition PEEP is typically applied continuously during steps (b) and (c) and for a preselected time period after removing step (c), preferably up to about 6 hours. Different sections of the lung can be treated independently.

In other embodiments, the compositions can be administered by liquid bolus administration. For example, a tracheal tube may be positioned to deliver drops of the composition to pulmonary tissues. In some embodiments, bolus administration can be to one portion of the lung and not to another, or different portions of the lung can be treated by bolus drip administration at different times.

In still other embodiments, the compositions can be administered inhalation. In further embodiments, the protease inhibitors, lipase inhibitors and/or antioxidants can be administered orally or parenterally. When oral or parenteral (non-pulmonary) delivery is contemplated, the composition need not include the surfactant mixture. However, according to the invention, the combination of the surfactant mixture and the inhibitors is surprising effective for treating pulmonary disorders. Hence, the surfactant-inhibitor combination may act synergistically to beneficially treat pulmonary conditions.

Hence, the invention provides pharmaceutical compositions that comprise protease inhibitors carried in a surfactant carrier for treatment of pulmonary inflammation.

In one exemplary embodiment, the composition contains an inhibitor of human leukocyte elastase. Human leukocyte elastase (HLE) is a proteolytic enzyme present in the azureophilic granules of neutrophils. After being released at sites of inflammation, this protease is capable of hydrolyzing important connective tissue components, such as elastin and collagen. This enzyme is essential to their function in phagocytosing necrotic tissue and microorganisms. At the same time, this enzyme poses a significant challenge to the body because their uncontrolled release can lead to the destruction of healthy tissue and circulating proteins. It has been proposed that the resulting tissue damage contributes to the etiology of adult respiratory distress syndrome (Lee, C. T., et al., *New England J. of Med.*, 304:192-196, 1981 and emphysema (Janoff, A., In: INFLAMMATION: BASIC PRINCIPLES AND CLINICAL CORRELATES, Gallin, J. I., et al., eds, 803-814, Raven Press, New York, 1988).

According to the invention, inhibition of the proteases and lipases and/or reduction of oxidation within pulmonary tissues results in lessened damage to the vascular basement membrane and diminished protein leak and hemorrhage. In parallel studies, bronchoalveolar lavage with exogenous surfactant also diminished the damage to the basement membrane, protein leak and hemorrhage. However, treatment with surfactant mixtures alone did not significantly inhibit protease or lipase activity, and did not provide significant antioxidant activity. In accordance with the present invention, treatment of pulmonary inflammatory conditions with the surfactant formulation of the invention containing protease inhibitors, lipase inhibitors and/or anti-oxidants is effective in inhibiting basement membrane damage, protein leak and pulmonary vascular hemorrhage. The therapy, by reducing optimally the vascular protein leak and hemorrhage, may also prevent inactivation of native surfactant and the development of an inflammatory exudate in the lungs that results in severe loss of pulmonary function, multiple organ dysfunction and death in 30-40% of patients.

Protease inhibitors include elastase inhibitors, such as human leukocyte elastase inhibitor, human secretory leukocyte protease inhibitor (SLPI), alpha 1-proteinase inhibitor (or alpha1 antitrypsin) and other Kunitz or serine protease inhibitors. Further protease inhibitors suitable for use in the invention are described above.

Exemplary anti-oxidants include EUK134, catalase, glutathione, N-acetylcysteine, procysteine, alpha-tocopherol, ascorbic acid, butylated hydroxy anisole (BHA), butylated hydroxytolune (13HT), natural flavidins (e.g., 2,7-dihydroxy 9,10 dihydrophenanthro-4,5 bed-pyran, see U.S. Pat. No. 6,503,552) and derivatives of these compounds. An exemplary phospholipase $A_2$ inhibitor is LY11-727 (Eli Lilly).

Experiments were performed to illustrate the therapeutic efficacy of the pharmaceutical composition in inhibiting protease activity. The study first established an assay for measuring elastase activity in rabbit and/or human bronchoalveolar lavage (BAL) fluids (Example 3). The resultant colorimetric signal in a sample with human neutrophil elastase (HNE) activity correlates linearly with the optical density at 410 nM ($OD_{410}$). The ability of an elastase inlubitor to inhibit HNE was then examined (Example 4). The correlation between the $OD_{410}$ of the mixture to the log of the amount of inhibitor added is linear (FIG. 5A) demonstrating that HNE activity is inhibited in vitro by the serine elastase inhibitor.

Figure 5A:
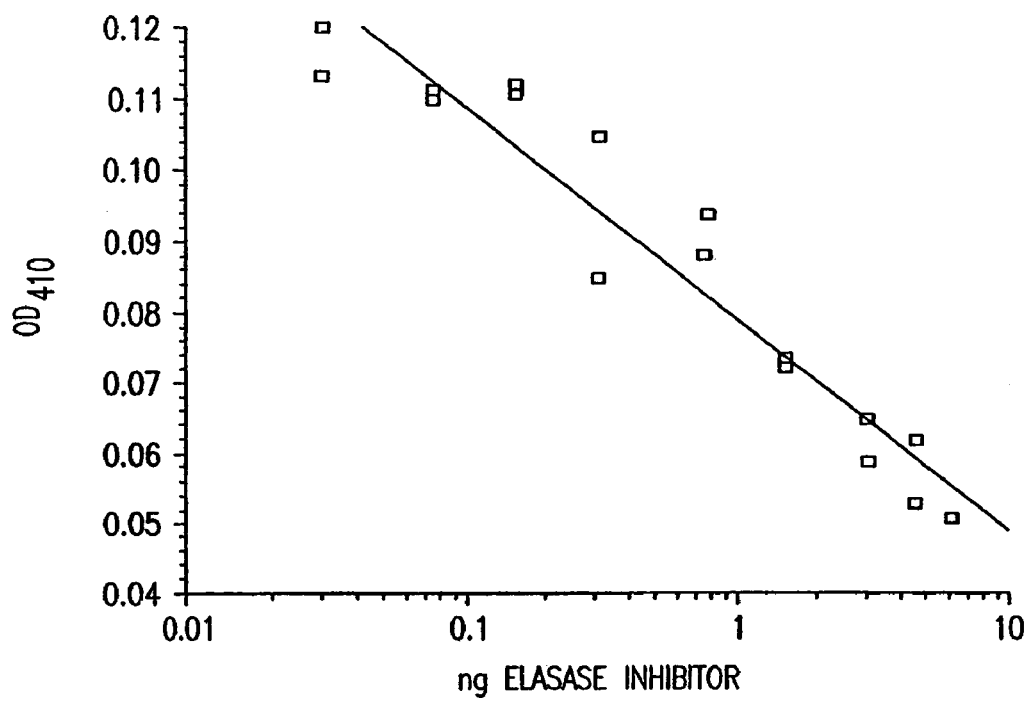
FIG. 5A is an inhibition curve that plots the log amount of a known serine elastase inhibitor added to a standard amount (0.125 μg) of human neutrophil elastase (HNE) to the corresponding $OD_{410}$ of the mixture.
Figure 5B:
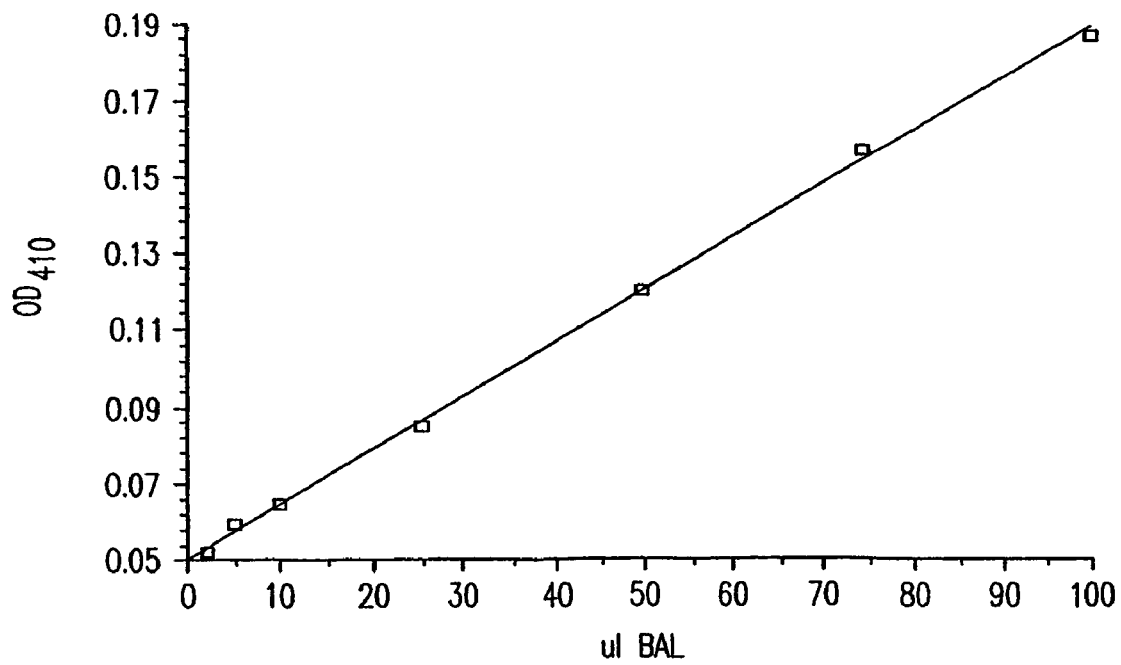
FIG. 5B shows the dose-response between the amount of BAL fluid recovered from an ARDS patient and the $OD_{410}$ in a colorimetric assay of elastase activity.

The elastase activity in BAL fluids taken from humans with ARDS (acute respiratory distress syndrome) and rabbits with experimentally induced respiratory distress were then measured with the established calorimetric assay. FIG. 5B shows a linear correspondence between the amounts of BAL and $OD_{410}$; demonstrating elastase activity can be measured by the colorimetric assay and that elastase is present in BAL fluids of humans with ARDS.

Figure 6A:
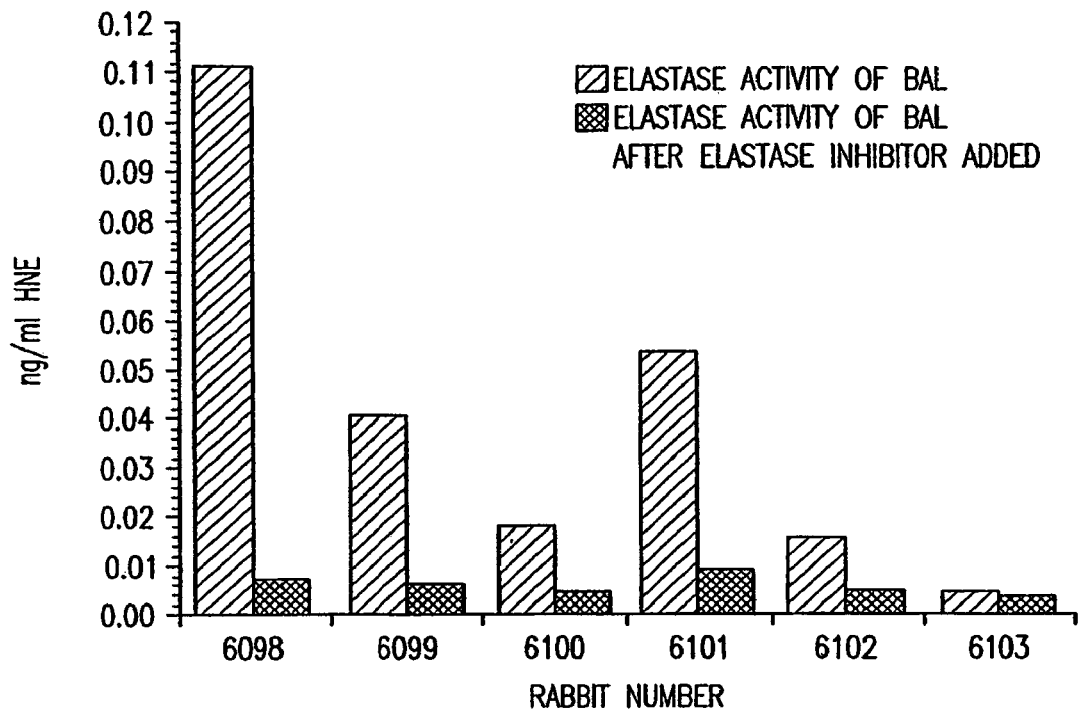
FIG. 6A shows the elastase activity in the BAL fluids taken from the lungs of rabbits six hours after they were treated with 3 mg anti-BSA/kg (rabbits 6098 and 6099) or 5 mg anti-BSA/kg (rabbits 6100-6103) instilled intratracheally, and additionally 10 mg of BSA given intravenously (6098-6101) (bars with diagonal lines). In comparison, the elastase activity in these BAL fluids after the addition of 100 μg/ml of a known serine elastase inhibitor is also shown (bars with crosshatching). Elastase activity is expressed as the concentration of human neutrophil elastase (HNE) that gives a corresponding OD at 410 nm.

Similarly, a colorimetric assay was performed on bronchoalveolar (BAL) fluids taken from rabbits with induced lung injuries (example 6). The colorimetric assay was also performed on each of the BAL fluids after the addition of 100 μg/ml of a serine elastase inhibitor. FIG. 6A shows the elastase activity in the BAL fluids alone and also in BAL fluids with an added serine elastase inhibitor. Elastase activity is expressed as the concentration of HNE that gives a corresponding $OD_{410}$. Elastase activity was observed in all of the rabbit BAL fluids and the activity was inhibited in five out of the six BAL fluids by the added serine elastase inhibitor. Since the serine elastase inhibitor added is a known HNE inhibitor (Example 4), the measured elastase activity was likely due to HNE.

It should be noted that lavage fluids can contain endogenous elastase inhibitors. This may be $\alpha_1$-protease inhibitor, $\alpha_2$-macroglobulin, a SLPI, or another elastase inhibitor. The presence of such inhibitor(s) can be shown by in vitro assays of bronchoalveolar (BAL) fluids from rabbits with induced pulmonary injury (Example 6). Referring to FIG. 6A, BAL fluids were taken from rabbits 3 hours (rabbits 6315 and 6316) or 6 hours (6313, 6314, 6317, and 6318) after they were given bacterial lipopolysaccharide (LPS) and anti-BSA intratracheally (all animals); animals 6317 and 6318 additionallyreceived 10 mg/kg of BSA at 3 hours, and the extracted BAL fluids were tested alone (cross-hatched) or after mixing with 1 μg/ml HNE (dark solid bar). Significant amount of free elastase was present in the BAL fluid from animal 6317; fluids from all the other animals showed the presence of an inhibitor of elastase, particularly HNE inhibitors. Thus, the absence of free elastase activity in a rabbit BAL fluid does not indicate the absence of elastase in the sample, it may be present but inhibited. Immunological assays could be performed to differentiate.

The effects of Model surfactant mixture, the serine elastase inhibitor, and the combination of the two on pulmonary inflammation were evaluated on an ARDS Rabbit Model. These experiments are described in details in Examples 8 to 12. Twenty (20) rabbits were divided into five groups for this study. Pulmonary inflammation was induced in Groups 1-4 rabbits from stimulation by lavaging with bacterial lipopolysaccharide (LPS) and, 3 hours later, with phorbol myristate acetate (PMA). Additionally, as treatment, Group 2 rabbits received Model surfactant mixture, Group 3 rabbits received the serine elastase inhibitor, and Group 4 animals received both Model surfactant mixture and the serine elastase inhibitor. Group 5 rabbits were normal rabbits and were used as control. The animals were sacrificed at six (6) hr., the right lower lobe was lavaged three times and the lavage fluids were pooled (terminal lavage) for each animal. The level of injury and the effect of the treatments were measured by the amount of basement membrane protein fragments and red blood cells found in terminal lavage fluids.

Figure 7A:
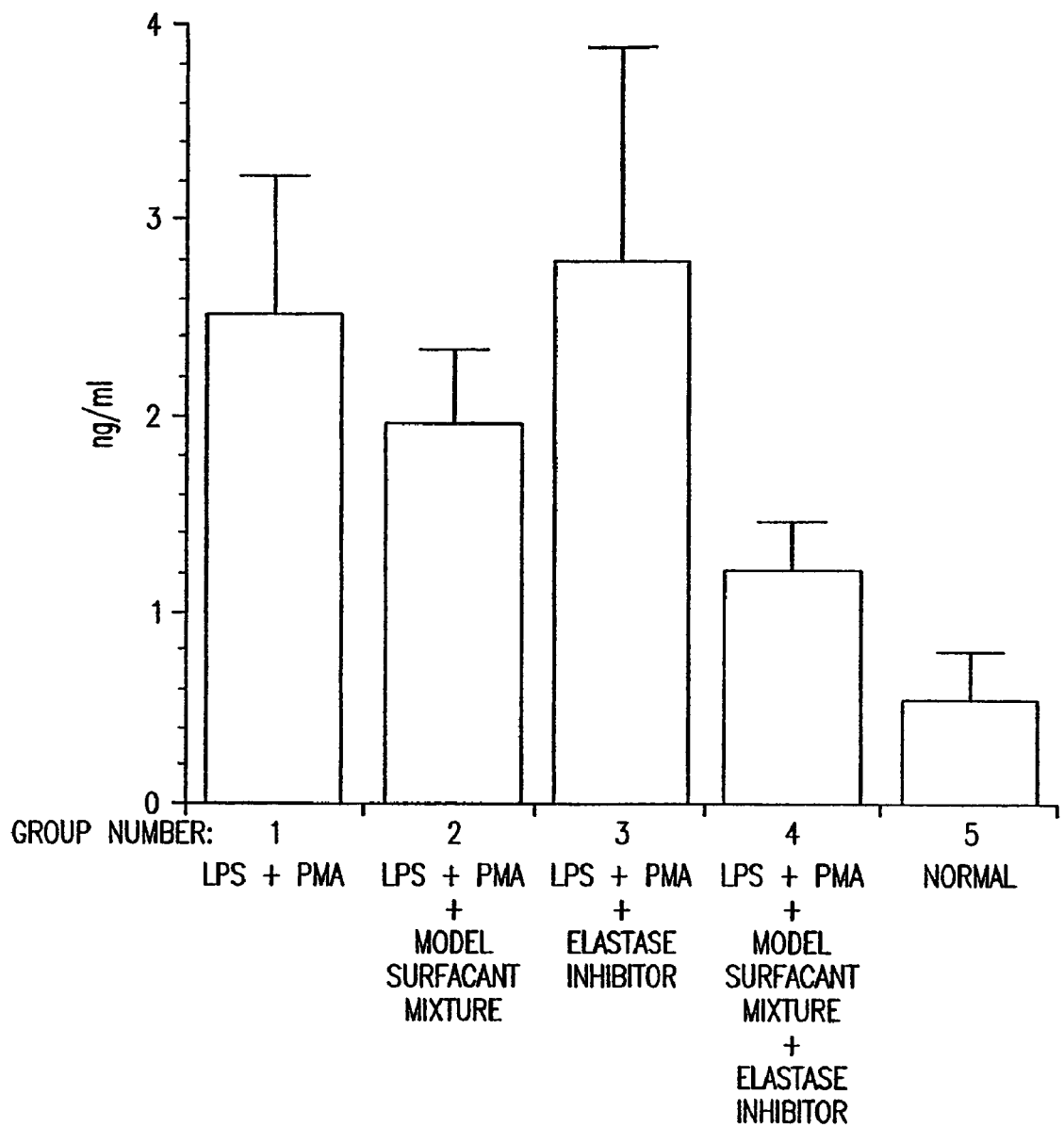
FIG. 7A shows the mean protein values in the terminal lavage fluid (6 hours post injury) of normal rabbits (Group 5) or rabbits injured with bacterial liposaccharide (LPS) and phorbol myristate acetate (PMA) (Group 1) and also treated with Model surfactant mixture (Group 2), a known serine elastase inhibitor (Group 3) or Model surfactant mixture and the serine elastase inhibitor combined (Group 4). See Example 8 for quantities used and treatment times. Error bars depict SEM. One animal in Group 3 had an unusually high protein value, reflected in the large error bar, and skewed the protein value for this group higher than it otherwise would have been. Elimination of the aberrant value would result in a mean value for group 3 of 1.72.

FIG. 7A shows that heightened amounts of protein present in the terminal lavage fluids taken from animals with pulmonary injury. The amount of protein found is indicative of a level of injury to the basement membrane matrix that allows plasma proteins to leak through into the alveolar space; the higher the amount of protein, the more injury that is present in the lungs. The results show that the amount of protein (approximately 2.5 mg/ml) resulting from the LPS and PMA injury was reduced in Group 2 that received Model surfactant mixture alone and even further reduced in Group 4 that received both Model surfactant mixture and the elastase inhibitor. The failure of Group 3, which received the elastase inhibitor alone, to show a reduction in protein levels was most likely due to the abnormally high value obtained for one animal in the group. If this animal were excluded, the mean value for Group 3 would be approximately equal to the value obtained for Group 2 treated with Model surfactant mixture alone.

Figure 7B:
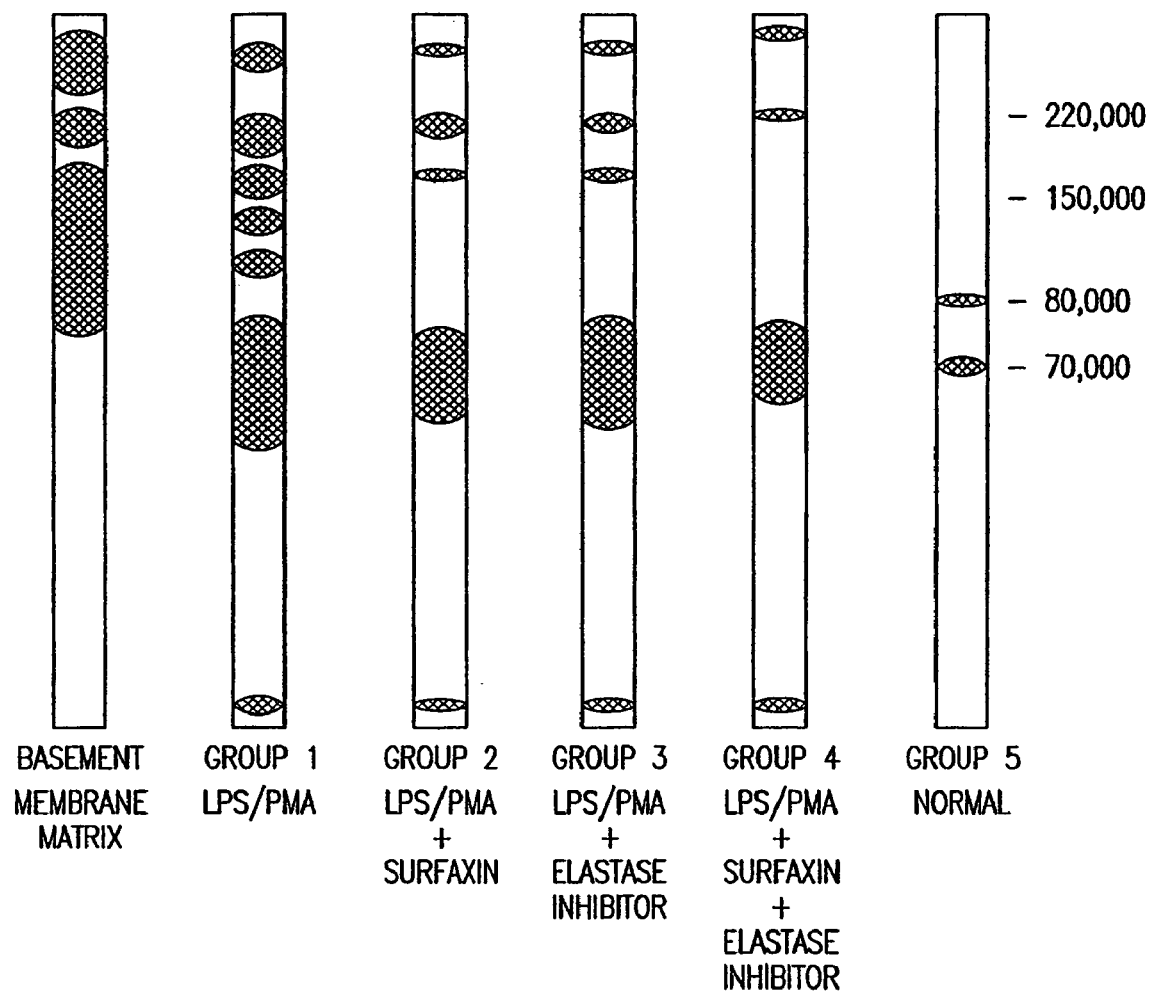
FIG. 7B is a diagram of a Western blot analysis of BAL fluids obtained from rabbits with LPS/PMA-induced pulmonary injury. Antibodies directed against basement membrane proteins were used to detect whether basement membrane proteins were present in these BAL fluids. The first (leftmost) lane contained basement membrane proteins ranging in size from about 80,000 kDa and higher as a control. Basement membrane proteins of lower molecular weight (about 10,000) as well as the higher molecular weight basement membrane proteins were present in BAL fluids of rabbits treated with LPS and PMA alone (lane 2, Group 1). Somewhat lesser amounts of basement membrane proteins were present when the LPS/PMA-injured rabbits were treated with Model surfactant mixture (Group 2), a serine elastase inhibitor (Group 3), and both Model surfactant mixture and a serine elastase inhibitor (Group 4). Normal, uninjured, rabbit lavage had little or no low molecular weight basement membrane proteins (last, rightmost panel, Group 5). The large band present at 70,000 MW in Groups 1-4 is albumin, present as a contaminant in the antiserum used. The bands above 90,000 MW are specific to the basement membrane and not present in normal rabbit plasma (data not shown). The low MW bands (<10,000 MW) represent fragments of the basement membrane.

FIG. 7B shows the Western blot analysis performed on the SDS-gel analyses of the proteins found in the terminal lavage fluids using an antibody produced in guinea pigs to the basement membrane matrix protein. The protein components of rabbit pulmonary basement membrane are presented in the left panel. The protein components in the BAL fluids of rabbits treated with LPS and PMA alone, with the addition of Model surfactant mixture, with the addition of the serine elastase inhibitor and with the addition of both Model surfactant mixture and the elastase inhibitor are present in the Group 1 to Group 4 panels, respectively. The protein components in the BAL fluid of the normal, uninjured rabbit are shown in the Group 5 panel. In these panels, the bands above 90,000 MW are specific to the basement membrane and not present in normal rabbit plasma (data not shown). The large band at 70,000 MW in Groups 1-4 is albumin, which is a contaminant in the antiserum used. The low MW bands (<10,000 MW) represent fragments of the basement membrane. Amelioration of the damage in the basement membrane is observed, and can be quantified, in animals treated with either Model surfactant mixture, the elastase inhibitor, or the combination of both.

Figure 7C:
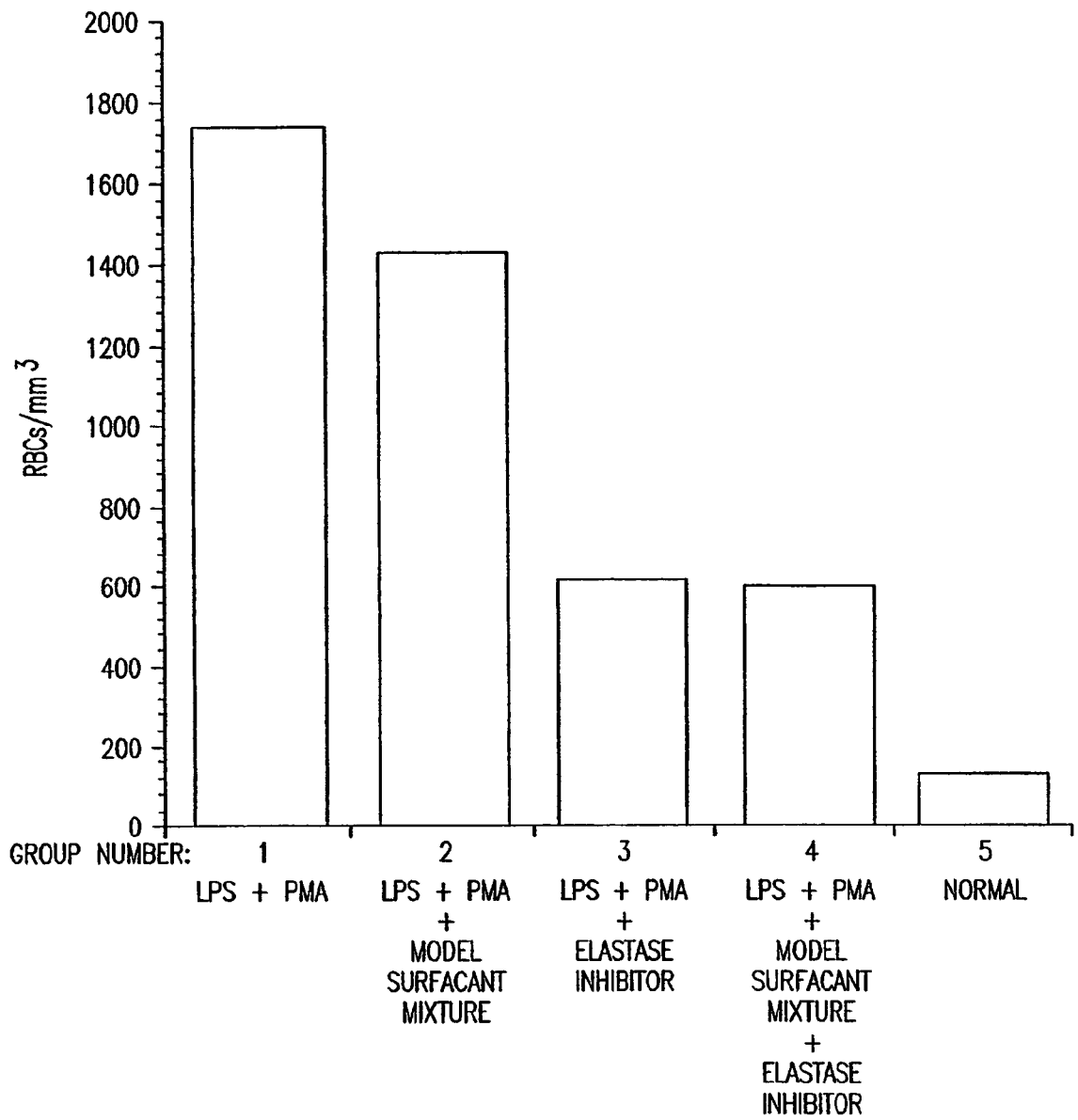
FIG. 7C shows the average number of red blood cells (RBCs) in terminal lavage fluids (6 hours post injury) of animals injured with LPS and PMA and treated in various ways. Two animals from the normal rabbit group (Group 5) that received no treatment were used as controls. Rabbits injured with LPS and PMA (Group 1) that received no further treatment had the highest number of RBCs. LPS/PMA injured rabbits treated with Model surfactant mixture (Group 2) had fewer RBCs. Those treated with elastase inhibitor (Group 3) or Model surfactant mixture and elastase inhibitor (Group 4) had even fewer RBCs in their lavage fluid.

Another measurement of the level of injury in the animals is the amount of hemorrhage or red blood cells (RBCs) appearing in the terminal lavage fluid. The presence of RBCs indicates an even larger degree of injury, as compare to the presence of protein, one that allows whole blood cells to pass through holes created in the matrix. FIG. 7C shows the RBC counts in the terminal lavage fluids. A slight drop in the number of RBCs, suggesting some amelioration of injury, was seen when Model surfactant mixture was added, and a greater reduction in injury was seen when the elastase inhibitor was added. The addition of both Model surfactant mixture and elastase inhibitor also resulted in a significant reduction of injury.

Figure 8:
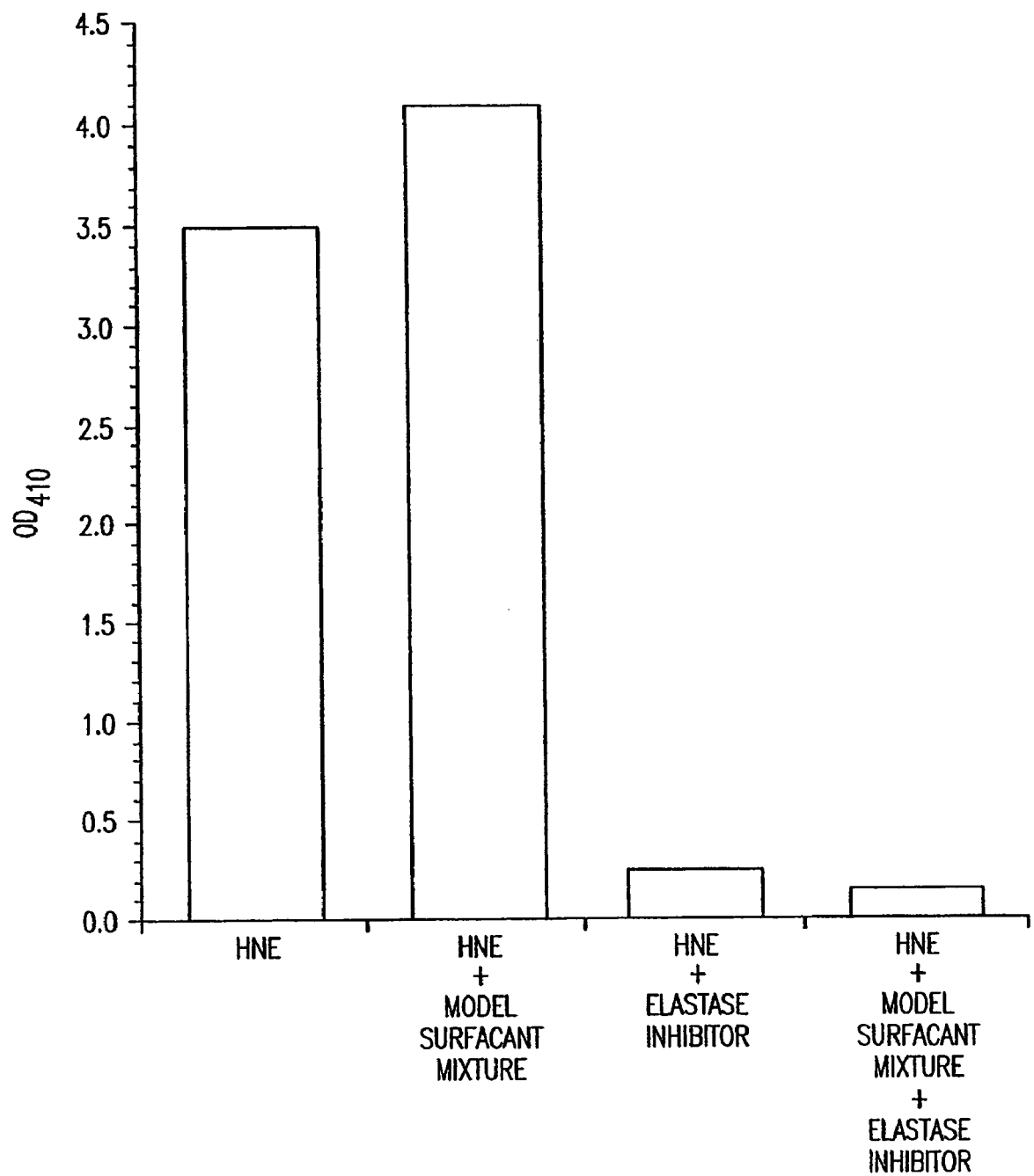
FIG. 8 shows the inhibition of a known quantity of HNE (0.02 μg) by Model surfactant mixture (2 mg/ml final concentration), a known serine elastase inhibitor (100 μg/ml), or both Model surfactant mixture and the serine elastase inhibitor together.

It has been previously shown that rabbits depleted of circulating neutrophils by treatment with nitrogen mustard do not show significant injury when exposed to LPS and PMA. This is evidenced by their lack of protein, RBCs, and elastase in the terminal lavage fluids. (Cochrane, C G, et al., *Am. J. Resp. and Crit. Care Med.*, Vol. 163:139, 2001). This suggests strongly that the source of the elastase in vivo is the neutrophil. The ability of Model surfactant mixture only, the serine elastase inhibitor alone, and the two combined to inhibit the activity of human neutrophil elastase was evaluated. FIG. 8 shows significant inhibition of HNE activity from the elastase inhibitor with or without the additional presence of Model surfactant mixture. Model surfactant mixture does not interfere with the ability of the elastase inhibitor to inhibit elastase, nor does it itself directly inhibit elastase.

Figure 9:
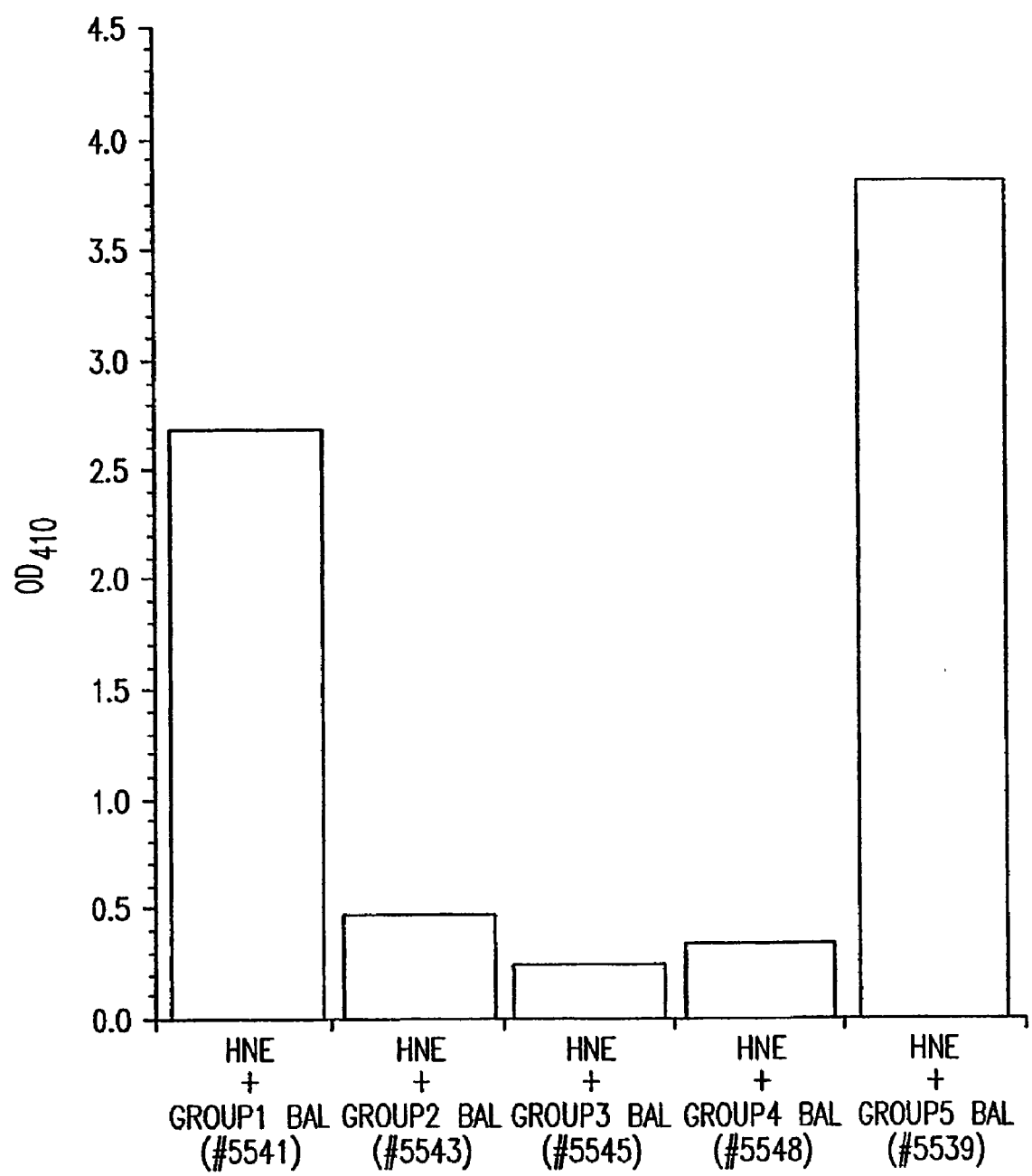
FIG. 9 shows the extent of elastase inhibition in the terminal lavage fluids of the treatment groups described in Example 12.

The residual activity of elastase inhibitors in the terminal BAL fluids was evaluated by incubating the BAL fluids with a known amount of HNE (Example 12). The result is presented in FIG. 9. A significant lowering of HNE activity, as measured by the $OD_{410}$, is seen in Groups 2-4. The lowering of HNE activity indicates the presence of one or more elastase inhibitors. The elastase inhibition seen with the lavage fluids from Groups 3 and 4 was significant—animals in these groups received the known elastase inhibitor by both intravenous and intratracheal routes. However, the elastase inhibition seen in the Model surfactant mixture group (Group 2), could also be due to endogenous elastase inhibitors in the rabbit such as SLPI or alpha-1 protease inhibitor, or some combination. Normal rabbits (Group 5) and the LPS/PMA positive injury animals (Group 1) did not show the presence of elastase inhibitor in their terminal lavage fluids in this experiment. Rabbit #5541 (Group 1) did, however, show the presence of free elastase in the terminal BAL fluid; none was detected in the normal animal's BAL (Group 5).

The studies described above showed that elastase released from leukocytes was a likely source of the proteolytic injury observed in the lungs of rabbits having induced pulmonary inflammation. The acute lung injury resulted in a degradation of the pulmonary vascular basement membrane and the release into the alveolar space of plasma proteins and red blood cells. Treatment of the animals with Model surfactant mixture or a serine elastase inhibitor, or the combination of the two lessened the degree of injury. Thus it is believed that a pharmaceutical composition containing Model surfactant mixture and a serine elastase inhibitor will be successful in preventing and treating inflammation injury of the lungs.

As noted above, the invention is advantageous for treating a variety of pulmonary conditions, including those in which no inflammatory component is involved. Asthma and related broncho-constriction conditions may be advantageously treated by administering a surfactant formulation containing bronchodilators, such as albuterol, terbutaline, salmeterol, formoterol, and pharmacologically acceptable salts thereof.

Bacterial infections of the lungs, such as bronchitis and tuberculosis can be advantageously treated with the surfactant containing an antibiotic as the active agent.

Cystic fibrosis may be advantageously treated by administering the surfactant formulation of the invention, prepared for delivery of DNase.

Hence, the present compositions can also include other useful agents. For example, the following agents may be included: bronchial-dilators, antibiotics, DNase, pain medicaments, or polypeptides, such as cytokines, and peptide hormones.

Improved Distribution and Uptake

This section describes the factors provided by the above surfactant formulation that contribute to improved drug distribution and uptake in the lungs. The improved drug distribution is likely due to a combination of factors that include (i) improved spreading and dissemination of the drug at the lung surface, in effect, increasing the effective surface area over which the drug can transit into and through the lungs, and (ii) stabilizing the lipid monolayer at the lung surface, thus maintaining a favorable drug-transit interface at the lung surface.

Figure 4A:
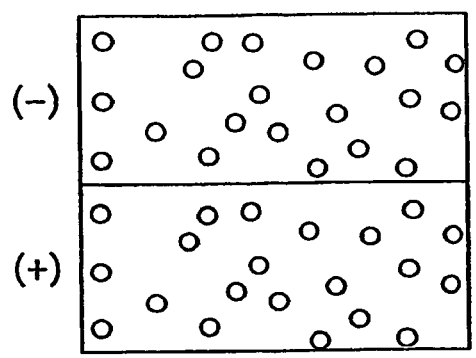
FIGS. 4A and 4B illustrate the deposition and spreading of a drug delivered with (+) and without (−) a surfactant at time zero (FIG. 4A), and the effects of spreading on the ability to enhance cellular uptake and penetration in the lung over time (FIG. 4B).
Figure 4B:
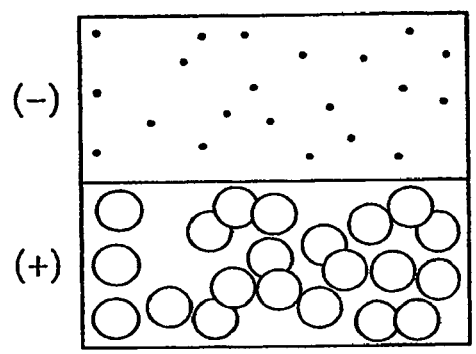

FIGS. 4A and 4B illustrates the deposition and spreading of an active agent delivered to the lung in a lipid-particle, with and without lipid spreading. FIG. 4A illustrates schematically the sizes of lipid particles immediately after deposition, both in the presence (+, open circles) and absence (−, partially shaded circles) of spreading. With increased time (FIG. 4B), the difference in area of coverage becomes more pronounced, as the spreading particles continue to expand, fuse and form a large-area coverage at the deposition area. Without spreading, the particles remain discrete and localized, releasing their contents only at small, localized areas.

The total area that can be covered by a given quantity of lipid particles of a given size can be readily calculated in terms of the total monolayer area represented by the particle lipid. As an example, the calculated surface area of 10 mg of a surfactant formulation particles of 1 µm size is 60 $cm^2$ or about 0.00125% percent of the total surface area of the lung. With spreading, where the phospholipids in the particles are dispersed in monolayer form, the total surface covered by the formulation (which would include active agent dispersed in the lipid is calculated to be 34% of the lung surface. Thus, spreading has enhanced the total lung surface available for drug transit into or across the lungs by about at least 4 orders of magnitude.

In addition to greatly increasing the lung surface area for drug delivery, the surfactant formulation invention promotes more efficient uptake by stabilizing the monolayer against collapse under pressure and allowing lipids to incorporate into the monolayer lung surface without destabilizing the monolayer.

Figure 4C:
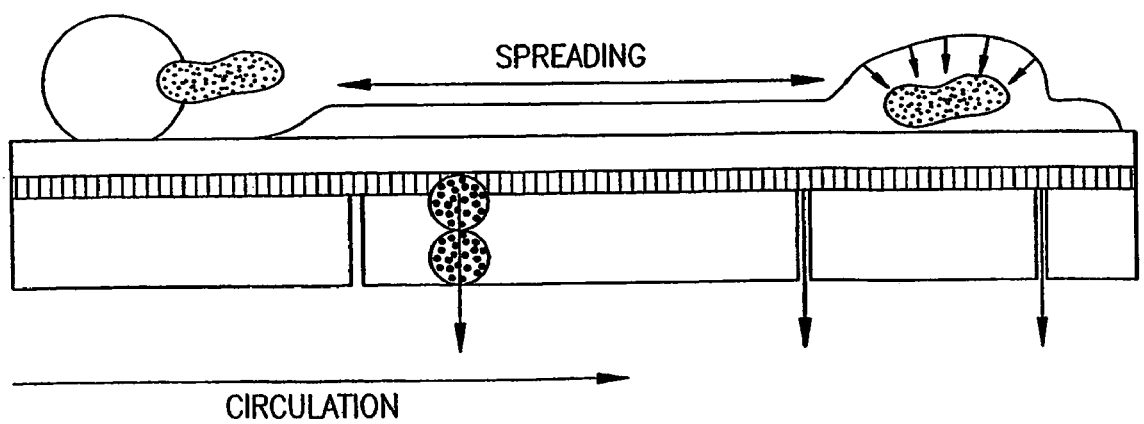
FIG. 4C illustrates how various drug-delivery advantages of the invention are achieved.

FIG. 4C illustrates how these features contribute to enhanced cellular uptake and penetration of an active agent delivered to a patients pulnorary region. At the left in the figure shows a localized lipid particle deposited on lung surface effectively covering only the small surface area of the particle itself. Drug delivery from this particle will be limited by the rate of diffusion of the drug from the particles, and/or the rate of dissolution of the particle.

The illustration at the right in the figure shows the effect of lipid spreading in a particle having the surfactant formulation of the present invention. The figure is intended to show that the particle lipids and associated drug have spread over a large surface area at the monolayer/air interface of the lung surface. The drug is now distributed for immediate uptake over a large lung-surface area, for uptake by mechanisms that include vesicular, paracellular, or transcellular penetration. Vesicular transport is a rather loose description of a number of complicated mechanisms that occur at the surface of cells. Cell membranes within the alveoli create a vesicle that contains the drug and such fusion between the drug particle and the cell membrane can arise spontaneously. Drugs, particularly macromolecules, may be transported across cell membranes by such a pathway. In paracellular uptake, the active agent diffuses through the paracellular space between epithelial cells, for uptake into the circulation. Transcellular uptake and penetration involves direct uptake into, through, and out of a lung epithelial into the circulation.

FIG. 3C also shows how spreading and monolayer stabilization in drug delivery can enhance treatment of a pulmonary pathogen, in this case a bacterium on the lung surface. In the absence of spreading, the lipid particle may or may not make contact with the pathogen particle. In the absence of spreading, drug delivery occurs only at the point of contact or by diffusion of the drug. Lipid spreading, on the other hand, is able to engulf the pathogen, allowing drug uptake by the pathogen across the whole of its outer surface.

The features just discussed are particularly useful for administration of compounds, such as protease or phospholipase inhibitors, and anti-oxidants for use in treating pulmonary inflammation conditions, where the active polypeptide agent needs to be widely distributed over the lung tissue. Moreover, such features are useful for treating lung conditions that affect a large proportion of the lung, because the administered drug is available rapidly over a large lung-surface area. Also, these features are useful for administering polypeptides and peptides that may not diffuse readily on their own. Antibiotics, including peptide antibiotics, that need to penetrate to sites of infection within the lungs are efficiently administered and are readily available after administration to attack bacteria on the lung surface.

Compositions

The protease inhibitors, lipase inhibitors, antioxidants and surfactant mixtures of the invention may be formulated into a variety of acceptable compositions. Such pharmaceutical compositions can be administered to a mammalian host, such as a human patient, in a variety of forms adapted to the chosen route of administration, i.e., by lavage, orally or parenterally, by intravenous, intramuscular, pulmonary or inhalation routes.

In cases where compounds, for example, antioxidant and polypeptide inhibitor or other compounds, are sufficiently basic or acidic to form stable nontoxic acid or base salts, administration of such compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

Pharmaceutically acceptable salts of polypeptides include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Thus, the present compositions containing protease inhibitors, lipase inhibitors or antioxidants may be systemically administered, e.g. orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compositions may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of protease inhibitors, lipase inhibitors, or antioxidants in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active agents may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the protease inhibitors, lipase inhibitors or antioxidants in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the protease inhibitors, lipase inhibitors or antioxidants plus any additional desired ingredient present in the previously sterile-filtered solutions.

Useful dosages of protease inhibitors, lipase inhibitors or antioxidants of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the protease inhibitors, lipase inhibitors or antioxidants of the present invention in a liquid composition will be from about 0.01-25 wt-%, or from about 0.1-10 wt-%.

The amount of protease inhibitors, lipase inhibitors or antioxidants, or active salt s or derivatives thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 100 mg/kg, e.g., from about 1.0 to about 75 mg/kg of body weight per day, such as 1 to about 50 mg per kilogram body weight of the recipient per day, or in the range of 3 to 90 mg/kg (day or in the range of 5 to 60 mg/kg/day.

The protease inhibitors, lipase inhibitors or antioxidants are conveniently administered in unit dosage form; for example, containing 5 to 1000 mg, conveniently 10 to 750 mg, most conveniently, 50 to 500 mg of active ingredient per unit dosage form.

Ideally, the protease inhibitors, lipase inhibitors or antioxidants should be administered to achieve optimal treatment of pulmonary conditions. When orally, intravenously or parenterally administered peak plasma concentrations of the active agents can be achieved of from about 0.5 to about 75 $\mu M$, or, about 1 to 50 $\mu M$, or, about 2 to about 30 $\mu M$. This may also be achieved, for example, by the intravenous injection of a 0.05 to 5% solution of the protease inhibitors, lipase inhibitors or antioxidants, optionally in saline, or orally administered as a bolus containing about 1-100 mg of the protease inhibitors, lipase inhibitors or antioxidants. Desirable blood levels may be maintained by continuous infusion to provide about 0.01-5.0 mg/kg/hr or by intermittent infusions containing about 0.4-15 mg/kg of the protease inhibitors, lipase inhibitors or antioxidants.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, an antioxidant enters the cell and reacts with the reactive oxygen species thereby reducing the concentration of reactive oxygen species in the cell. In an alternative embodiment, an antioxidant enters the cell or is present in the surrounding extracellular milieu and reacts with the oxidants generated from reactive oxygen species.

Protease inhibitors, lipase inhibitors or antioxidants contemplated for use in the present invention can be delivered directly to the site of interest (the lung) to provide immediate relief of the symptoms of pulmonary inflammation Such delivery can be by bronchoalveolar lavage, intratracheal administration, inhalation or bolus administration. In these case the surfactant mixture is included.

Procedures for performing pulmonary lavage are available in the art. See, e.g., U.S. Pat. No. 6,013,619, which is incorporated herein by reference. For example, pulmonary lavage can be performed as follows:

a) applying gas positive end-expiratory pressure (PEEP) with a ventilator into a lung section of the mammal at a regulated pressure, preferably from about 4 to 20 cm water, b) instilling a lavage composition containing dilute surfactant in a pharmaceutically acceptable aqueous medium into one or more lobes or sections of the lung; and c) removing the resulting pulmonary fluid from the lung using short intervals of tracheo-bronchial suction, preferably using a negative pressure of about 20 to 100 mm mercury.

Typically, the PEEP is applied for a preselected time period prior to instilling step (b), preferably up to about 30 minutes, and in addition PEEP is typically applied continuously during steps (b) and (c) and for a preselected time period after removing step (c), preferably up to about 6 hours.

Delivery by inhalation is described further herein. Alternative delivery means include but are not limited to administration intravenously, orally, by inhalation, by cannulation, intracavitally, intramuscularly, transdermally, and subcutaneously.

Therapeutic compositions of the present invention contain a physiologically tolerable carrier together with surfactant mixtures, protease inhibitors, lipase inhibitors or antioxidants as described herein, dissolved or dispersed therein as an active ingredient In a preferred embodiment, the therapeutic composition is not immunogenic when administered to a mammal or human patient for therapeutic purposes.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredients can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredients.

Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes In some embodiments, the liquid carrier is a Tham buffered system, which can be prepared essentially as follows. 0.37 ml of Tham solution (tromethamine injection, NDC 0074-1593-04, Abbott Laboratories, North Chicago, Ill.), with the pH adjusted using acetic acid (AR Select, ACS, Mallinckrodt, Paris, Ky.) to a pH of 7.2±0.5, is admixed with 0.33 ml saline (0.9% sodium chloride injection, USP, Abbott Laboratories) and 0.30 ml water (sterile water for injection, USP, Abbott Laboratories). The solution can be sterilized by sterile-filtration.

Preparing an Aerosol Formulation for Pulmonary Delivery

The section considers methods and devices for producing a dry-powder or liquid-droplet aerosol for administering the surfactant formulation to the pulmonary surfaces of a subject.

FIG. 1 provides an overview of the processing steps and formulations in accordance with the invention. Box 10 labeled "surfactant mixture" refers to a mixture of phospholipid, spreading agent, and lung-surfactant protein. The surfactant mixture may be processing into a lipid-body formulation such as a liposome suspension. Box 12 labeled "surfactant formulation components" refers to other components of the surfactant mixture. An active agent is incorporated into the formulation.

As seen in FIG. 1, the active agent can be added to a preformed surfactant mixture, e.g., preformed liposomes, to form a surfactant formulation, or can be added directly to the surfactant mixture components, as at 12, to directly produce a surfactant formulation, indicated by box 14. The surfactant formulation may be well-defined lipid bodies, for example, liposomes that incorporate the active agent, lipid-crystal or amorphous lipid bodies containing both surfactant mixture and active agent components, a solution of the components in an organic solvent or organic/aqueous co-solvent, or a suspension in which some of the some are in lipid-body form, and other components in solute form. As will be appreciated from below, the only composition and structural requirements of the surfactant formulation is that be it can be converted or processed into a suitable aerosol-particle form containing all of the above lipid and drug components.

Considering now the various processing steps contemplated by the invention, box 16 labeled "lyophilized particles" refers to a processing step in which the surfactant formulation, preferably as a aqueous suspension of lipid bodies, is lyophilized to form a dry mass that is then comminuted, e.g. by grinding, to form a composition containing dry-powder particles having a mass median aerodynamic diameter in the 1-5 μm size range. The dry-powder particles, indicated at box 16, are then stored and employed in a suitable aerosolization device to produce a dry-particle aerosol suitable for inhalation treatment (box 26), or for suspension in a suitable solvent, for aerosolization as a particle suspension (box 24).

In another embodiment, the invention contemplates processing a liquid surfactant formation, indicated at box 20, by means of a user-controlled nebulizer or aerosolizer, to generate an aqueous droplet aerosol containing the surfactant formulation in lipid-body form. The surfactant formulation components of this embodiment can be present in ordered, crystalline, or amorphous lipid particles suspended in the aerosol droplets.

In still another embodiment, the surfactant formulation is processed by spray drying to produce spray-dried particles having the desired mass median aerodynamic diameter in the 1-5 μm size, as indicated at box 18. The spray dried particles may then be stored and employed by the user in an aerosolization device, as above, for inhalation therapy. As indicated, the powdered particles can be delivered as a dry-powder aerosol, or the particles can be suspended in an aqueous medium for aerosolization in aqueous droplet form. Alternatively, as illustrated by the direct link between boxes 14 and 26, a suitable surfactant formulation in liquid form, e.g., a formulation solution or suspension contained in a volatile biocompatible fluid, may be formed in an aerosolization process in which the particles formed are immediately inhaled for therapeutic delivery of the active agent.

The underlying basis of drug delivery by aerosol administration of the surfactant formulation of the invention, and methods of forming aerosols suitable for achieving those advantages are further described below. Applications of the invention, in delivering an active agent to the pulmonary tract in various therapeutic or diagnostic methods, are also considered below.

As noted above, the formulation of the invention can be prepared as a solution formulation or as a particulate formulation. The lipid components or the therapeutic agent, or both can also be incorporated into liposomal, crystalline, or amorphous lipid bodies suspended in an aqueous, organic, or mixed solvent.

A suspension of liposomes (lipid vesicles) may be made by a variety of techniques, such as those detailed in Szoka, F. Jr., et al., *Ann. Rev. Biophys. Bioeng.,* 9:467-508, 1980. Liposomal surfactant compositions of the present invention are generally sterile liposome suspensions. These liposomes may be multiple compartment or multilamellar vesicles, single compartment vesicles and macrovesicles. The multilamellar vesicles are generally the most common. Multilamellar vesicles (MLVs) can be formed by simple lipid-film hydration techniques, preferably under sterile condition.

One method for producing a liposomal surfactant composition involves dissolving the surfactant polypeptide in an organic solvent together with the selected phospholipids, and then combining the resulting solution with an aqueous buffer solution. The resulting suspension is then dialyzed to remove the organic solvent Alternatively, the organic solvent can be removed by evaporation and/or exposure to a vacuunl The dried lipid/polypeptide mixture thus produced is rehydrated in an aqueous buffer system to produce the liposomes (Olson, F., et al., *Biochim. Biophys. Acta,* 557:9-23, 1979).

Suitable buffers include Tris buffers, a Tham buffer system and the like used. Tham is a buffering agent also known as Tris, tromethamine, and tris(hydroxymethyl)aminomethane. In various preferred embodiments, the compositions have a pH range of about 6.5-8.0.

The liposomes may be sized by extruding the aqueous suspension of liposomes through a series of polycarbonate membranes having a selected uniform pore size. The pore size of the membrane corresponds roughly to the largest sizes of liposomes produced by extrusion through that membrane, particularly where the preparation is extruded two or more times through the same-sized membrane. The liposomes so produced can be in the range of 0.03 to 5 micron. Homogenization and sonication methods are also useful for down-sizing liposomes to average sizes of 100 nm or less (Martin, F. J., In: Specialized Drug Delivery Systems-Manufacturing and Production Technology, P. Tyle, ed., Marcel Dekker, New York, pp. 267-316,1990).

If it is desired to incorporate the therapeutic agent into the liposomes prior to liposome formation, this may be done by standard techniques. For example, if the liposomes are formed by lipid hydration, a hydrophobic drug can be included in the lipid mixture to be hydrated and a hydrophilic drug can be incorporated into the hydration solution. High encapsulation efficiency of hydrophilic compounds, e.g., proteins, can be achieved by employing the reverse evaporation phase method, in which drug-containing aqueous medium is added to partially evaporated lipid structures.

Another method for achieving high encapsulation efficiencies for hydrophilic drugs is by solvent injection, where a lipid solution in a volatile organic solvent, e.g., ether, is injected into an aqueous solution of drug. With continued injection of the lipid solution to high lipid concentration, very high encapsulation rates, e.g., 50% of greater, may be achieved.

The solvent injection method is illustrated more generally in FIG. 2A, which shows addition of an aqueous solution of hydrophilic drug or organic solution of hydrophobic drug to a co-solvent dispersion of lipids (containing the surfactant mixture components), concomitant with or followed by aqueous dilution and evaporation of the organic solvent, to form a bulk formulation of lipid particles, e.g., liposomes, with incorporated or encapsulated drug.

Alternatively, the active agent may be added to the preformed liposomes. In this case, the surfactant polypeptide-lipid mixture comprises pre-formed liposomes. If the compound is a hydrophobic compound, the compound may be simply contacted with the liposomes, for uptake into the bilayer membrane by partitioning out of aqueous phase medium. For ionizable, hydrophilic and amphipathic compounds, high internal encapsulation into preformed liposomes can be achieved by loading the drug against a pH or other ion gradient, e.g., an ammonium gradient, according to available methods.

The formulation of liposomes may be stored as a lipid suspension, for aerosolization in aqueous-droplet form, as indicated at 20, in FIG. 1, or the liposome formulation may be lyophilized, powdered, and administered as a dry-powder aerosol, as indicated at 16, 22 in FIG. 1. Alternatively, a liposome suspension may spray-dried, as at 18, forming dried lipid particles in powder form, for administration as a powdered aerosol.

Freeze drying (lyophiliion) is one standard method for producing a dry powder from a solution or a suspension. See, for example, Freide, M., et al., *Anal. Biochem*, 211(1):117-122, 1993; Sarbolouki, M. N. and T. Toliat, *PDA J. Pharm. Sci. Technol.*, 52(1):23-27, 1998). Following lyophilization, the dried surfactant formulation is comminuted, e.g., by grinding or other conventional means, to form desired size particles.

Recently, techniques that make use of the supercritical properties of liquefied gases have been employed in the generation of microparticles and powders containing therapeutic proteins (Niven, R. W., In: MODULATED DRUG THERAPY WITH INHHALATION AEROSOLS: REVISITED, A. J. Hickey, ed., Marcel Dekker, New York). Particles with preferred crystal habits and characteristics suitable for inhalation purposes can be prepared by these methods. Exemplary supercritical fluid processing techniques include: rapid expansion of supercritical fluids (RESS), the use of gas-antisolvent (GAS) precipitation to prepare particles, and the solution-enhanced dispersion of supercritical fluids (SEDS) (see, U.S. Pat. Nos. 5,301,644; 5,707,634; 5,770,559; 5,981,474; 5,833,891; 5,874,029, and 6,063,138).

Spray drying may also be used advantageously for producing dried lipid particles of desired sizes. (See, Master, K., SPRAY DRYING HANDBOOK, 5$^{th}$ edition, J. Wiley & Sons, New York 1991; Maa, Y. F. et al., *Pharm. Res.*, 15(5):768-775, 1998; Maa, Y. F., *Pharm. Dev. Technol.*, 2(3):213-223, 1997). Various spray-drying methods have been described in the patent literature, See, for example, U.S. Pat. Nos. 6,174,496; 5,976,574; 5,985,284; 6,001,336; 6,015,256; 5,993,805; 6,223,455; 6,284,282; and 6,051,257.

Figure 2A:
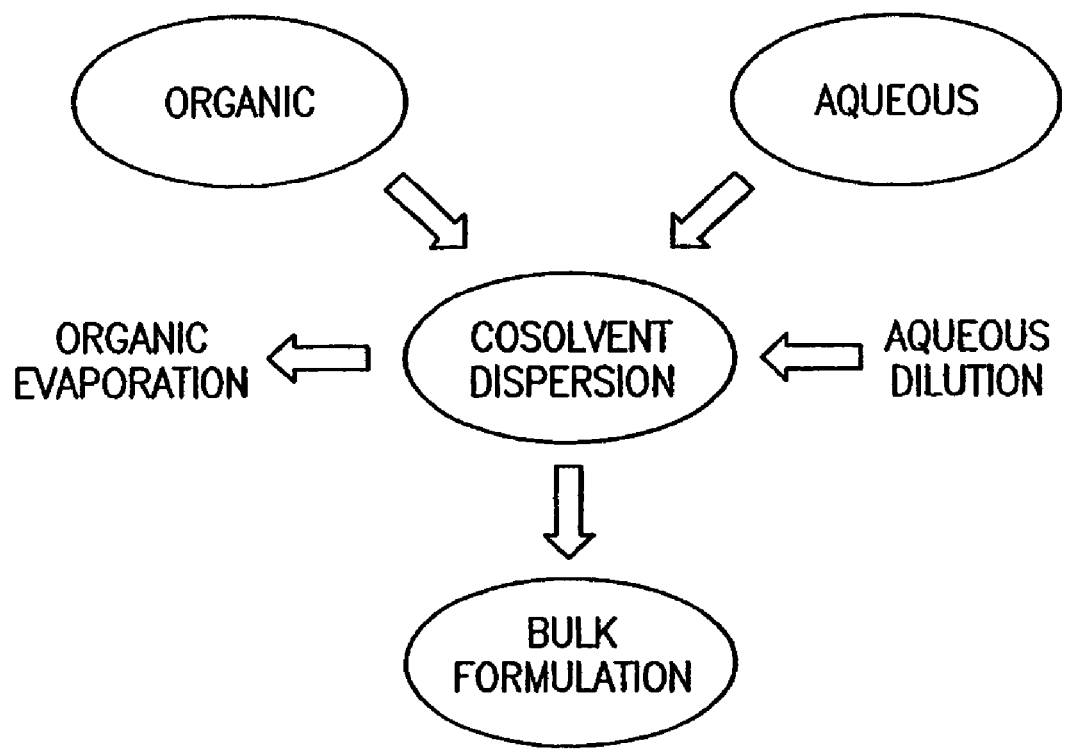
FIGS. 2A and 2B illustrate additional processing steps that can be practiced in the invention.
Figure 2B:
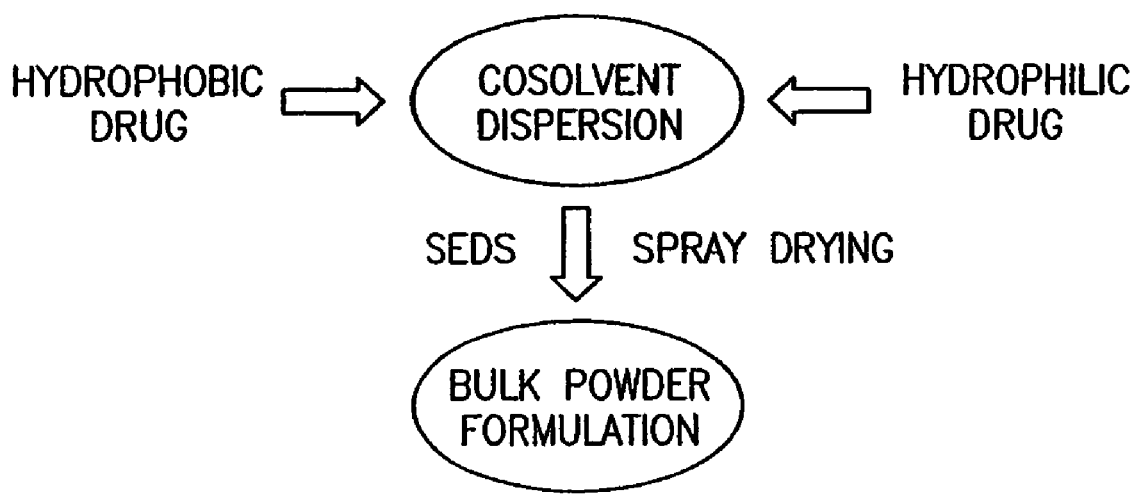

One spray-drying device that can be used is a cyclone drier that has a drying tank. The liquid mixture is fed into the drying tank and warm gas, e.g., air or nitrogen, or another inert gas is forced into the top of the tank. The feed liquid is broken up as it enters the tank, and dried by the warm gas as it is carried toward the bottom of the tank, and from there, to a collection unit. According to known processing parameters, the solvent, rate of injection, and rate of warm-gas flow can be adjusted to produce the desired-size dried particles. In this case, particles having a mean hydrodynamic diameter, for example, in the 1-5 μm range can be used. In the procedure, the drying temperature is at least about 37 degrees C., and preferably higher than 40 degrees C. and may be well over 100 degrees C. The temperature within the collection chamber is substantially lower than that of the heated air. This general method is illustrated in FIG. 2B, which shows a hydrophobic or hydrophilic drug added to a suitable co-solvent solution that also contains the surfactant-mixture components. The resulting mixture is spray dried to produce the desired-sized dry particles in a bulk powder formulation. These particles can then be packaged and stored, preferably under dry conditions, until use in an aerosolizer for administer the dried particles to the lungs.

Figure 3A:
FIGS. 3A and 3B are photomicrographs of amorphous (3A) and crystalline (3B) lipid-bodies.
Figure 3B:

FIGS. 3A and 3B are photomicrographs of dried lipid particles of the type that can be produced by this method. FIG. 3A shows amorphous particles having a variety of morphologies, although all within a narrow size range. The particles shown in FIG. 3B are crystaline powder particles with well-defined crystalline shapes. Both types of particles are suitable for the invention, although it is preferable that the particles, once formed, be maintained in the initial state, since transition between the two states can affect the chemical and physical stability of the active pharmaceutical ingredient and can directly influence the ability of powders to be dispersed and deaggregated from inhaler devices. These changes may also influence the pharmacokinetic properties of the particles. In general, the factors that influence the tendency of amorphous powders to undergo a transition to crystalline form include moisture, the presence of hydrophilic agents, impurities, temperature, and time. Factors that may reduce the tendency of amorphous particles to undergo transition to a crystalline state are the presence of protein and polymers, and hydrophobic materials. Of these several factors that affect transition, the most important are temperature and moisture, highlighting the need to store the particles, prior to aerosolization, in a dry state under moderate storage temperatures.

Regardless of the method of forming suspended or dried particles, the particles are formed under conditions that give a desired MMAD in the range 1-5 microns. Where the particles are intended to carry the active agent deep into the lungs, such as for treatment of a lung condition affecting tissues deep in the lungs (e.g. emphysema), the particles are preferably predominantly in the 1-3 or 1-2 micron MMAD size range. Where drug delivery is targeted to the airways, larger particle sizes, e.g., in the 3-5 MMAD size range, may be more appropriate.

Where the formulation is an aqueous suspension of liposomes or other lipid particles, a variety of commercial nebulizers may be used to produce the desired aerosol particles. Typically, the nebulizing oration is carried out at a pressure of about 10-50 psig, and the aqueous particles formed are typically in the range of about 2-6 microns. The device may be controlled to produce a measured quantity of aerosolized liposomes or lipid-based particles, according to known operational variables.

Another device suitable for aerosolizing an aqueous suspension of liposomes, and preferably a relatively dilute suspension containing less than about 25%-30% encapsulated aqueous volume, uses ultrasonic energy to break up a carrier fluid into a fine mist of aqueous particles. The ultrasonic nebulizer device has been found to produce a liposome aerosol mist whose particle sizes are about the same as those formed by a compressed air nebulizer, i.e., between about 2-6 microns.

For aerosolizing a concentrated liposome dispersion of the type used for delivery of a water-soluble, liposome-permeable drug, the dispersion is first mixed with a carrier solvent, to form a diluted dispersion that can be aerosolized. The carrier solvent may be an aqueous medium, in which case the dispersion is diluted or adapted to a form suitable for spraying, such as by a pneumatic or ultrasonic nebulizer. The amount of additive added is sufficient to render the dispersion suitable for spraying and, for example, contains less than about 30% total encapsulated volume. Assuming the dispersion has an initial encapsulated volume of 70-75% of the total dispersion volume, it can be appreciated that a given volume of the dispersion must be diluted with at least one and two volumes of diluent.

Alternatively, the surfactant components may be dissolved or suspended in a suitable volatile, biocompatible solvent, such as given below, and sprayed from a suitable aerosolizer device under conditions that (i) lead to initial formation of spray dried particles and (ii) inhalation of the just-formed particles into the lungs.

This section describes various self-contained delivery devices designed for producing an airborne suspension of the dried lipid particles. As defined herein "self-contained" means that the particle aerosol is produced in a self-contained device that it propelled by a pressure differential created either by release of a pressurized fluorochlorocarbon propellant or by a stream of air drawn through or created in the device by the user. It will be appreciated that conventional powered aerosolizers for dry powders are also suitable.

Lipid particle propellant suspension. This apparatus, or system uses a conventional pressurized propellant spray device for delivering a metered amount of dried lipid particles that are suspended in the propellant Because the system requires long-term suspension of lipid particles, e.g., liposomes, in a suitable propellant, the lipid particles and propellant components of the suspension must be selected for stability on storage.

Several fluorochlorocarbon propellant solvents have been used or proposed for self-contained inhalation devices. Representative solvents includes "Freon 11" ($CCl_3F$), "Freon 12" ($CCl_2F_2$), "Freon 22" ($CHClF_2$), "Freon 113" ($CCl_2FCClF_2$), as well as others. To form lipid-particle/propellant suspension, the dried lipid particles are added to the selected propellant or propellant mixture, to a final lipid particle concentration of about 1 to 30, and preferably between about 10-25 percent by weight by weight of the total propellant. Where the drug is a water-soluble compound that remains encapsulated in the dried lipid particles of the propellant suspension, the final concentration of lipid particles in the propellant is adjusted to yield a selected metered dose of the drug, in a given aerosol suspension volume. Thus, for example, if liposomes are formulated to contain 0.05 mg drug per mg dried liposome preparation, and the selected dose of drug to be administered is 1 mg, the suspension is formulated to contain 20 mg of dried liposomes per aerosol dose.

For a lipid-soluble drug, i.e., one that is readily soluble in the propellant solvent, two formulation approaches are possible. In the first, the drug is initially included in the lipids used in forming the dried lipid particles, and these are then added to the propellant in an amount that gives a selected concentration of drug/volume of propellant, as above. Alternatively, the drug may be added initially to the solvent, at a selected drug concentration. The lipid particles in this formulation are "empty" dried particles that will act as a lipid reservoir for the drug during aerosol formation and solvent evaporation. The final concentration of empty lipid particles is adjusted to give a convenient total lipid dose that is suitable for holding the metered amount of drug.

Lipid-particle entrainment in a propellant. In this apparatus, or system, dried lipid particles containing a metered-dose quantity of drug are prepackaged in dehydrated form in a delivery packet. The packet is used with a propellant spray device, to eject the liposome contents of the packet in an airborne suspension of liposome particles.

Lipid-particle entrainment in air. A third type of delivery apparatus or, system uses an air stream produced by user inhalation to entrain dried lipid particles and draw these into the user's respiratory tract. In operation, a packet is placed on the nozzle, preferably in a manner that ruptures the seal at the "inner" end of the packet, as above, and the other end of packet is unsealed. The user now places his lips about the mouthpieces and inhales forcefully, to draw air rapidly into and through a pipe in the inhaler. The air drawn into the pipe becomes concentrated at the nozzle, creating a high-velocity air stream that carries lipid particles out of the packet and into the convection region. The air stream and entrained liposomes impinge on the paddle, causing it to rotate and set up a convection current. The lipid particles are thus distributed more evenly, and over a broader cross section, just prior to being drawn into the user's respiratory tract by inhalation.

Alternatively, the lipid particles could be retained within a device that provides the force required to disperse and aerosolize the powder independent of the inhaled breath of the patient. The timing of dosing within the inhalation maneuver may also be controlled by sensors incorporated within the delivery system.

The following examples are intended to illustrate, but not limit, the present invention.

EXAMPLE 1

Preparation of Surfactant Protein/Polypeptide

Synthesis of a surfactant polypeptide of the present invention, e.g. $KL_4$, may be carried out according to a variety of known methods of synthesis. The following procedure is described as exemplary.

Alternatively, the following procedure is also used as described herein. Chemicals and reagents useful in synthesizing batches of surfactant peptides, e.g., batches of $KL_4$ peptide, include the following:

- t-Doc-L-lysine(Cl-Z) PAM-resin (t-Bcc-L-Lys (CI-Z) (Applied Biosystems, Foster City, Calif.);
- a-Boc-ϵ-(2-Chloro-CBZ)-L-Lysine (Bachem, San Diego, Calif.);
- N-Boc-L-Leucine-$H_2O$(N-Boc-L-Leu; Bachem);
- Dichloromethane (DCM; EM Science, Gibbstown, N.J., or Fisher, Pittsburgh, Pa.);
- Trifluoroacetic acid (TFA; Halocarbon);
- Diisopropylethylamine (DIEA; Aldrich, Aldrich, Mich.);
- N,N-Dimethylformamide (DMF; EM Science, Gibbstown, N.J.);
- Dimethylsulfoxide (DMSO; Aldrich);
- N-Methylpyrrolidone (NMP; Burdick Jackson, Muskegon, Mich.);
- 1-Hydroxybenzotriazole hydrate (HOBt; Aldrich);
- 1,3-Dicyclohexylcarbodiimide (DCC; Aldrich);
- Acetic anhydride ($Ac_2O$; Mallinckrodt, St. Louis, Mo.); and
- Hydrogen fluoride (HF; Air Products, Allentown, Pa.)

One means of synthesizing $KL_4$ peptide is performed on a Coupler 296 Peptide Synthesizer (Vega Biotechnologies, Tucson, Ariz.) using the Merrifield method. A "typical" synthesis is described as follows. Chain elongation was carried out on 100 g of lysine PAM-resin by the procedure described in Table 2 below. All steps except steps 7, 10 and 11 were done automatically.

TABLE 2

Program for a Cycle Using the HOBt Active Ester Procedure

| Step | Reagent | Time | Volume |
|---|---|---|---|
| 1 | 50% TFA/$CH_2Cl_2$ | 1 × 2 min | 1.8 liters |
| 2 | 50% TFA/$CH_2Cl_2$ | 1 × 20 min | 1.5 liters |
| 3 | $CH_2Cl_2$ | 5 × 20 sec | 1.7 liters |
| 4 | 5% DIEA/$CH_2Cl_2$ | 1 × 2 min | 1.7 liters |
| 5 | 5% DIEA/NMP | 1 × 3 min | 1.7 liters |
| 6 | DMF | 5 × 30 sec | 1.7 liters |
| 7 | BOC AA-HOBt active ester | 1 × 39 min | 1.0 liters |
| 8 | DIEA/DMSO (195 ml/285 ml) | 1 × 21 min | 0.5 liters |
| 9 | DMF | 3 × 30 sec | 1.7 liters |

TABLE 2-continued

Program for a Cycle Using the HOBt Active Ester Procedure

| Step | Reagent | Time | Volume |
|------|---------|------|--------|
| 10 | 10%; AC$_2$O/ 5% DIEA/NMP | 1 × 8 min | 2.0 liters |
| 11 | CH$_2$Cl$_2$ | 3 × 30 sec | 1.7 liters |

While the peptide-resin was being deprotected, the appropriate amino acid derivative was being made. The appropriate amino acid was dissolved in one (1) liter of NMP. After a clear solution was obtained, HOBt was added to the solution. When the HOBt was dissolved, DCC was added to the solution. This solution was left stirring for one (1) hour at room temperature. During this one hour of stirring, a by-product formed, dicyclohexylurea (a white precipitate). This by-product was filtered off through a buchner funnel using Whatnan's #1 filter paper. The filtrate was then added manually to the contents of the Vega 296 reaction vessel at step No. 7.

The synthesizer was then programmed to stop after the completion of step No. 9. Aliquots of the peptide resin were subjected to the quantitative ninhydrin test of Sarin et al. (Applied Biosystems 431A user manual, Appendix A). The coupling efficiencies were good throughout the entire synthesis. The unreacted peptide resin was acetylated after leucine 12 (cycle 9) and after leucine 5 (cycle 16). After each acetylation, the peptide resin was washed with dichloromethane (see Table 2, step 11).

At the end of the synthesis, the completed peptide resin was deprotected (removal of the Boc group) by completing steps 1-3 of the program (see Table 2). The deprotected peptide resin was then washed with ample volumes of absolute ethanol and dried in vacuo over P$_2$O$_5$. The weight of the dried, deprotected peptide resin was 256.48 grams. Since the batch was started with 100 g of t-Boc-Lysine (CI-Z) OCH$_2$ PAM resin at a substitution of 0.64 mmoles/gram, the load corresponded to 64 mmoles. Subtracting out the initial 100 grams of resin, the weight gain was 156.48 grams. The molecular weight of the nascent protected peptide (excluding the C-terminal lysine anchored onto the resin) was 3011.604 g|mole.

HP Cleavage. The 256.48 gram lot of peptide resin was treated with hydrogen fluoride (HF) in three large aliquots. A Type V HF-Reaction Apparatus from Peninsula Laboratories (Belmont, Calif.) was used for the cleavage of the peptide resin using liquid hydrogen fluoride. The anisole was distilled before use. HF was used without any treatment. Dry ice, isopropanol and liquid nitrogen are required for cooling purposes.

For the first HF, approximately 88 g of the KL4 peptide resin was placed into the one-liter reaction vessel with a magnetic stir bar. Twenty-five ml of distilled anisole was added to the peptide resin. After the entire system was assembled and leak-tested, HF was condensed into the reaction vessel until the overall level reached about 300 ml. Cleavage of the peptide from the resin was allowed to proceed for one hour at −4° C. Partial removal of HF was done by water aspirator for 1-2 hours. After the 1-2 hours, the rest of the HF was removed by high vacuum (mechanical vacuum pump) for 1-2 hours. The temperature of the reaction vessel remained at −4° C. throughout the HF removal process.

The HF apparatus was then equilibrated to atmospheric pressure and an oily sludge was found at the bottom of the reaction vessel. Cold anhydrous ether (700 ml, prechilled to −20° C.) was added to the contents of the reaction vessel. The resin clumps were triturated with ether using a glass rod. The ether was decanted after the resin settled. The resin was then washed with 500 ml of room temperature anhydrous ether and allowed to stir for about 5 min. The ether was decanted after the resin settled. The resin was washed until it became free-flowing (4-5 total washes). The resin was left in the fume hood to dry overnight.

The resulting dried HF-treated resin was then weighed and stored in the freezer. 1.021 grams of the dried HF-treated resin was removed and extracted with 50 ml of 50% acetic acid/water and allowed to stir for 30 min. The resin was filtered through a coarse sintered glass funnel, and the filtrate was collected in a lyophilizing jar. The filtrate was diluted with approximately 200 ml of water, shell frozen, and placed on the lyophilizer. The one (1) gram of extracted HF-treated resin yielded 569 mg of crude peptide. The following table (Table 3) summarizes the large scale HF treatments of the remaining KL$_4$ peptide resin. All of the HF-treated resins were stored in the freezer.

TABLE 3

| HF# | Wt. of Resin | Amt. of Anisole | Total Volume (HF + Anisole + Resin) |
|-----|--------------|-----------------|-------------------------------------|
| 1 | 88.07 g | 25 ml | 300 ml |
| 2 | 85.99 g | 25 ml | 300 ml |
| 3 | 79.35 g | 25 ml | 300 ml |

Purification. The peptide was purified using a Dorr-Oliver Model B preparative HPLC (Dorr-Oliver, Inc., Milford, Conn.). This unit was connected to a Linear Model 204 spectrophotometer and Kipp and Zonen dual channel recorder. This preparative BPLC was interfaced with a Waters KIL250 Column Module (Waters Associates, Milford, Mass.) containing a radially compressed 10×60 cm cartridge filled with Vydac C$_4$ support, 15-20 microns, and 300 A pore size (Vydac, Hesperia, Calif.). Solvent "A" consisted of 0.1% HOAc in water, and solvent "B" consisted of 0.1% HOAc in acetonitrile. The flow rate was set at 400 ml/min, the cartridge was compressed to 150-200 psi, and the preparative HPLC system back pressure was at 550-600 psi.

For the first Dorr-Oliver run, 20 g of the HF treated resin from HF#1 was extracted in 500 ml of glacial acetic acid for five minutes. Water (500 ml) was added to the resin/acetic acid mixture. This 50% acetic acid/water solution was stirred for an additional 25 minutes. The resin was filtered off with a coarse sintered glass funnel. The peptide-containing filtrate was saved and loaded onto the Dorr-Oliver. The HPLC gradient used was 1-40% "B" in 45 minutes, then held isocratically for seven minutes. At this point, the percent "B" was increased 1% per minute to a final percentage of 44% (not shown).

Fractions were collected manually and were analyzed by HPLC. All fractions that met a purity of ≧95% were pooled together and stored in a large glass container. This material was subsequently referred to as "BPS #1." All fractions that had the desired component, but did not meet the 95% or better purity, were collected and later recycled. At least 10 additional preparative HPLC runs were performed on the Dorr-Oliver unit (data not shown).

Reverse Osmosis, Lyophilization. The total volume of BPS #1 was approximately 60 liters. Reverse osmosis was used to concentrate the peptide solution to a final volume of two liters. A Millipore Model 6015 Reverse osmosis Unit with an R74A membrane to retain the peptide was used. The resulting two liters of BPS #1 were filtered through a buchner funnel using two pieces of Whatman #1 filter paper, divided into approximately 11 lyophilizing jars and diluted with equal volumes of water. The lyophilizing jars were shell-frozen and lyophilized. The total weight of dry $KL_4$ peptide at the end of the procedure was 40.25 g.

Re-lyophilization. It has been found that different lyophilizing conditions (e.g. peptide concentration, composition of solvents to be lyophilized, length of the lyophilization step, shelf temperature, etc.) can result in dried preparations having differing solubility characteristics. It is desirable that the dry $KL_4$ peptide be soluble in a chloroform:methanol (1:1) solution at 1 mg/ml and ≧90% soluble at 10 mg/mL If these criteria are not met at the end of the lyophilization step noted above, the peptide can be re-lyophilized.

A typical re-lyophilization is described as follows. Approximately 5 g of peptide is slowly added to two liters of acetonitrile stirring in a glass flask. After approximately one minute, three liters of Milli-Q water is added, followed by 50 ml of acetic acid (final concentration of acetic acid=1%). This is stirred for three days at 37° C., filtered through Whatman #1 filter paper in a buchner funnel, and placed into a lyophilization jar. It is then shell frozen using dry ice and isopropyl alcohol and placed on the lyophilizer. Lyophilization time may vary from three to seven days. The final dry product is then weighed, packaged, and aliquots taken for solubility and chemical analyses.

EXAMPLE 2

Preparation of Model Surfactant Mixture

Materials. 1,2-dipalmitoyl phosphatidylcholine (DPPC), 1-palmitoyl, 2-oleoyl phosphatidylglycerol (POPG), and palmitic acid (PA) were obtained from Avanti Polar Lipids Inc. (Birmingham, Ala.). The KL4 polypeptide with the amino acid sequence KLLLLKLLLLKLLLLKLLLLK (SEQ ID NO:1) was synthesized as described herein or obtained from Discovery Laboratories, Inc., (Doylestown, Pa.). All salts, buffers and organic solvents used were of the highest grade available.

A stock solution of surfactant composition was formulated to contain 40 mg/mL total phospholipid, with a composition based on the following formula $PL_T$=total phospholipid=DPPC+POPG

3 DPPC:1 POPG

1 $PL_T$: 0.15 PA:0.027 $KL_4$ peptide.

Using the foregoing formula, surfactant compositions were made that contained varying amounts of palmitic acid (PA) and the $KL_4$ peptide in 2.5 to 30 mg per mL of total phospholipids (Table 4).

TABLE 4

| Component | 2.5 mg/mL | 10 mg/mL | 30 mg/mL |
|---|---|---|---|
| DPPC | 1.875 mg | 7.5 mg | 22.5 mg |
| POPG | 0.625 mg | 2.5 | 7.5 mg |
| PA | 0.375 mg | 1.5 | 4.5 mg |
| $KL_4$ Peptide | 0.067 mg | 0.267 | 0.801 mg |

A Model Surfactant Mixture was made as follows. $KL_4$ peptide (9 mg), DPPC (225 mg), POPG (75 mg) and PA (45 mg) were dissolved in 2.5 milliliters (ml) of 95% ethanol at 45° C. This solution was then added to 7.5 ml of distilled $H_2O$ at 45° C. with rapid vortexing and 2 ml of 500 mM NaCl, 250 mM Tris-acetate pH 7.2 was added. The resulting milky suspension was stirred at 37° C. for 15 minutes and the ethanol present was then removed by dialysis (Spectrapor 2; 13,000 mol. wt. cutoff) against 100 volumes of 130 mM NaCl, 20 mM Tris-acetate pH 7.2 buffer at 37° C. Dialysis was continued for 48 hours with two changes of the dialysis solution.

In addition, the composition may further comprise a buffer system/suspension having the following composition per mL of finished product (Table 5).

TABLE 5

| Component | Amount per mL |
|---|---|
| Tromethamine, USP | 2.42 mg |
| Glacial acetic acid, USP or NaOH, NF | quantity sufficient to adjust tromethamine buffer to pH 7.7 |
| NaCl, USP | 7.6 mg |
| Water for injection, USP | quantity sufficient to 1.0 mL |

This Tham buffered system was prepared essentially as follows. 0.37 ml of Tham solution (tromethamine injection, NDC 0074-1593-04, Abbott Laboratories, North Chicago, Ill.), with the pH adjusted using acetic acid (AR Select, ACS, Mallinckrodt, Paris, Ky.) to a pH of 7.2±0.5, was admixed with 0.33 ml saline (0.9% sodium chloride injection, USP, Abbott Laboratories) and 0.30 ml water (sterile water for injection, USP, Abbott Laboratories). The solution was sterile-filtered.

EXAMPLE 3

Colorimetric Assay for Human Neutrophil Elastase

A peptide having the following sequence MeO-Suc-Ala-Ala-Pro-Val-pNA (SEQ ID NO:24) was used as an elastase substrate. One hundred (100) μL of a 0.425 mM solution of the SEQ ID NO:24 peptide substrate was placed in a series of microtiter plate wells. Varying amounts of human neutrophil elastase (HNE) were added to the microtiter plate wells. The optical density at 410 nM ($OD_{410}$) was used to measure elastase activity, and the optical densities observed were plotted versus the amounts of HNE added to generate a standard curve.

EXAMPLE 4

Inhibition of Human Neutrophil Elastase by an Elastase Inhibitor

To test the ability of a serine elastase inhibitor to inhibit human neutrophil elastase (HNE), a standard amount of 0.125 μg HNE was mixed with increasing amounts of a serine elastase inhibitor before addition of the elastase substrate described in Example 3. The inhibition curve that is plotted in FIG. 5A shows a linear response between the log of the amount of inhibitor and the resulting $OD_{410}$.

EXAMPLE 5

Elastase Activity in BAL Fluid from Patient with ARDS

Bronchoalveolar lavage (BAL) fluids were recovered from humans with acute respiratory distress syndrome (ARDS). A colorimetric assay for elastase activity was performed using different amounts of BAL fluid. The dose-response curve between the amount of BAL added to the sample and the $OD_{410}$ is plotted in FIG. 5B.

Lavage fluids from other ARDS patients had varying amounts of elastase activity.

EXAMPLE 6

Elastase Activity in Rabbit BAL Fluids

Six rabbits were treated with 3 mg anti-BSA/kg (rabbits 6098 and 6099) or 5 mg anti-BSA/kg (rabbits 6100-6103) was instilled intratracheally and 10 mg of BSA was given intravenously (6098-6101) to induce respiratory distress. Bronchoalveolar lavage (BAL) fluids were taken from the lungs of these rabbits six hours after the treatment and a colorimetric assay of elastase activity was performed on these BAL fluids. Elastase activity is expressed as the concentration of HNE that gives a corresponding OD at 410 nm.

Additionally, the same assay was performed after the addition of 100 μg/ml of a serine elastase inhibitor to the BAL fluids. The serine elastase inhibitor used in this study specifically inhibits HNE. FIG. 6A graphically illustrates these results. In all cases, the elastase activity was inhibited, confining that the measured proteolytic activity was due to HNE.

EXAMPLE 7

Evidence of Elastase Inhibitor in Rabbit BAL Fluids

Figure 6B:
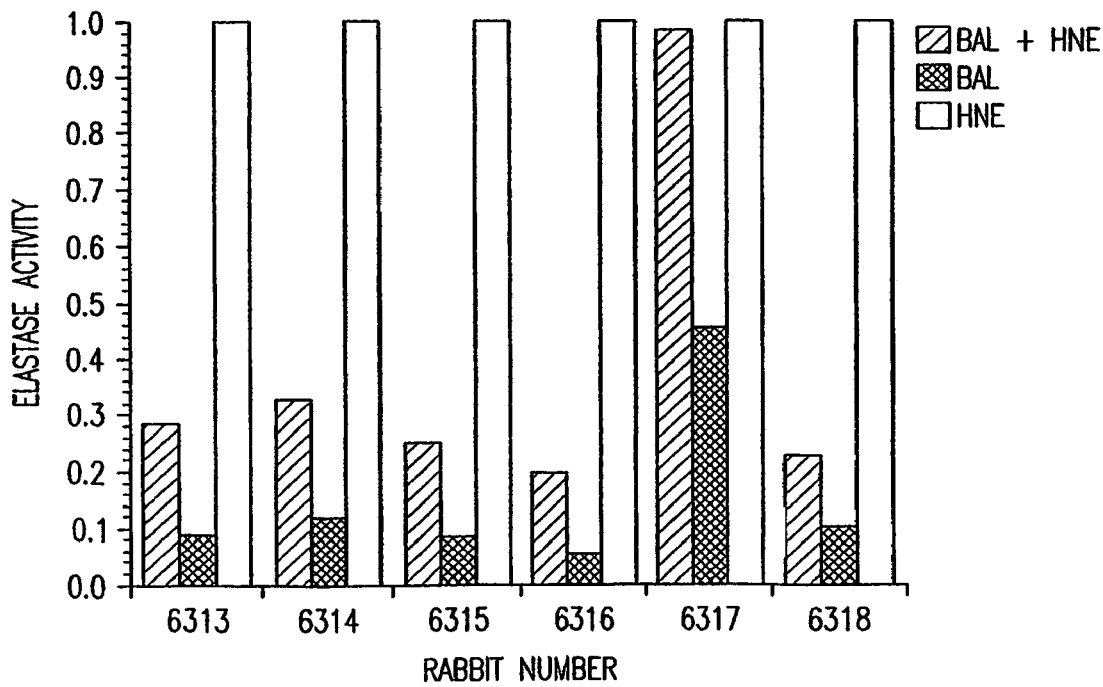
FIG. 6B shows the inhibition of human neutrophil elastase (INE) activity by bronchoalveolar lavage (BAL) fluids from rabbits undergoing pulmonary injury. The BAL fluids were taken from rabbits at 3 hour (rabbits 6315 and 6316) or 6 hour (6313, 6314, 6317, and 6318) after they were given bacterial lipopolysaccharide (LPS) and anti-BSA intratracheally (all animals); animals 6317 and 6318 additionally received 10 mg/kg of BSA at 3 hours. BAL fluids were tested alone (bars with crosshatching) or after addition to 1 μg/ml HNE (bars with crosshatching). The open bar shows the activity of HNE without added BAL fluids. Significant free elastase was present in animal 6317; all others showed the presence of an inhibitor of elastase.

Six rabbits received bacterial lipopolysaccharide (LPS) and anti-BSA intratracheally to induce respiratory distress. Animals 6317 and 6318 additionally received 10 mg/kg of BSA at 3 hours. BAL fluids were taken from rabbits 6315 and 6316 at three (3) hours and from rabbits 6313, 6314, 6317, and 6318 at six (6) hours after the first anti-BSA dosage. BAL fluids were tested alone (cross-hatched) or after addition to 1 μg/ml HNE (Solid). The results are presented graphically in FIG. 6B. Significant free elastase was present in animal 6317; all others showed the presence of an inhibitor of elastase.

EXAMPLE 8

Model Surfactant Mixture and Serine Elastase Inhibitor Reduce the Amount of Protein Detected in BAL Fluids of Lungs During Inflammation Materials:

LPS: Minn (List Biological). 5 mg vial. Animals were treated by quantitative lavage leaving 120 μg/kg in 8 ml/kg.

PMA: (Sigma) diluted in saline or Model surfactant mixture to 5 μg/mL Used 20 ml/kg/rabbit for lavage, leaving 20% of the dosage in the animal.

Model surfactant mixture: (Discovery Labs) 10 mg/ml. Use 20 ml/kg/rabbit for lavage, leaving 20% of the dosage in the animal.

Serine Elastase Inhibitor. Elafin (Astra-Zeneca) 3 mg/ml stock, dialyzed against saline to remove azide: 1.3 ml/kg Elafin was administered intravenously at 1.5 hr., 0.33 ml/kg was administered intratracheally (×2 sides) at 3 hr., and 0.66 ml/kg was administered intravenously at 4.5 hr.

$^{125}$I-BSA: (NEN) Diluted in 200 μg/ml BSA/saline to 20 μCi/ml. Used 0.4 ml/kg intravenously 30 minutes before sacrifice.

Rabbits: 10 NZW rabbits, either sex, 2.0-2.5 Kg.

Procedure:

Twenty NZW rabbits are divided into five (5) treatment groups with four (4) animals each. Lung injury is induced by two lavages with LPS in saline and one PMA treatment administered by lavage at 3 hr. Serine elastase inhibitor and Model surfactant mixture were separately and jointly tested to ascertain the degree to which these factors could reduce symptoms of inflammation. Treatments received by the different groups are as follows:

Group 1: The animals received two lavages with LPS in saline and one PMA treatment administered by lavage at 3 hr. A dosage of $^{125}$I-BSA was given to the animals intravenously at 5.5 hr. and the animals were sacrificed at 6 hr.

Group 2: The animals received two lavages with LPS in saline, one PMA and Model surfactant mixture treatment administered by lavage at 3 hr. A dosage of $^{125}$I-BSA was given to the animals intravenously at 5.5 hr. and the animals were sacrificed at 6 hr.

Group 3: The animals received two lavages with LPS in saline and one PMA treatment administered by lavage at 3 hr. Three doses of a serine elastase inhibitor were given at 1.5, 3.0, and 4.5 hr and a dose of $^{125}$I-BSA was given to the animals intravenously at 5.5 hr. The animals were sacrificed at 6 hr.

Group 4: The animals received two lavages with LPS in saline and one PMA and Model surfactant mixture treatment administered by lavage at 3 hr. Three doses of a serine elastase inhibitor were given at 1.5, 3.0, and 4.5 hr and a dose of $^{125}$I-BSA was given to the animals intravenously at 5.5 hr. The animals were sacrificed at 6 hr.

Group 5: Normal animals used as control. The animals were sacrificed 30 minutes after receiving a dose of $^{125}$I-BSA.

All animals were maintained on ventilators receiving room air at low ventilatory pressures. If, immediately after lavages, an animal required higher pressures and/or oxygen to maintain $SaO_2$ of greater than about 80, higher positive end-expiratory pressure (PEEP) and/or oxygen therapy was given for a period of time.

After the animals were sacrificed, the lungs were removed and the left main bronchus tied off. The right lower lobe was lavaged three (3) times with 10 ml saline each time. The three lavages (terminal lavage) were pooled for each animal and 5 μl of 20 mM BHT was added to each pooled lavage to prevent oxidation. Cells in the terminal lavage pool were removed by centrifugation at 1000 rpm for 10 min. Surfactant pellets and a protein-rich supernatant were then prepared by centrifugation at 40,000 g for 15 minutes. Sections of the left lung were preserved in formalin, others were frozen. The protein content and the red blood cells (RBC) in the terminal lavages were analyzed.

The protein content in the terminal lavages indicates a level of injury to the basement membrane matrix that allows plasma proteins to leak through into the alveolar space. As the amount of protein in the terminal lavages increased, more injury was observed in the lungs. The amount of protein found in the terminal lavage fluids for each treatment group is graphically presented in FIG. 7A. The results show that the amount of protein (approximately 2.5 mg/ml) resulting from the LPS and PMA injury was reduced in the group receiving Model surfactant mixture, and even further reduced in the group that received Model surfactant mixture and elastase inhibitor. The failure of group 3, which received elastase inhibitor alone, to show a reduction in protein levels was most likely due to the abnormally high value obtained for one animal in the group (see figure description). If this animal was excluded, the mean value for group 3 is then 1.72 mg/ml, approximately equal to the value obtained for the group 2 that was treated with Model surfactant mixture alone. The error bars depict SEM.

EXAMPLE 9

Basement Membrane Protein Fragments are Present in BAL Fluids of Lungs During Inflammation LPS and PMA injury in rabbits was shown in Example 8 to cause release of proteins and their proteolytic fragments. Western blot analyses were performed on the proteins present in the terminal lavage fluids of the test rabbits, after electrophoretic separation on SDS polyacrylamide gels. Antibodies produced in guinea pigs against basement membrane matrix proteins were used to visualize and confirm the presence of basement membrane proteins in lavage fluids.

The results are shown in FIG. 7B. The components of pulmonary basement membrane matrix are shown in the left panel. The proteins and protein fragments in BAL fluids of representative rabbits treated with LPS and PMA alone (Group 1), or with the addition of Model surfactant mixture (Group 2), elastase inhibitor (Group 3), or both Model surfactant mixture and elastase inhibitor (Group 4) are shown in the Group 2-4 panels. Normal, uninjured, rabbit lavage is shown in the Group 5 panel. The low MW bands (<10,000 MW), which are absent in intact basement membrane matrix and the Group 5 panel, represent fragments of the basement membrane. The large band present at 70,000 MW in Groups 1-4 is albumin, present as a contaminant in the antiserum used. The bands above 90,000 MW are specific to the basement membrane and not present in normal rabbit plasma (data not shown).

EXAMPLE 10

Model Surfactant Mixture and Serine Elastase Inhibitor Reduce Red Cell Counts in BAL Fluids During Inflammation of Lungs The amount of hemorrhage or red blood cells (RBCs) appearing in the terminal lavage fluid is another indicator of injury in the animals. While the presence of increased protein in the lavage fluid can indicate a level of injury to the basement membrane matrix, the presence of RBCs indicates an even larger degree of injury, one that allows whole blood cells to pass through holes created in the matrix.

RBC counts were performed on the terminal lavage fluids obtained in Example 8 and the average of the results obtained for the two animals in each group were plotted in FIG. 7C. A slight drop in the number of RBCs, suggesting some amelioration of injury, was seen when Model surfactant mixture was present, but a greater reduction in injury was seen when the serine elastase inhibitor was present. The addition of both Model surfactant mixture and the serine elastase inhibitor resulted in a significant reduction of injury as measured by the number of RBCs present in the terminal lavage fluid.

EXAMPLE 11

Inhibition of Human Neutrophil Elastase 0.02 μg of human neutrophil elastase (HNE), was incubated with 2 mg/ml of Model surfactant mixture, 100 μg/ml of a serine elastase inhibitor, or both Model surfactant mixture and the serine elastase inhibitor together. The HNE activity remaining was assayed using the calorimetric assay described above. The result is represented graphically in FIG. 8.

Significant inhibition was seen when the serine elastase inhibitor was added, with or without the additional presence of Model surfactant mixture. The data show that Model surfactant mixture does not interfere with the ability of the serine elastase inhibitor to inhibit elastase, nor does it itself directly inhibit elastase.

EXAMPLE 12

Inhibition of HNE by Elastase Inhibitor in BAL Fluid

The data presented above in Examples 8 to 10 suggested that the basement membrane matrix damage occurring in rabbit lungs in the 6 hours following injury with LPS and PMA might be inhibited in vivo by a serine elastase inhibitor and/or Model surfactant mixture. The presence of elastase inhibitor(s) (or the residual activity) in the terminal lavage fluids prepared as described in Example 8) was tested. 0.02 μg of human neutrophil elastase (HNE), was incubated with 50 μl of terminal lavage fluid of one representative rabbit from each experimental group (Groups 1-5). HNE activities are assayed using the colorimetric assay as described in Example 1. The assay results are presented graphically in FIG. 9.

Significant inhibition of HNE activity by BAL fluid was observed from animals in Groups 2, 3, or 4. The HNE elastase inhibition seen with the lavage fluids from Groups 3 and 4 that received a known elastase inhibitor by both intravenous and intratracheal routes was highly significant. The elastase inhibition seen for the Model surfactant mixture group (Group 2), may have been due to endogenous elastase inhibitors in the rabbit such as SLPI or alpha1 protease inhibitor, or some combination thereof. Normal rabbits (Group 5) and the LPS/PMA positive injury animals (Group 1) did not show the presence of elastase inhibitor in their terminal lavage fluids in this experiment. Rabbit #5541 (Group 1) did, however, show the presence of free elastase in the terminal BAL fluid; none was detected in the normal animal's BAL (Group 5).

EXAMPLE 13

Detection of Phospholipase $A_2$ ($PLA_2$) in Lavage Fluids

Materials and Methods

Terminal lavage fluid was collected from rabbits experiencing pulmonary injury initiated by the intratracheal administration of partially purified antibodies directed against BSA (anti-BSA antibodies). Palmitoyl, oleoyl phosphotidylglycerol (POPG, Avanti Polar Lipids) was added to the lavage fluid as a substrate for detecting PLA2 activity in the lavage fluid. Prior to addition of the POPG substrate, the mixture was adjusted to a final concentration of 10 mM $CaCl_2$, 100 mM KCl and 25 mM Tris-Cl, pH 8.5. This mixture was incubated at 37° C. Aliquots were removed over time and the amount of oleic acid released from the POPG substrate was measured by high pressure liquid chromatography (HPLC). The amount of oleic acid released was quantified from the height of the peak at 4.59 min elution time from a C-18 HPLC column, as measured by the absorbance at 207 nm.

Results

Figure 10:
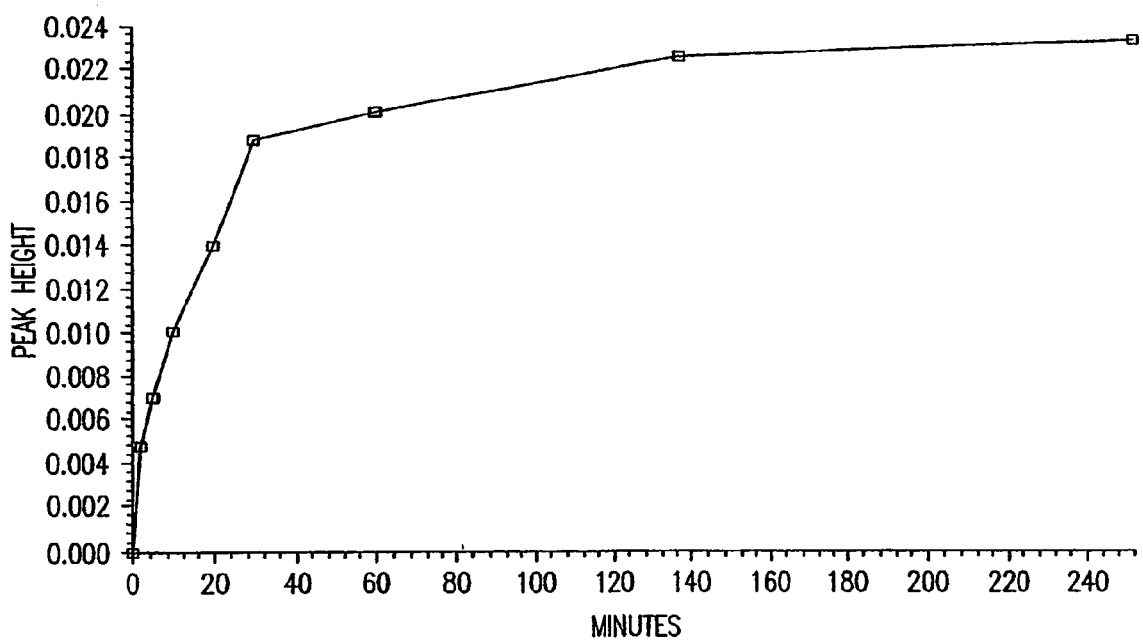
FIG. 10 illustrates that phospholipase $A_2$ ($PLA_2$) is present in lavage fluid from rabbits undergoing pulmonary injury induced by intratracheal administration of anti-BSA antibodies. The amount of oleic acid ("peak height) released from the $PLA_2$ substrate, palmitoyl, oleoyl phosphatidylglycerol (POPG) was plotted as a function of time. As shown, the amount of oleic acid released increased quickly from 0 to about 40 min.

FIG. 10 illustrates the rate of oleic acid release from POPG by lavage fluids from rabbit 6015. As illustrated, oleic acid is quickly released for about 40 min under the conditions employed. Such release of oleic acid from POPG indicated that PLA$_2$ was present in the lavage sample.

EXAMPLE 14

Lavage Fluid Phospholipase A$_2$ (PLA$_2$) Activity Correlates with Amount of Intratracheal Anti-BSA Administration Materials and Methods BSA was administered intravenously into six rabbits. The rabbits were lavaged once with 16 ml/kg saline followed by intratracheal instillation of varying amounts of anti-BSA antibodies, as follows:

Rabbits 6011 and 6012-2.5 mg/kg anti-BSA antibodies
Rabbits 6013 and 6014-5.0 mg/kg anti-BSA antibodies
Rabbits 6015 and 6016-12.5 mg/kg anti-BSA antibodies Terminal lavage fluids were collected and assayed for PLA$_2$ activity by detection of oleic acid produced in terminal lavage fluids as described in the previous Example.

The activity of PLA$_2$ in vivo was also detected by observing the endogenous appearance of free fatty acids (other than oleic acid) in the terminal lavage fluids that were collected. In particular, linolenic acid and linoleic acid have 3 and 2 sets of carbon-carbon double bonds that were readily distinguished from oleic acid and quantified by HPLC.

Results

Figure 11:
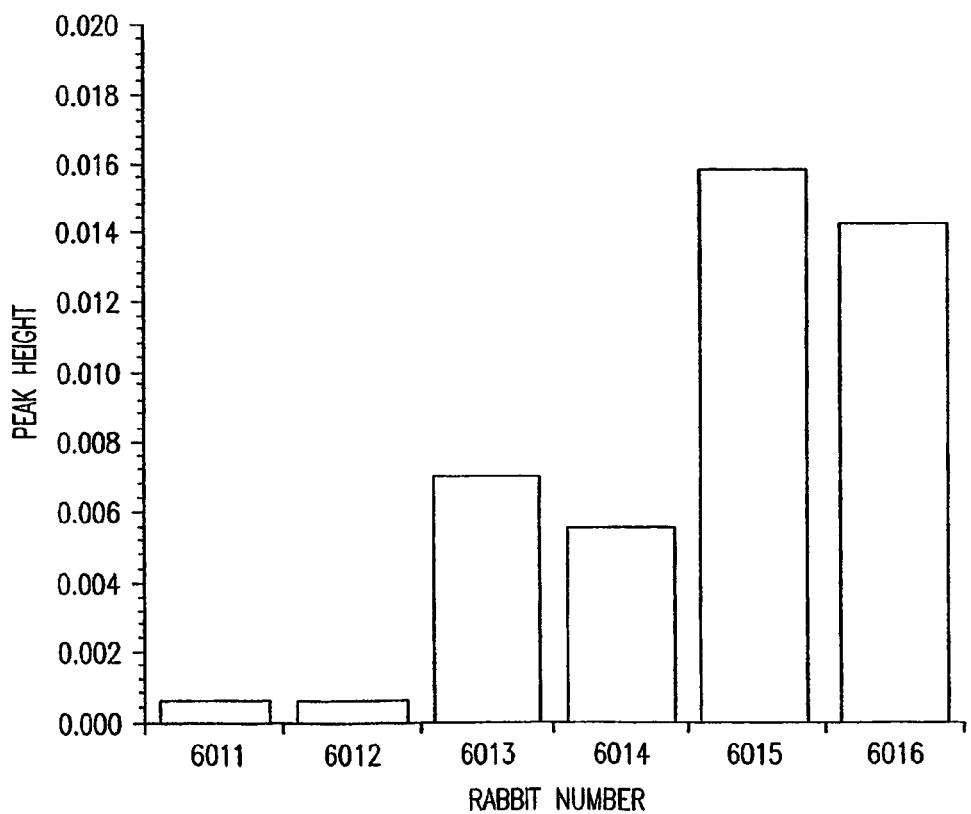
FIG. 11 graphically depicts the amount of phospholipase $A_2$ ($PLA_2$) activity in terminal lavage fluids isolated from animals that received 2.5 mg/ml of anti-BSA antibodies (animals 6011 and 6012), 5.0 mg/kg anti-BSA antibodies (animals 6013 and 6014) or 12.5 mg/kg anti-BSA antibodies (animals 6015 and 6016). As illustrated, the phospholipase $A_2$ ($PLA_2$) activity increases in terminal lavage fluids when the animals received increasing amounts of anti-BSA antibodies.

FIG. 11 shows the release of oleic acid from POPG after 30 min. incubation with lavage fluids obtained from rabbits 6011, 6012, 6013, 6014, 6015 and 6016. As shown, the amount of oleic acid released, and hence the extent of PLA$_2$ activity, is directly proportional to the amount of anti-BSA antibody preparation administered intratracheally to the animals. In other words, rabbits that received only 2.5 mg/kg anti-BSA antibodies, had lower levels of PLA2 activity than did rabbits that received 5.0 or 12.5 mg/kg anti-BSA antibodies. Accordingly, the degree of PLA2 activity increases with increasing levels of pulmonary injury.

Figure 12:
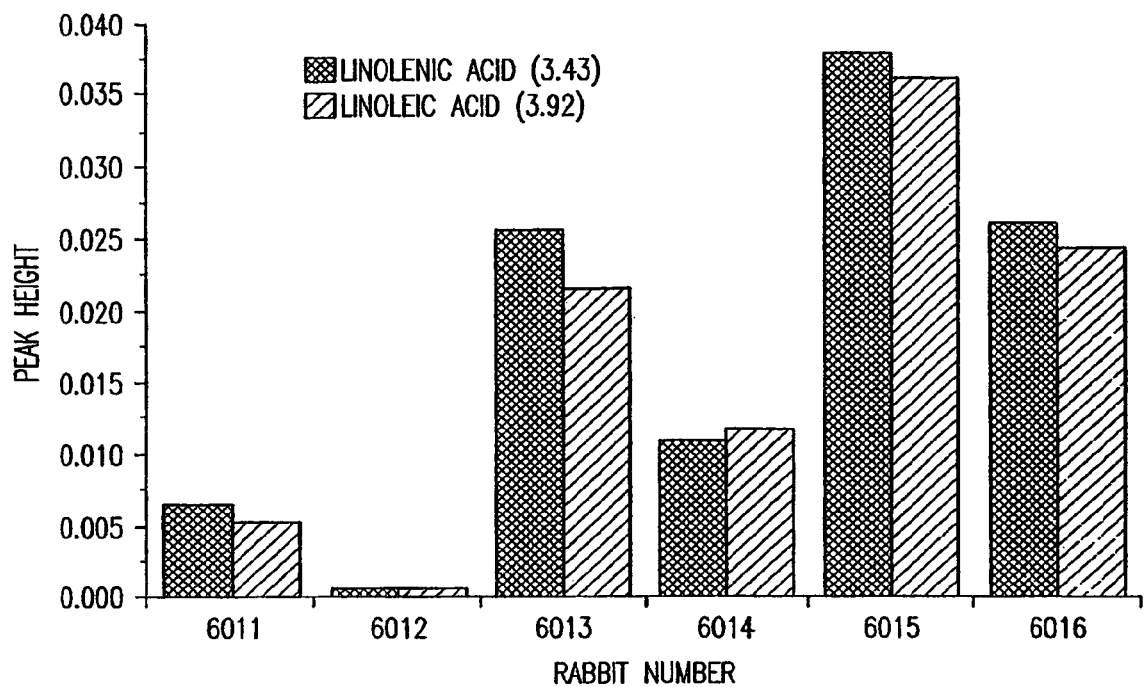
FIG. 12 graphically depicts the amount of linolenic acid (bars with crosshatching) and linoleic acid (bars with diagonal lines) present in terminal lavage fluids isolated from animals that received 2.5 mg/ml of anti-BSA antibodies (animals 6011 and 6012), 5.0 mg/kg anti-BSA antibodies (animals 6013 and 6014) or 12.5 mg/kg anti-BSA antibodies (animals 6015 and 6016). The presence of free fatty acids (linolenic acid and linoleic acid) in lavage fluids indicates that phospholipase $A_2$ (PLA2) is active in the injured pulmonary tissues of these animals. Also as illustrated, the amount of free fatty acids increased in animals that received greater amounts of anti-BSA antibodies.

FIG. 12 illustrates that phospholipids are broken down in vivo within injured pulmonary tissues. In particular, FIG. 12 shows the release of linolenic acid and linoleic acid from endogenous tissues as observed within terminal lavage fluids obtained from rabbits 6011, 6012, 6013, 6014, 6015 and 6016. As shown, the amount of linolenic acid and linoleic acid released, and hence the extent of PLA$_2$ activity, is again directly proportional to the amount of anti-BSA antibody preparation administered intratracheally to the animals.

EXAMPLE 15

Inhibition of Phospholipase A$_2$ (PLA$_2$) Activity in Lavage Fluids

Materials and Methods

BSA and anti-BSA antibodies were administered to rabbit 6015 and lavage fluids were obtained from rabbit 6015 as described in the previous Example. The compound 3-[3-(2-oxoethyl)-2ethyl-1-(phenylmethyl)-1H-indol-5-yl]oxy]propyl phosphoric acid (LY311727, Eli Lilly Co., Indianapolis, Ind.) was used as a PLA$_2$ inhibitor to further confirm that the appearance of fatty acids in lavage fluids was due to PLA$_2$ activity and to facilitate development of an effective treatment for pulmonary inflammation The ability of the LY311727 inhibitor to modulate PLA$_2$ activity was tested by adding increasing amounts of the inhibitor to a constant amount of lavage fluid from the 6015 rabbit in the presence of 1.2 mM CaCl$_2$ and a Tris buffer, pH 8.5. This mixture was incubated for 15 min. at 37° C. before addition of POPG substrate. PLA$_2$ activity was measured using the height of the eluted oleic acid HPLC peak, as described in previous Examples.

Results

Figure 13:
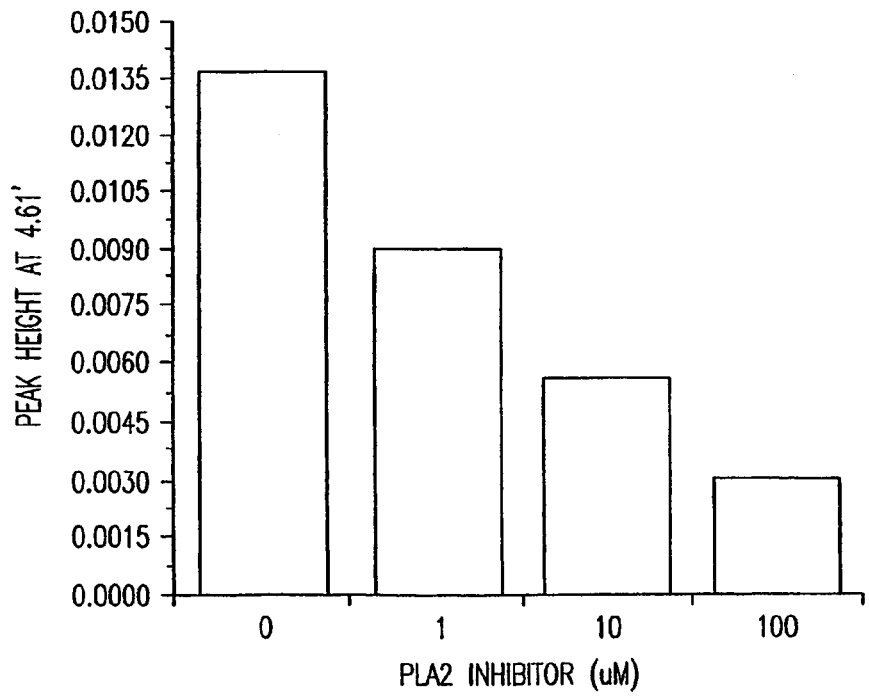
FIG. 13 graphically illustrates that $PLA_2$ activity in lavage fluids is reduced in a dosage dependent manner by addition of a $PLA_2$ inhibitor. As shown, the release of oleic acid from the POPG substrate after 30 min. incubation with lavage fluids (obtained from rabbit 6015) was indirectly proportional to the amount of LY311727 inhibitor. In other words, as increasing amounts of the inhibitor were added, decreasing amounts of $PLA_2$ activity were observed.
Figure 14:
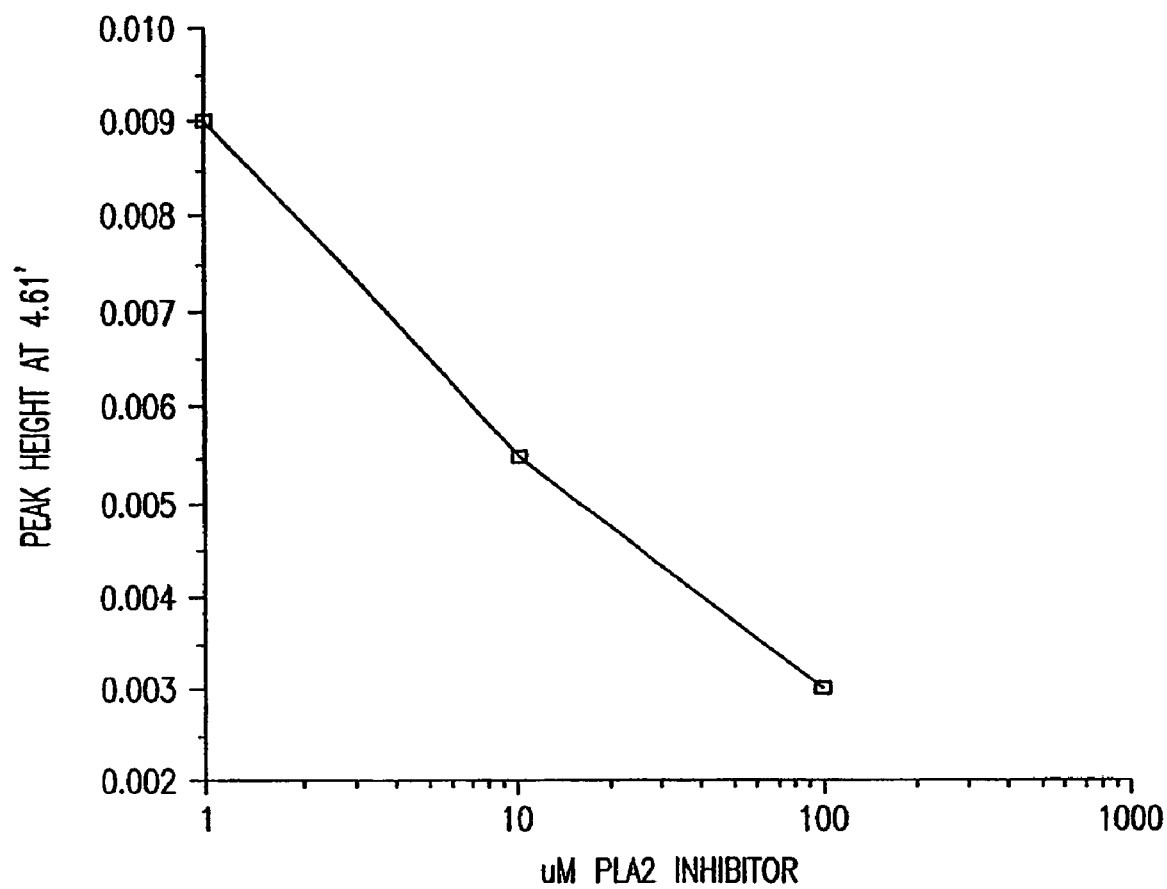
FIG. 14 graphically illustrates $PLA_2$ activity from BAL fluids as a function of the log of inhibitor concentration. As shown, BAL fluid PLA2 activity drops off significantly as the concentration of inhibitor increases.

FIG. 13 shows that the release of oleic acid from POPG after 30 min. incubation with lavage fluids obtained from rabbit 6015 was indirectly proportional to the amount of LY311727 inhibitor. In other words, as increasing amounts of the inhibitor were added, decreasing amounts of PLA2 activity were observed FIG. 14 graphically illustrates PLA$_2$ activity as a function of the log of inhibitor concentration. As shown, PLA$_2$ activity drops off significantly as the concentration of inhibitor increases.

EXAMPLE 16

Anti-Oxidants Inhibit Pulmonary Injury During Inflammation

Materials and Methods

Procedures employed were similar to those used in the foregoing Examples. Lung injury is induced in rabbits (1.0-1.5 kg) by bronchoalveolar lavage (BAL) using 5 µg/ml bacterial LPS in saline at a dosage of 20 ml/kg. At 2.5 hrs after LPS administration, the rabbits received 20 ml/kg phorbol myristate acetate (PMA) by bronchoalveolar lavage. The rabbits were divided into four (4) treatment groups with two to six animals in each group, as shown in Tables 6 and 7. At 2.5 hours after LPS administration, animals in group 1 received the anti-oxidant catalase intratracheally. Animals in group 2 received catalase intratracheally and intravenously. Animals in group 3 received catalase intratracheally and intravenously, as well as 5mg/ml Model Surfactant Mixture (KL$_4$) intratracheally. Animals in group 4 received no further treatment (control). The rabbits were ventilated at PIP 1 PEEP 3 cm H$_2$O pressure. The study was terminated at 6 hrs. Values in Tables 6 and 7 are averages+standard error of the mean (SEM).

Results

The results are provided in Tables 6 and 7. While the number of animals receiving surfactant plus catalase was too low to allow definitive conclusions to be made, administration of catalase did significantly improve lung function, as indicated by several factors.

TABLE 6

| Treatment | PaO$_2$ 4.5 hr | PaO$_2$ 6 hr | PaCO$_2$ 6 hr | Compliance (ml at 12 cm H$_2$O/Kg) |
|---|---|---|---|---|
| Catalase IT | 128 ± 15 (n = 5) | 119 ± 15 (n = 5) | 40 ± 3 (n = 5) | 10.1 ± 1.8 (n = 5) |
| Catalase IT & IV | 129 ± 19 (n = 4) | 124 ± 22 (n = 4) | 36 ± 5 (n = 4) | 8.4 ± 0.3 (n = 4) |
| Catalase IT & IV + Surfactant | 85 ± 6 (n = 2) | 85 ± 7 (n = 2) | 54 ± 9 (n = 2) | 8.8 ± 1.1 (n = 2) |
| Control | 78 ± 10 (n = 6) | 83 ± 10 (n = 5) | 56 ± 4 (n = 5) | 5.6 ± 06 (n = 5) |

TABLE 7

| Treatment | Albumin In BALF | Wet:Dry weight | BALF RBCs ($\times 10^3$) | Gross* Pathology | Histologic* Pathology |
|---|---|---|---|---|---|
| Catalase IT | 0.65 ± 0.16 (n = 5) | 7.4 ± 0.4 (n = 5) | 6.1 ± 3.6 (n = 5) | 1.6 ± 0.6 (n = 4) | 2.7 ± 0.6 (n = 5) |
| Catalase IT & IV | 0.50 ± 0.11 (n = 4) | 8.0 ± 0.6 (n = 4) | 2.3 ± 1.2 (n = 4) | 1.1 ± 0.4 (n = 4) | 2.9 ± 0.8 (n = 4) |
| Catalase IT & IV + Surf. | 0.62 ± 0.29 (n = 2) | 7.6 ± 0.6 (n = 2) | 2.1 ± 1.5 (n = 2) | 1.0 ± 0.5 (n = 2) | 3.3 ± 0.3 (n = 2) |
| Control | 1.05 ± 0.18 (n = 5) | 9.1 ± 0.6 (n = 6) | 18.1 ± 13.3 (n = 5) | 3.5 ± 0.2 (n = 5) | 3.8 ± 0.2 (n = 5) |

*on a scale of 0–4.

As indicated by the data in Tables 6 and 7, treatment with the anti-oxidant catalase protects pulmonary tissues from the destructive effects of inflammation. In particular, administration of catalase generally improved blood gases (generally higher $PaO_2$ and lower $PaCO_2$ for treated than non-treated animals). Moreover, the amount of albumin and red blood cells in the terminal lavage fluids and the wet to dry lung weight of treated animals was less than that observed in non-treated animals. Finally, the gross and histological pathology of treated animals was generally better than that of the non-treated animals. Hence, use of anti-oxidants during inflammation of pulmonary tissues may limit or reduce the injury to pulmonary tissues that is associated with inflammation.

REFERENCES

Amaro, A., Inhale Therapeutics Report, 14, 2001.
Cochrane, C G, et al., Am. J. Resp. and Crit. Care Med., Vol. 163:139, 2001.
Enhorning, et al., Am. J. Respir. Crit. Care Med., 151:554-556, 1995.
Freide, M., et al., Anal. Biochem., 211(1):117-122, 1993.
Glasser, et al., J. Biol. Chem., 263:10326, 1988.
Ilowite, et al., Am. Rev. Respir. Dis., 136:1445-1449, 1987.
Janoff, A., In: INFLAMMATION: BASIC PRINCIPLES AND CLINICAL CORRELATES, Gallin, J. L, et al., eds, 803-814, Raven Press, New York, 1988.
Jobe, et al., Am. Rev. Resp. Dis., 136:1032, 1987.
Kharasch, V. S., et al., Am. Rev. Respir. Dis., 144:909-913, 1991.
King, et al., Am. J. Physiol., 223:715-726, 1972.
Laube, et al., Chest, 95:822-830, 1989.
Lee, C. T., et al., New England J of Med., 304:192-196, 1981.
Maa, Y. F., Pharm. Dev. Technol., 2(3):213-223, 1997.
Maa, Y. F., et al., Pharm. Res., 15(5):768-775, 1998.
Master, K., SPRAY DRYING HANDBOOK, 5th edition, J. Wiley & Sons, New York, 1991.
Martin, F. J., In: SPECIALIZED DRUG DELIVERY SYSTEMS-MANUFACTURING AND PRODUCTION TECHNOLOGY, P. Tyle, ed., Marcel Dekker, New York, pp. 267-316, 1990.
Mayer, L. D., et al., Biochim. Biophys. Acta, 857:123-126, 1986.
Mayer, L. D., et al., Canc. Res., 49:5922-5930, 1989.
Meienhofer, J., In: HORMONAL PROTEINS AND PEPTIDES, Vol. 2, p. 46, Academic Press, New York, 1983.
Niven, R. W., In: MODULATED DRUG THERAPY WITH INHALATION AEROSOLS: REVISITED, A. J. Hickey, ed., Marcel Dekker, New York, 2002.
Notter, et al., Clin. Perinatology, 14:433-79, 1987.
Olson, F., et al., Biochim. Biophys. Acta, 557:9-23, 1979.
Puchell, E., et al., Eur. J. Clin. Invest., 15:389-394, 1985.
Revak, et al, Am. Rev. Respir. Dis., 134:1258-1265, 1986.
Robertson, Lung, 158:57-68, 1980.
Sarbolouki, M. N., Toliat, T., PDA J. Pharm. Sci. Technol., 52(1):23-27, 1998.
Schroder, E., Kubke, K., In: THE PEPTIDES, Vol. 1, Academic Press, New York, 1965.
Steward, J. M., Young, J. D., In: SOLID PHASE PEPTIDE SYNTHESIS, W.H. Freeman Co., San Francisco, 1969.
Szoka, F. Jr., et al., Ann. Rev. Biophys. Bioeng., 9:467-508, 1980.

All publications and patents are incorporated by reference herein, as though individually incorporated by reference.

The foregoing specification, including the specific embodiments and examples, is intended to be illustrative of the present invention and is not to be taken as limiting. Numerous variations and modifications can be effected without departing from the true spirit and scope of the present invention.

What is claimed:

1. A liquid or aerosolized composition, comprising a lung surfactant polypeptide, and a protease inhibitor, wherein the lung surfactant polypeptide is selected from the group consisting of:

| | |
|---|---|
| KLLLLKLLLLKLLLLKLLLLK, | (SEQ ID NO: 1) |
| KLLLLLLLLKLLLLLLLKLL, | (SEQ ID NO: 2) |
| KKLLLLLLLLKKLLLLLLLKKL, | (SEQ ID NO: 3) |
| DLLLLDLLLLDLLLLDLLLLD; | (SEQ ID NO: 4) |
| RLLLLRLLLLRLLLLRLLLLR; | (SEQ ID NO: 5) |
| RLLLLLLLLRLLLLLLLRLL; | (SEQ ID NO: 6) |
| RRLLLLLLLLRRLLLLLLLRRL, | (SEQ ID NO: 7) |
| RLLLLCLLLRLLLLCLLLR, | (SEQ ID NO: 8) |
| RLLLLCLLLRLLLLCLLLRLL, or | (SEQ ID NO: 9) |
| RLLLLCLLLRLLLLCLLLRLLLLCLLLR. | (SEQ ID NO: 10) | wherein the protease inhibitor is elafin and wherein the composition comprises about 0.1 to 10 dry weight percent of the lung surfactant polypeptide.

2. A liquid or aerosolized composition, comprising a lung surfactant polypeptide, and a protease inhibitor, wherein the lung surfactant polypeptide is selected from the group consisting of:

| | |
|---|---|
| KLLLLKLLLLKLLLLKLLLLK, | (SEQ ID NO: 1) |
| KLLLLLLLLKLLLLLLLKLL, | (SEQ ID NO: 2) |
| KKLLLLLLLLKKLLLLLLLKKL, | (SEQ ID NO: 3) |
| DLLLLDLLLLDLLLLDLLLLD; | (SEQ ID NO: 4) |
| RLLLLRLLLLRLLLLRLLLLR; | (SEQ ID NO: 5) |
| RLLLLLLLLRLLLLLLLRLL; | (SEQ ID NO: 6) |
| RRLLLLLLLLRRLLLLLLLRRL, | (SEQ ID NO: 7) |
| RLLLLCLLLRLLLLCLLLR, | (SEQ ID NO: 8) |
| RLLLLCLLLRLLLLCLLLRLL, or | (SEQ ID NO: 9) |
| RLLLLCLLLRLLLLCLLLRLLLLCLLLR. | (SEQ ID NO: 10) | wherein the protease inhibitor is a human secretory leukocyte protease inhibitor and wherein the composition comprises about 0.1 to 10 dry weight percent of the lung surfactant polypeptide.

3. A liquid or aerosolized composition, comprising a lung surfactant polypeptide, and a protease inhibitor, wherein the lung surfactant polypeptide is selected from the group consisting of:

| | |
|---|---|
| KLLLLKLLLLKLLLLKLLLLK, | (SEQ ID NO: 1) |
| KLLLLLLLLKLLLLLLLKLL, | (SEQ ID NO: 2) |
| KKLLLLLLLLKKLLLLLLLKKL, | (SEQ ID NO: 3) |
| DLLLLDLLLLDLLLLDLLLLD; | (SEQ ID NO: 4) |
| RLLLLRLLLLRLLLLRLLLLR; | (SEQ ID NO: 5) |
| RLLLLLLLLRLLLLLLLRLL; | (SEQ ID NO: 6) |
| RRLLLLLLLLRRLLLLLLLRRL, | (SEQ ID NO: 7) |
| RLLLLCLLLRLLLLCLLLR, | (SEQ ID NO: 8) |
| RLLLLCLLLRLLLLCLLLRLL, or | (SEQ ID NO: 9) |
| RLLLLCLLLRLLLLCLLLRLLLLCLLLR. | (SEQ ID NO: 10) | wherein the protease inhibitor is selected from the group consisting of: SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23 and wherein the composition comprises about 0.1 to 10 dry weight percent of the lung surfactant polypeptide.

4. The composition of one any of claims 1-3, wherein the lung surfactant polypeptide is

| | |
|---|---|
| KLLLLKLLLLKLLLLKLLLLK. | (SEQ ID NO 1) |

5. A method for treating pulmonary inflammation in a mammal in need thereof comprising administering to the mammal a therapeutically effective amount of the composition of any one of claims 1-3.

6. The method of claim 5, wherein the composition is administered parenterally, orally or intravenously.

7. The method of claim 5, wherein the composition is administered by bronchoalveolar lavage, inhalation or liquid bolus administration to the lungs.

8. The method of claim 5, wherein the lung surfactant polypeptide is KLLLLKLLLLKLLLLKLLLLK (SEQ ID NO:1).

* * * * *